(12) United States Patent
Castillo et al.

(10) Patent No.: US 6,929,808 B2
(45) Date of Patent: Aug. 16, 2005

(54) **METHODS OF ISOLATING AMYLOID-INHIBITING COMPOUNDS AND USE OF COMPOUNDS ISOLATED FROM *UNCARIA TOMENTOSA* AND RELATED PLANTS**

(75) Inventors: Gerardo Castillo, Seattle, WA (US); Paula Y. Choi, Bothell, WA (US); Elizabeth Nguyen, Renton, WA (US); Alan D. Snow, Lynnwood, WA (US)

(73) Assignee: ProteoTech, Inc., Kirkland, WA (US)

( * ) Notice: Subject to any disclaimer, the term of this patent is extended or adjusted under 35 U.S.C. 154(b) by 0 days.

(21) Appl. No.: 10/053,625

(22) Filed: Nov. 2, 2001

(65) Prior Publication Data

US 2002/0197692 A1 Dec. 26, 2002

Related U.S. Application Data

(60) Provisional application No. 60/245,958, filed on Nov. 3, 2000, and provisional application No. 60/271,777, filed on Feb. 27, 2001.

(51) Int. Cl.$^7$ ............... A51K 35/78; A61K 31/35
(52) U.S. Cl. ............... 424/725; 424/769; 514/456
(58) Field of Search ............... 424/725, 769; 514/456

(56) References Cited

U.S. PATENT DOCUMENTS

| | | | | |
|---|---|---|---|---|
| 4,698,360 A | | 10/1987 | Masquelier ............... | 514/456 |
| 6,264,994 B1 | * | 7/2001 | Castillo et al. ............... | 424/725 |
| 6,346,280 B1 | * | 2/2002 | Castillo et al. ............... | 424/725 |
| 6,509,381 B2 | * | 1/2003 | Empie et al. ............... | 514/783 |
| 6,607,758 B2 | * | 8/2003 | Castillo et al. ............... | 424/769 |

FOREIGN PATENT DOCUMENTS

| | | | |
|---|---|---|---|
| DE | 19627344 | * | 1/1998 |
| JP | 04145048 | * | 5/1992 |
| JP | 04145049 | * | 5/1992 |
| WO | WO 98/51302 | | 11/1998 |
| WO | WO-9851302 | * | 11/1998 |
| WO | WO 00/02571 | | 1/2000 |
| WO | WO 00/57707 | | 10/2000 |

OTHER PUBLICATIONS

Sigma Chemical Co. Catalog. 1994. p. 244—Product C3878, Chlorogenic acid.*

Aldrich Chemical Co. Catalog. 1990/1991. p. 297—Product C 4,420–6, Chlorogenic acid.*

C. Wirth and H. Wagner, "Pharmacologically active Procyanidines from the bank of *Uncaria tomentosa*," Phytomedicine, vol. 4 (3), pp. 265–266.

* cited by examiner

Primary Examiner—Christopher R. Tate
(74) Attorney, Agent, or Firm—Patrick M. Dwyer

(57) ABSTRACT

Assay-guided affinity fractionation and reverse phase high pressure liquid chromatography (HPLC) methodology to isolate, test and characterize the most active water-soluble ingredients within Cat's Claw, or *Uncaria tomentos*. These components appear to account for the majority of the amyloid or Aβ fibrillogenesis inhibitory activity. Individual fractions and/or compounds as isolated by HPLC are tested in relevant in vitro and/or animal models, and found to consistently demonstrate inhibition of amyloid or Aβ fibrillogenesis. Related extraction methods are disclosed.

2 Claims, 40 Drawing Sheets

METHODS OF ISOLATING AMYLOID-INHIBITING COMPOUNDS AND USE OF COMPOUNDS ISOLATED FROM *UNCARIA TOMENTOSA* AND RELATED PLANTS

This application claims priority to U.S. provisional applications No. 60/245,958 filed Nov. 3, 2000, and 60/271,777 filed Feb. 27, 2001.

TECHNICAL FIELD

The invention relates to the method of isolation and use of amyloid-inhibiting compounds derived from *Uncaria tomentosa* and related plants for the therapeutic intervention of Alzheimer's disease, type II diabetes, Parkinson's disease and other disorders involving amyloid accumulation; more particularly, it relates to methods of isolating amyloid-inhibiting compounds from *Uncaria tomentosa* and related plants, and to the use of those compounds.

BACKGROUND OF THE INVENTION

Alzheimer's disease is characterized by the accumulation of a 39–43 amino acid peptide termed the beta-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid as a major causative factor of Alzheimer's disease pathogenesis.

A variety of other human diseases also demonstrate amyloid deposition and usually involve systemic organs (i.e. organs or tissues lying outside the central nervous system), with the amyloid accumulation leading to organ dysfunction or failure. In Alzheimer's disease and "systemic" amyloid diseases, there is currently no cure or effective treatment, and the patient usually dies within 3 to 10 years from disease onset.

The amyloid diseases include, but are not limited to, the amyloid associated with Alzheimer's disease, Down's syndrome and hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid protein is referred to as amylin or islet amyloid polypeptide), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta2-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

Discovery and identification of new compounds or agents as potential therapeutic agents to arrest amyloid formation, deposition, accumulation and/or persistence that occurs in Alzheimer's disease, Parkinson's disease and other amyloidoses are desperately sought.

DISCLOSURE OF THE INVENTION

Methods of isolation for the identification and purification of the potent amyloid inhibitory ingredients within *Uncaria tomentosa* and related plants are disclosed. Use of such extracts from the inner bark and root parts of *Uncaria tomentosa* and related plant materials are anticipated to benefit human patients with Alzheimer's disease, type II diabetes, Parkinson's disease and other amyloidoses, due to the previously unknown ability of these compounds to inhibit amyloid fibril formation, and cause disruption/ dissolution of pre-formed amyloid fibrils.

The present invention pertains to the surprising discovery that specific extraction methods (and compounds derived from such extraction methods) when applied to the inner bark and root parts of *Uncaria tomentosa*, otherwise known as Uña de Gato (or Cat's claw), leads to the purification of a group of compounds (the group referred to herein as PTI-777), and their individual components (such as "compound H") which act as impressive inhibitors of Alzheimer's disease beta-amyloid protein (Aβ) formation and growth.

Previously our studies led to the identification of a natural substance derived from the Amazon rain forest woody vine, *Uncaria tomentosa*, and referred to as PTI-00703. See for instance U.S. patent applications Ser. Nos. 09/079,829, 09/198,824, and 09/208,278, which describe the initial discovery of derivatives of *Uncaria tomentosa* and related plant material extracts as inhibitors of amyloidosis of Alzheimer's disease, type II diabetes and other amyloid disorders.

In the present application, we used assay-guided affinity fractionation and reverse phase high pressure liquid chromatography (HPLC) methodology to isolate, test and characterize the most active water-soluble ingredients within PTI-00703 (collectively referred to as PTI-777) that appear to account for the majority of the Aβ fibrillogenesis inhibitory activity. PTI-777 and its individual fractions and/or compounds as isolated by HPLC were tested in relevant in vitro and/or animal models, and found to consistently demonstrate inhibition of Aβ fibrillogenesis. The present invention describes extraction methods for the isolation of PTI-777 and its individual fractions and/or components.

Further purification and in vitro testing of each of the PTI-777 compounds, as well as initial structural characterization studies suggest that the Aβ inhibitor compounds derived from *Uncaria tomentosa* are small molecules (~200–500 molecular weight) that belong to the general class of aromatic polyphenolic compounds. Two such compounds, chlorogenic acid ($C_{16}H_{18}O_9$; FW 354.31) and epicatechin ($C_{15}H_{14}O_6$; FW 290.27) were purified and identified by analytical techniques. In addition, data indicates that "compound H", the major compound within "fraction H" isolated from PTI-777 is a most potent inhibitor of Aβ amyloid fibrillogenesis.

In addition, PTI-777 has the ability to enter the brain as demonstrated by radiolabeling experiments, indicating that it has the potential to be very useful as a therapeutic agent for Alzheimer's disease, Parkinson's disease, and other central nervous system disorders involving deposition and accumulation of fibrillar proteins.

A primary object of the present invention is to establish new methods for the treatment of the amyloid diseases. In addition, the alpha-synuclein protein which forms fibrils, and is also Congo red and Thioflavin S positive, is found as part of Lewy bodies in the brains of patients with Parkinson's disease (Lewy in *Handbuch der Neurologie*, M. Lewandowski, ed., Springer, Berline pp.920–933, 1912; Pollanen et al, *J. Neuropath. Exp. Neurol.* 52:183–191, 1993; Spillantini et al, *Proc. Natl. Acad. Sci. USA* 95:6469–6473, 1998; Arai et al, *Neurosc. Lett.* 259:83–86, 1999). For purposes of this disclosure, Parkinson's disease, due to the fact that fibrils develop in the brains of patients with this disease (which are Congo red and Thioflavin S positive, and which also contain predominant beta-pleated sheet secondary structure), are regarded as a disease that also displays the characteristics of an amyloid-like disease.

Yet another object of the present invention is to use fraction "H" contained within *Uncaria tomentosa* and related plant materials for the treatment of amyloid formation, deposition, accumulation and/or persistence in Alzheimer's disease, type II diabetes, other amyloidoses and Parkinson's disease.

Yet another object of the present invention is to provide methods to isolate the active water-soluble amyloid inhibitory ingredients present within *Uncaria tomentosa* and related plant materials for use as potent agents which inhibit amyloid formation, amyloid deposition, amyloid accumulation, amyloid persistence, amyloid protein-amyloid protein interactions, and/or cause a dissolution/disruption of pre-formed or pre-deposited amyloid fibrils in Alzheimer's disease, type II diabetes, other amyloidoses and Parkinson's disease.

Yet another object of the present invention is to provide compositions and methods involving administering to a subject a therapeutic dose of an *Uncaria tomentosa* and related plant material extract which inhibits amyloid deposition. Accordingly, the compositions and methods of the invention are useful for inhibiting amyloidosis in disorders in which amyloid deposition occurs. The compounds of the invention can be used therapeutically to treat amyloidosis or can be used prophylactically in a subject susceptible to amyloidosis. The methods of the invention are based, at least in part, in directly inhibiting amyloid fibril formation, inhibiting amyloid fibril growth, and/or causing dissolution/disruption of preformed amyloid fibrils.

Yet another object of the present invention is to provide pharmaceutical compositions for treating amyloidosis. The pharmaceutical compositions include a therapeutic compound of the invention in an amount effective to inhibit amyloid deposition and a pharmaceutically acceptable vehicle.

Yet another object of the present invention is the use of any and all synthetic compounds made similar to an *Uncaria tomentosa* and related plant material extract for use as potent agents which inhibit amyloid formation, amyloid deposition, amyloid accumulation, amyloid persistence, amyloid protein-amyloid protein interactions, and/or cause a dissolution/disruption of pre-formed or pre-deposited amyloid fibrils in Alzheimer's disease, type II diabetes, other amyloidoses and Parkinson's disease.

In a particular aspect of the invention there is a method of isolation to purify and identify the water-soluble amyloid inhibitory ingredients from *Uncaria tomentosa* and/or extracts thereof. In one such method, an extract prepared from commercially obtained pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, bark bundles and/or bark powder, using the methods described in the present invention.

Another object of the present invention is to use the methods of extraction as described herein to provide an extract from *Uncaria tomentosa* and related plant materials for promoting mental alertness and for inhibiting the formation of brain amyloid deposits in a subject.

Yet another object of the present invention is to use the extract from *Uncaria tomentosa* and related plant materials for mental acuity; to promote mental alertness; to provide nutritional support for age or related cognitive or memory decline; to promote cognitive well being; to support brain function; to improve cognitive ability, mental performance or memory; to promote concentration and mental sharpness; to improve mental vitality; to promote greater mental clarity and alertness; to improve short term memory, for age associated cognitive or memory decline; to support normal brain function; to enhance learning or memory; to improve concentration; to enhance mental performance; to reduce mental decline; to reduce likelihood of age related brain disorders; to maintain good brain health; to reduce, eliminate, prevent, inhibit or disrupt/dissolve amyloid fibril or protein deposits, brain associated amyloid fibril deposits or brain associated amyloid protein deposits, amyloid fibril formation and growth or age associated amyloid fibril formation and growth, brain associated amyloid fibril formation and growth; to support healthy pancreatic function; to promote pancreatic function by helping to promote normal insulin function; to reduce, eliminate, prevent, inhibit or disrupt/dissolve amyloid fibril or protein deposits, and pancreas associated amyloid fibril formation and growth.

In particular the disclosure is directed to novel applications of assay guided fractionation leading to novel compounds and novel methods of use of those novel compounds, such as:

A method for isolating compounds that possess amyloid inhibitory activity from plant matter of the genus Uncaria having the following steps:

a) preparing a polar solvent extract (preferably a methanol extract) of Uncaria plant matter, where the polar solvent extraction is extraction with water, extraction with a polar alcohol or a water solution of a polar alcohol, extraction with a water solution of acetonitrile, or extraction with a water solution of another polar organic solvent such as triethanolamine, acetone, or the like, and running the extract through a first column that has a hydroxy group containing resin, a resin having hydrophobic characteristics but without any hydroxy groups, or a mixture of both;

b) eluting the first column with distilled water, followed by eluting with not more than 2–4 column bed volume washings with a dilute polar alcohol (such as methanol)/water solution having an alcohol/water ratio not greater than about 50/50, depending on which alcohol is used, and discarding any eluate, the object being to wash non-active material and fractions away, without appreciably eluting any active fractions (during particularization of any separation protocol—choice of solvent and concentration, volume of washings, flow rates and the like, appropriate analytical testing of putative discardable eluates is desirable, as will be appreciated by those skilled in the art, and such persons will know what tests to perform, such as for instance standard Thioflavin T testing to detect amyloid inhibiting substances);

c) eluting the first column with one or more column bed volume washings of a polar alcohol/water solution having an alcohol/water ratio somewhere at, or between, 50/50 and substantially pure alcohol, and collecting and drying the eluted volumes to a dried material. These volumes and their dried material contain the active amyloid inhibiting ingredients referred to in this disclosure as PTI-777.

It will be appreciated that in the drying step above, alternate conventional drying procedures may be substituted by those skilled in the art without departing from the scope of coverage, and in some cases, the drying step may be omitted In the method of above, the column that comprises hydroxy containing resin, resin having hydrophobic characteristics but without any hydroxy, or a mixture of both, may advantageously be a column such as a C2 column, C4 column, C18 column, or the like, or Tris-acrylate column, LH-20 column, Affi-prep 10 gel column, or the like. Also the polar alcohol/water solution preferably has an alcohol/water ratio of 75/25 or higher, and more preferably is pure or nearly pure alcohol, and preferably methanol.

The plant matter of the genus *Uncaria* is preferably taken from one or more of the various Uncaria species such as *tomentosa, attenuata, elliptica, guianensis, pteropoda, bernaysli, ferra* DC, *kawakamii, rhyncophylla, calophylla, gambir,* and *orientalis,* and more preferably, *Uncaria tomentosa.* The *Uncaria tomentosa* plant matter is preferably taken from the inner bark and/or the root.

Optionally the isolation method set forth above is extended with the further steps:

d) applying an aqueous solution of the dried material from step (c) to a second column comprising a hydrophobic resin, the second column having been preparatorily equilibrated in a solvent comprising about 95% water/5% acetonitrile, referred to herein as solvent A, and then eluting the second column with more solvent A and discarding the eluate.

e) eluting the second column with a mixture of solvent A containing about 10–15%, and preferably about 12.5%, of a solvent comprising about 95% acetonitrile/5% water, referred to herein as solvent B, and collecting and drying the eluted volumes to a dried material.

"About" as applied to solvent percentage compositions and generally to other percentages expressed in this disclosure generally refers to +/− about 2% points; thus 'about 95% water/5% acetonitrile', for example, can lie anywhere at or between 97% water/3% acetonitrile to 93% water/7% acetonitrile. In other instances, the words 'about' or 'substantially' are understood to mean a figure or amount somewhere close to the stated figure, varying from the stated figure or amount by as much as +/−5%–20% of the stated figure or amount.

Optimally, TFA (typically about 0.1%) is added to the solvents indicated for acid stability and added efficacy in resin column work, as will be appreciated by those skilled in the art.

The isolation method above may be yet further advantageously enhanced by having a hydrophobic resin in the second column, and selecting a column from one of the many so called 'carbon columns', or carbon/hydrophobic columns, each preferably containing no hydroxy groups, such as for instance a C18 SPE, Varian Chroma..Zone™, or other HPLC columns, or the like.

The isolation method above may be yet further advantageously extended by having the following additional steps:

f) making one or more injections of a solution of the dried material of step (c) or the dried material of step (e) in a solvent such as water, water/dilute alcohol or a solution of solvent A comprising no more than 10% solvent B, into an HPLC instrument with a diode array uv/vis detector and graphic display and a reverse-phase column;

g) eluting the material through the HPLC column using a solvent gradient profile as follows: 10% solvent B for about the first 20 minutes from start of elution, 10 to 100% solvent B gradient for about minutes 20 to 30 from start of elution, and 100 to 10% solvent B gradient for about minutes 30 to 32 from start of elution, while observing the uv/vis detector graphic display during the elution gradient over time, and separating fractions of the eluate at elution times corresponding to times associated with the graphic display peaks.

Suitable reverse phase columns will occur to, and be well known by, those skilled in the art, and with minor adjustments to the protocol described above, may be interchanged for any columns set forth here. As discussed above, one of the many so called 'carbon columns', or carbon/hydrophobic columns, each preferably containing no hydroxy groups, such as for instance a C18 SPE, Varian Chroma..Zone™, or other HPLC columns, or the like, may be employed.

It should be noted that the preferred diode array detector may be advantageously substituted with alternate detectors such as a RI (refractive index) detector, a total ion detector, or the like, in order to monitor and record intensity peaks over time that correspond to elution fractions, as does the uv/vis detector preferred.

In a particular embodiment, the reverse-phase column has dimensions of about 2.2 cm×25 cm and contains about 95 ml of C18 reverse phase resin. The solution of the dried material is advantageously a solution of about 50 mg of the dried material of step (c) in about 1–2 ml of solvent A, and the step of injecting the solution of dried material into the HPLC may be repeated as required to load the column. An HPLC column solution gradient flow rate is preferably set to about 5 mls per minute, and the solvent gradient profile is preferably 10% solvent B for 0 to 20 minutes, followed by 10 to 100% solvent B gradient for minutes 20 to 30, and 100% to 10% solvent B gradient from minutes 30 to 31; such that fractions F though N of the eluate are collected at the following times: fraction G (13–14 minutes), fraction F (15–16 minutes), fraction H (17–20 minutes), fraction I (21 minutes), fraction J (22–23 minutes), fraction K1 (24 minutes), fraction K2 (25 minutes), fraction L (26–27 minutes), fraction M (27–28 minutes), and fraction N (28–29 minutes).

In another embodiment, the reverse-phase column has dimensions of 1.0 cm×25.0 cm and contains about 20 ml of C18 reverse phase resin. The solution of the dried material of step (c) is a solution of about 50 $\mu$g of the dried material in 50–100 $\mu$l of solvent A, wherein the step of injecting the solution into the HPLC is repeated multiple times, wherein a HPLC column solution gradient flow rate is set to about 1.5 mls per minute, and further wherein the solvent gradient profile is 10% solvent B for 0 to 20 minutes, followed by 10 to 100% solvent B gradient for minutes 20 to 30, and 100% to 10% solvent B gradient from minutes 30 to 31; such that fractions F though O of the eluate are collected at the following times: fraction G (12–13 minutes), fraction F (13–14 minutes), fraction H (15 minutes), fraction I (16 minutes), fraction J (18–19 minutes), fraction K1 (20 minutes), fraction K2 (21 minutes), fraction L (21–23 minutes), fraction M (23 minutes), fraction N (24 minutes), and fraction O (26–27 minutes).

Steps (f) and (g) of the isolation method set forth above may alternatively proceed as follows:

f) injecting a solution of 1 gram of the dried material of step (c) in 5–10 ml of solvent A into an HPLC instrument having a Varian model 320 uv/vis detector set at 230 nm with a graphic display, the HPLC further comprising a 4.14 cm×25 cm Varian Dynamax column further comprising 380 ml of C-18 reverse phase resin, the column fitted to a Varian Prostar 215 solvent delivery system, or the like.

g) eluting the HPLC column at a solution gradient flow rate of about 50 ml/mlnute, and further wherein the solvent gradient profile is with a solvent C/solvent D gradient (referred to in the art for HPLC solvent gradients as "A/B", but as C/D here to avoid confusions with other A/B gradients referred to herein as standards of protocol elsewhere in this disclosure) as follows: 0–4 minutes, 25% D; 4–11 minutes, 25–30% D gradient; 11–14 minutes, 30–90% D gradient; 14–17 minutes, 90% D; and 17–19 minutes, 90–25% D gradient, where C is water and D is methanol, such that fractions F through O of the eluate are separated at elution times corresponding to times associated with the graphic display peaks.

Those skilled in the art will appreciate, and readily accommodate, without undue experimentation, that adjusting flow rates and gradients for substitution of various A/B gradient setups, such as substituting water/methanol for water/acetonitrile, will be necessary and appropriate, because for instance methanol is more polar than acetonitrile, and thus more methanol (25%) is needed compared to acetonitrile (10%) in the discussions herein. Even so, specific percentages, times and flow rates will readily be selectable for various choices of solvents, all in accordance with the teachings disclosed herein.

Alternatively the preparation in step (a) of the extract of *Uncaria* may proceed as follows:

1) adding 4000 ml of methanol to 1 kg of *Uncaria tomentosa* and mixing
2) centrifuging the mixture at ×2,500 g using a centrifuge for 30 minutes and collecting the supernatant;
3) extracting the insoluble material about 3 more times as steps a and b above;
4) combining the supernatants and evaporating to a dried extract, or to at least about 500 ml volume, using a rotary evaporator at 50° C.;
5) washing the dried extract, or the 500 ml volume, 4 times with 300 ml of petroleum ether, and discarding the ether layer;
6) further evaporating any remaining methanol to dryness using a rotary evaporator at 50° C.;
7) extracting the dried extract 5 times with 150 ml of distilled water, followed by centrifugation at 2,500×g for 30 minutes each time, and
8) combining the supernatants and then lyophilizing using a freeze-dryer.

Further preparation of the extract of *Uncaria* from the resulting lyophilized extract can use the following additional steps:

9) dissolving the resulting lyophilized extract into about 500 ml of distilled water, and applying 50–100 ml portions to a 400 ml LH-20 column equilibrated with distilled water.
10) eluting the LH-20 column with 1,100 ml of distilled water (~3 column volumes) and discarding the amber/yellow, non-active fractions;
11) eluting the LH-20 column with 1,100 ml of 100% methanol (~3 column volumes) and collecting a set of active fractions and evaporating to dryness using a rotary evaporator at 50° C.

Alternatively the aqueous solution of a dried material from step (c) may be further prepared by the following steps:

1) dissolving the dried material in water at 80 mg/ml and applying 5 ml at a time to a disposable C18 SPE column (10 gram) equilibrated in a first solvent comprising about 95% water/5% acetonitrile/0.1% TFA;
2) washing with 3 column bed volumes of the first solvent and discarding the eluate.
3) eluting with 3 column bed volumes of the first solvent further comprising about 12.5% of a second solvent comprising about 95% acetonitrile/5% water/0.1% TFA, and
4) lyophilizing the corresponding fractions using a freeze-dryer.

It will be appreciated that the various drying and volume reducing methods disclosed are well known to those skilled in the art, and effective substitutes are also well known. Other drying methods, where at least one object is to avoid oxidation of the extracted material, such as nitrogen atmosphere, or vacuum drying will occur to those skilled in the art without departing from the scope of invention set forth herein.

Alternately the aqueous solution of a dried material from step (c) is further prepared by the following steps:

1) dissolving the lyophilized fractions at 5 grams in 20 ml water and applying 20 ml at a time to a Varian Chroma..Zone™ apparatus
2) washing with 3 column bed volumes of a first solvent comprising about 95% water/5% acetonitrile/0.1% TFA and discarding the eluate;
3) eluting with 3 column bed volumes of the first solvent further comprising about 12.5% of a second solvent comprising about 95% acetonitrile/5% water/0.1% TFA, and
4) collecting and drying the next 3 column bed volumes of eluate.

Another, more particular, method for isolating water-soluble components from *Uncaria tomentosa* that possess amyloid inhibitory activity has the following steps:

a) adding 4000 ml of methanol to 1 kg of *Uncaria tomentosa* and mixing
b) centrifuging the mixture at ×2,500 g using a centrifuge for 30 minutes and collecting the supernatant, where it is understood that means for separating suspended matter from the liquid, such as overnight sedimentation by gravity or filtration may be substituted by those skilled in the art to separate suspended solids from solution,
c) extracting the insoluble material about 3 more times as steps a and b above;
d) combining the supernatants and evaporating to dryness (or until about 500 ml volume is reached) using a rotary evaporator at 50° C.,
e) taking the powdered extract (or about 500 ml volume), washing 4 times with 300 ml of petroleum ether, or other non-polar organic solvent, and discarding the ether (non-polar) layer,
f) evaporating the methanol to dryness using a rotary evaporator at 50° C.;
g) extracting the solid material 5 times with 150 ml of distilled water, followed by centrifugation at 2,500×g for 30 minutes each time;
h) combining the supernatants and then lyophilizing using a freeze-dryer;
i) dissolving the resulting lyophilized extract into about 500 ml of distilled water, and applying 50–100 ml portions to a 400 ml LH-20 column equilibrated with distilled water.

j) eluting the LH-20 column with 1,100 ml of distilled water (~3 column volumes) and discarding the amber/yellow, non-active fractions;

k) eluting the LH-20 column with 1,100 ml of 100% methanol (~3 column volumes) and collecting a set of active fractions and evaporating to dryness using a rotary evaporator at 50° C.;

l) dissolving the fractions of step k in water (80 mg/ml) and applying 5 ml at a time to a 10 gm disposable C18 SPE column equilibrated in solvent A (solvent A is 95% water/5% acetonitrile/0.1% TFA);

m) washing the column with 3 volumes of solvent A and discarding the eluate;

n) eluting the column with 3 volumes of solvent A containing 12.5% solvent B (solvent B is 95% acetonitrile/5% water/0.1% TFA) and lyophilizing the eluate;

o) taking 50 mg of the lyophilized eluate of step n and injecting multiple times into a Hewlett-Packard 1100 Series HPLC instrument with diode array detector, fitted with a 2.2 cm×25 cm Vydac 218TP1022 C18 reverse-phase column maintained at 25° C. and at a flow rate of 5 ml/min;

p) eluting the sample with the following solvent profile, 10% B for 0 to 20 minutes, 10–100% B gradient for minutes 20 to 30, and 100–10% B gradient for minutes 30–31, where B is 95% acetonitrile/5% water/0.1% TFA;

q) and separating and collecting the fractions into 11 major components defined as fraction G (13–14 minutes), fraction F (15–16 minutes), fraction H (17–20 minutes), fraction I (21 minutes), fraction J (22–23 minutes), fraction K1 (24 minutes), fraction K2 (25 minutes), fraction L (26–27 minutes), fraction M (27–28 minutes), and fraction N (28–29 minutes).

A novel composition further referred to herein as PTI-777 may thus be isolated according to any of the isolation processes set forth above. And other compositions further referred to herein as PTI-777 fractions, such as PTI-777 fraction G, PTI-777 fraction F, PTI-777 fraction H, PTI-777 fraction I, PTI-777 fraction J, PTI-777 fraction $K_1$, PTI-777 fraction $K_2$, PTI-777 fraction L, PTI-777 fraction M, PTI-777 fraction N, and PTI-777 fraction O, may also be isolated according to any of the processes set forth above that employ HPLC fractionation.

A further novel compound H may be isolated by a method having steps (a) through (c) as set forth above, and further having the steps:

d) applying an aqueous solution of the dried material from step (c) to a second column, LH-20 or the like, eluting the material from the column with successive column volumes of water/methanol mixtures containing 0.1% TFA, beginning with 25% methanol and increasing to 100% menthol in 25% increments, and collecting and combining the fractions;

e) separating, combining and drying a fraction to a dried material, referred to hereafter as compound H, by analytical HPLC, the fraction containing a peak occurring between 7–8 minutes from start of elution on a Dynamax 5µ C-18 column having dimensions of about 4.6 mm×25 cm, using an elution gradient of water for solvent A and methanol for solvent B, A and B each containing about 0.1% TFA, with detection at 280 nm, the gradient conditions being 0 to 9 min fro 25% to 36% B gradient, 3 to 10 min for 36 to 100% B gradient, 10 to 12 min for 100% B and 12 to 13 min for 100 to 25% B gradient, all at a flow rate of about 20 ml/min;

f) making one or more injections of a solution of the dried material of step (e) above in a solvent comprising water/methanol 80/20 containing about 0.1% TFA and applied at about 150 mg/run to a preparative HPLC Dynamax 5 µ C-18 column with dimensions of about 21.4 mm×25 cm, using substantially the same elution gradient as used in step (e) above, with detection at 280 and 300 nm, the gradient conditions being 0 to 3 min for 20% to 25% B gradient, 3 to 9 min for 25 to 45% B gradient, 9 to 10 min for 45 to 100% B gradient, 10 to 12 min for 100% B and 12 to 13 min for 100 to 25% B gradient, all at a flow rate of about 20 ml/min, the compound H fraction eluting between 7–8 minutes from start of elution, and;

g) repeating steps (e) and (f) above until the peak as seen on analytical HPLC in step (e) is relatively pure, thus ending, when appropriately dried, with substantially pure compound H.

Also disclosed is a method of treatment, prevention or management of an amyloidosis, or a disease related to alpha-synuclein, in a mammalian subject susceptible to, or afflicted by, the amyloidosis or alpha-synuclein disease. The method includes the step of administering to the subject a therapeutic amount of the composition produced in accordance with any of the methods set forth above, such as, in particular, PTI-777 and/or compound H., or any of fraction G, fraction F, fraction H, fraction I, fraction J, fraction $K_1$, fraction $K_2$, fraction L, fraction M, fraction N or fraction O.

This method may be efficaciously applied to any amyloidosis which has an associated amyloid, such as amyloidoses associated with Alzheimer's disease, Down's syndrome, hereditary cerebral hemorrhage with amyloidosis of the Dutch type, the amyloidosis associated with type II diabetes, the amyloidosis associated with chronic inflammation, various forms of malignancy and Familial Mediterranean Fever, the amyloidosis associated with multiple myeloma and other B-cell dyscrasias, the amyloidosis associated with the prion diseases including Creutzfeldt-Jakob disease, Gerstmann-Straussler syndrome, kuru and animal scrapie, the amyloidosis associated with long-term hemodialysis and carpal tunnel syndrome, the amyloidosis associated with endocrine tumors such as medullary carcinoma of the thyroid, and the alpha-synuclein associated diseases including Parkinson's disease and Lewy body disease, and in particular, Alzheimer's disease.

In this method the associated amyloid may be either beta-amyloid protein or Aβ, AA amyloid or inflammation-associated amyloid, AL amyloid, amylin or islet amyloid polypeptide, PrP amyloid, $beta_2$-microglobulin amyloid, transthyretin or prealbumin, or variants of procalcitonin.

Another method for the treatment, inhibition, prevention or management of amyloid fibril or alpha-synuclein fibril formation, deposition, accumulation, aggregation and/or persistence in a mammalian subject is disclosed, and the method includes the step of administering to the subject a therapeutic amount of any of the compositions isolated by any of the methods disclosed herein. Contemplated routes of administration of the method of treatment include oral administration, parenteral injection, intraperitoneal injection, intravenous injection, subcutaneous injection, or aerosol spray administration.

A novel pharmaceutical agent is disclosed that is comprised of a therapeutically effective amount of a material made according to any of the disclosed isolation processes, with the therapeutic amount of the material selected for efficacy in treating an amyloid disease in a patient.

Another pharmaceutical agent is disclosed that is comprised of a therapeutically effective amount of a chlorogenic acid and/or epicatechin, the compound and the therapeutic amount of the compound selected for efficacy in treating an amylold disease in a patient.

In either or both of the pharmaceutical agents disclosed above, the therapeutically effective amount of a material is a dosage in the range of from about 10 to 1,000 mg/kg of body weight of the patient, and more particularly from about 10 to 100 mg/kg of body weight of the parent. The pharmacological agent may also contain a pharmaceutically a cceptable carrier, diluent, or excipient. A therapeutically effective amount of the material is defined as an amount that has an amyloid inhibitory activity or efficacy greater than 50%, as compared to placebo, or no material at all.

It is yet another object of the invention to meet any or all of the needs summarized above.

These and other features and advantages of the present invention will become more fully apparent when the following detailed description of the invention is read in conjunction with the accompanying figures.

BEST MODE OF CARRYING OUT THE INVENTION

Amyloid and Amyloidosis

Figure 1:
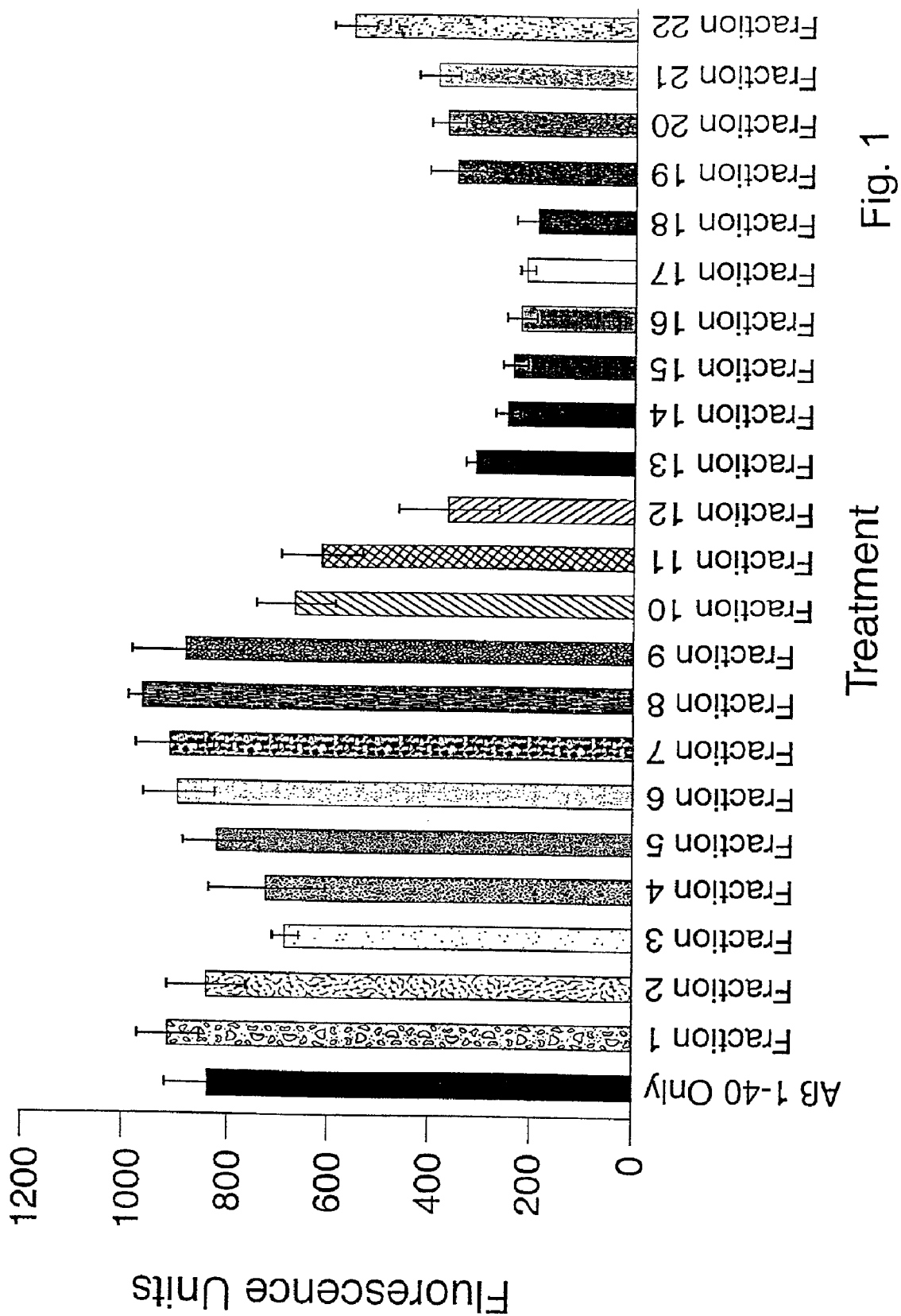
FIG. 1 is a Black and White Graph of a Thioflavin T Fluorometry Assay used to Identify Water-Soluble Fractions of *Uncaria tomentosa* that Possess Beta-Amyloid Protein (Aβ) Fibril Disruption Abilities.

Amyloid is a generic term referring to a group of diverse, but specific extracellular protein deposits which all have common morphological properties, staining characteristics, and x-ray diffraction spectra. Regardless of the nature of the amyloid protein deposited all amyloids have the following characteristics: 1) an amorphous appearance at the light microscopic level and appear eosinophilic using hematoxylin and eosin stains; 2) all stain with Congo red and demonstrate a red/green birefringence as viewed under polarized light (Puchtler et al., *J. Histochem. Cytochem.* 10:355–364, 1962), 3) all contain a predominant beta-pleated sheet secondary structure, and 4) ultrastructurally amyloid usually consist of non-branching fibrils of indefinite length and with a diameter of 7–10 nm.

Amyloid today is classified according to the specific amyloid protein deposited. The amyloid diseases include, but are not limited to, the amyloid associated with Alzheimer's disease, Down's syndrome and Hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta2-microglobulin amyloid), the amyloid associated with senile cardiac amyloid and Familial Amyloidotic Polyneuropathy (wherein the specific amyloid is referred to as prealbumin or transthyretin amyloid), and the amyloid associated with endocrine tumors such as medullary carcinoma of the thyroid (wherein the specific amyloid is referred to as variants of procalcitonin).

Although amyloid deposits in clinical conditions share common physical properties relating to the presence of a beta-pleated sheet conformation, it is now clear that many different chemical types exist and additional ones are likely to be described in the future. It is currently thought that there are several common pathogenetic mechanisms that may be operating in amyloidosis in general. In many cases, a circulating precursor protein may result from overproduction of either intact or aberrant molecules (ex. plasma cell dyscrasias), reduced degradation or excretion (serum amyloid A in some secondary amyloid syndromes and beta2-microglobulin in long-term hemodialysis), or genetic abnormalities associated with variant proteins (ex. familial amyloidotic polyneuropathy). Proteolysis of a larger protein precursor molecule occurs in many types of amyloidosis, resulting in the production of lower molecular weight fragments that polymerize and assume a beta-pleated sheet conformation as tissue deposits, usually in an extracellular location. What are the precise mechanisms involved, and the aberrant causes leading to changes in proteolytic processing and/or translational modifications is not known in most amyloids.

Systemic amyloids which include the amyloid associated with chronic inflammation, various forms of malignancy and Familial Mediterranean Fever (i.e. AA amyloid or inflammation-associated amyloidosis)(Benson and Cohen, *Arth. Rheum.* 22:36–42, 1979; Kamei et al, *Acta Path. Jpn.* 32:123–133, 1982; McAdam et al, *Lancet* 2:572–573, 1975; Metaxas, *Kidney Int.* 20:676–685, 1981), and the amyloid associated with multiple myeloma and other B-cell dyscrasias (i.e. AL amyloid)(Harada et al, *J. Histochem. Cytochem.* 19:1 15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, *N. Engl. J. Med.* 321:513–518, 1989). For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3–5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (amylin) deposits found in the islets of Langerhans in the pancreas of 90% of patients with type II diabetes (Johnson et al, *N. Enyl. J. Med.* 321:513–518, 1989; Lab. Invest. 66:522 535, 1992); the beta2-microglobulin amyloid deposits in the medial nerve leading to carpal tunnel syndrome as observed in patients undergoing long-term hemodialysis (Geyjo et al, *Biochem. Biophys. Res. Comm.* 129:701–706, 1985; *Kidney Int.* 30:385–390, 1986); the prealbumin/transthyretin amyloid observed in the hearts of patients with senile cardiac amyloid; and the prealbumin/transthyretin amyloid observed in peripheral nerves of patients who have Familial Amyloidotic Polyneuropathy (Skinner and Cohen, *Biochem. Bionhys. Res. Comm.* 99:1326–1332, 1981; Saraiva et al, *J. Lab. Clin. Med.* 102:590–603, 1983; *J. Clin. Invest.* 74:104–119, 1984; Tawara et al, *J. Lab. Clin. Med.* 98:811–822, 1989).

Alzheimer's Disease and the Aging Population

Alzheimer's disease is a leading cause of dementia in the elderly, affecting 5–10% of the population over the age of 65 years (1999 *Progress Report on Alzheimer's Disease*, National Institute on Aging/National Institute of Health, Silver Spring, Md.). In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's onward. Alzheimer's disease today affects 4–5 million Americans, with slightly more than half of these people receiving care at home, while the others are in many different health care institutions. The prevalence of Alzheimer's disease and other dementias doubles every 5 years beyond the age of 65, and recent studies indicate that nearly 50% of all people age 85 and older have symptoms of Alzheimer's disease (1999 *Progress Report on Alzheimer's Disease*, National Institute on Aging/National Institute of Health, Silver Spring, Md.). 13% (33 million people) of the total population of the United States is age 65 and older, and this % will climb to 20% by the year 2025 (1999 *Progress Report on Alzheimer's Disease*, National Institute on Aging/ National Institute of Health, Silver Spring, Md.).

Alzheimer's disease also puts a heavy economic burden on society as well. A recent study estimated that the cost of caring for one Alzheimer's disease patient with severe cognitive impairments at home or in a nursing home is more than $47,000 per year (*A Guide to Understanding Alzheimer's Disease and Related Disorders*, edited by Jorm, New York University Press, New York, 1987). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (1997 *Progress Report on Alzheimer's Disease*, National Institute on Aging/National Institute of Health).

Tacrine hydrochloride ("Cognex"), the first FDA approved drug for Alzheimer's disease is a acetylcholinesterase inhibitor (Cutler and Sramek, *N. Engl. J. Med.* 328:808 810, 1993). However, this drug has showed limited success in the cognitive improvement in Alzheimer's disease patients and initially had major side effects such as liver toxicity. The second more recently FDA approved drug, donepezil (also known as "Aricept"), which is also an acetylcholinesterase inhibitor, is more effective than tacrine, by demonstrating slight cognitive improvement in Alzheimer's disease patients (Barner and Gray, *Ann. Pharmacotherapy* 32:70–77, 1998; Rogers and Friedhoff, *Eur. Neuropsych.* 8:67–75, 1998), but is not believed to be a cure. Therefore, it is clear that there is a need for more effective treatments for Alzheimer's disease patients.

Amyloid as a Theralpeutic Target for Alzheimer's Disease

Alzheimer's disease is characterized by the deposition and accumulation of a 39–43 amino acid peptide termed the beta-amyloid protein, A$\beta$ or $\beta$/A4 (Glenner and Wong, *Biochem. Biophys. Res. Comm.* 120:885–890, 1984; Masters et al, *Proc. Natl. Acad. Sci. USA* 82:4245–4249, 1985; Husby et al, *Bull WHO* 71:105–108, 1993). A$\beta$ is derived by protease cleavage from larger precursor proteins termed beta-amyloid precursor proteins (or $\beta$PPs) of which there are several alternatively spliced variants. The most abundant forms of the $\beta$PPs include proteins consisting of 695, 751 and 770 amino acids (Tanzi et al, *Nature* 331:528–530, 1988; Kitaguchi et al, *Nature* 331:530–532, 1988; Ponte et al, *Nature* 331:525–527, 1988).

The small A$\beta$ peptide is a major component which makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science* 251:675–678, 1991). The pathological hallmarks of Alzheimer's disease is therefore the presence of "plaques" and "tangles", with amyloid being deposited in the central core of plaques. The other major type of lesion found in the Alzheimer's disease brain is the accumulation of amyloid in the walls of blood vessels, both within the brain parenchyma and in the walls of meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79–90, 1986; Pardridge et al, *J. Neurochem.* 49:1394–1401, 1987).

For many years there has been an ongoing scientific debate as to the importance of "amyloid" in Alzheimer's disease and whether the "plaques" and "tangles" characteristic of this disease, were a cause or merely the consequences of the disease. Within the last few years, studies now indicate that amyloid is indeed a causative factor for Alzheimer's disease and should not be regarded as merely an innocent bystander. The Alzheimer's A$\beta$ protein in cell culture has been shown to cause degeneration of nerve cells within short periods of time (Pike et al, *Br. Res.* 563:311–314, 1991; *J. Neurochem.* 64:253–265, 1995). Studies suggest that it is the fibrillar structure (consisting of a predominant $\beta$-pleated sheet secondary structure), characteristic of all amyloids, that is responsible for the neurotoxic effects. A$\beta$ has also been found to be neurotoxic in slice cultures of hippocampus (Harrigan et al, *Neurobiol. Aging* 16:779–789, 1995) and induces nerve cell death in transgenic mice (Games et al, *Nature* 373:523–527, 1995; Hsiao et al, *Science* 274:99–102, 1996). Injection of the Alzheimer's A$\beta$ into rat brain also causes memory impairment and neuronal dysfunction (Flood et al, *Proc. Natl. Acad. Sci.* 88:3363–3366, 1991; *Br. Res.* 663:271–276, 1994).

Probably, the most convincing evidence that A$\beta$ amyloid is directly involved in the pathogenesis of Alzheimer's disease comes from genetic studies. It has been discovered that the production of A$\beta$ can result from mutations in the gene encoding, its precursor, beta amyloid precursor protein (Van Broeckhoven et al, *Science* 248:1120–1122, 1990; Murrell et al, *Science* 254:97–99, 1991; Haass et al, *Nature Med.* 1:1291–1296, 1995). The identification of mutations in the beta-amyloid precursor protein gene which causes early onset familial Alzheimer's disease is the strongest argument that amyloid is central to the pathogenetic process underlying this disease. Four reported disease-causing mutations have now been discoveredwhich demonstrate the importance of A$\beta$ in causing familial Alzheimer's disease (reviewed in Hardy, *Nature Genet.* 1:233–234, 1992). All of these studies suggest that providing a drug to reduce, eliminate or prevent fibrillar A$\beta$ formation, deposition, accumulation and/or persistence in the brains of human patients is believed to serve as an effective therapeutic.

Parkinson's Disease and Alpha-Synuclein Fibril Formation

Parkinson's disease is a neurodegenerative disorder that is pathologically characterized by the presence of intracytoplasmic Lewy bodies (Lewy in *Handbuch der Neurologie*, M. Lewandowski, ed., Springer, Berline pp.920–933, 1912; Pollanen et al, *J. Neuropath. Exp. Neurol.* 52:183–191, 1993), the major components of which are filaments consisting of alpha-synuclein (Spillantini et al, *Proc. Natl. Acad. Sci. USA* 95:6469–6473, 1998; Arai et al, *Neurosc. Lett.* 259:83–86, 1999), an 140-amino acid protein (Ueda et al, Proc. Natl. Acad. Sci. USA 90:11282–11286, 1993). Two dominant mutations in alpha-synuclein causing familial early onset Parkinson's disease have been described suggesting that Lewy bodies contribute mechanistically to the degeneration of neurons in Parkinson's disease (Polymeropoulos et al, *Science* 276:2045–2047, 1997; Kruger et al, *Nat. Genet.* 18:106–108, 1998). Recently, in vitro studies have demonstrated that recombinant alpha-synuclein can indeed form Lewy body-like fibrils (Conway et al, *Nature Med.* 4:1318–1320, 1998; Hashimoto et al, *Brain Res.* 799:301–306, 1998; Nahri et al, *J. Biol. Chem.* 274:9843–9846, 1999). Most importantly. both Parkinson's disease-linked alpha-synuclein mutations accelerate this aggregation process that suggests that such in vitro studies may have relevance for Parkinson's disease pathogenesis. Alpa-synuclein aggregation and fibril formation fulfills of the criteria of a nucleation-dependent polymerization process (Wood et al, *J. Biol. Chem.* 274:19509–19512, 1999). In this regard alpha-synuclein fibril formation resembles that of Alzheimer's beta-amyloid protein (Aβ) fibrils. Alpha-synuclein recombinant protein, and non-amyloid component (known as NAC-P), which is a 35-amino acid peptide fragment of alpha-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al, *Brain Res.* 799:301–306, 1998; Ueda et al, *Proc. Natl. Acad. Sci. USA* 90:11282–11286, 1993).

Parkinson's disease alpha-synuclein fibrils, like the Aβ fibrils of Alzheimer's disease, also consist of a predominant beta-pleated sheet structure. Therefore, agents or compounds found to inhibit Alzheimer's disease Aβ amyloid fibril formation, are anticipated to also be effective in the inhibition of alpha-synuclein fibril formation. These agents or compounds would therefore also serve as therapeutics for Parkinson's disease, in addition to having efficacy as a therapeutic for Alzheimer's disease and other amyloid disorders.

*Uncaria tomentosa* (Cat's Claw)

The herb *Uncaria tomentosa*, also known as "Uña de Gato" (in Spanish) or "Cat's claw" (in English) refers to a woody vine which grows within the Peruvian Amazon rain forest. This slow growing vine takes 20 years to reach maturity, and can grow over 100 feet in length as it attaches and wraps itself around the native trees. It is found abundantly in the foothills, at elevations of two to eight thousand feet. The vine is referred to as "Cat's claw" because of its distinctive curved claw-like thorns which project from the base of its leaves. The native Indian tribes traditionally have boiled the inner bark and root of the herb to make a tea decoction and regard *Uncaria tomentosa* as a sacred medicinal plant. The highly effective properties contained within the inner bark of this plant are believed to have a profound and positive influence on the body, although scientific medical data is generally lacking on its potential benefits in humans. The alkaloids and phytochemicals in the inner bark of *Uncaria tomentosa* are almost identical to those found in the root, and harvesting this way preserves the plant and provides for the future of the rainforest.

Some of the active substances present in *Uncaria tomentosa* are alkaloids, which occur in the plant and its watery extract as a complex bound to tannins. In this form, only little of them can be activated. The complexes get split by the acid milieu of the stomach; the alkaloids get transformed into their hydrochloride form, and in this way, get well absorbed. A darker *Uncaria tomentosa* extract means more tannin is present and beneficial alkaloids are locked up with the tannins, which have formed a non-bioavailable and poorly absorbed complex. A light golden color of *Uncaria tomentosa* suggests that there is less tannins, and more alkaloids available in the extract.

Besides the presence of alkaloids, *Uncaria tomentosa* is believed to also contain other beneficial phytochemicals including quinovic acid glycosides, proanthocyanidins, polyphenols, triterpines and the plant sterols beta-sitosterol, stigmasterol and campesterol (P Steinberg "*Uncaria tomentosa* (Cat's Claw) a wondrous herb from the Peruvian rain forest", Townsend Letter for Doctors, May, 1994; P. Steinberg, "Cat's claw update-*Uncaria tomentosa*: that wondrous herb from the Peruvian rain forest", Townstead Letter for Doctors, August/September 1995).

*Uncaria tomentosa* is one of the most important plants in the South American Peruvian rainforest. A number of oxindole alkaloids have already been isolated from the inner bark of this plant. Two US patents (U.S. Pat. No. 4,844,901 and U.S. Pat. No. 4,940,725) describe the isolation and use of six oxindole alkaloids from *Uncaria tomentosa*, which are believed to be "suitable for the unspecified stimulation of the immunologic system". These oxindole alkaloids are believed to provide a general boost to the immune system as well as have a profound effect on the ability of white blood cells and macrophages to phagocytize harmful microorganisms and foreign matter. The most immunologically active alkaloid appears to be alloisopteropodine, isomer A, a pentacyclic oxindole alkaloid (U.S. Pat. No. 4,940,725).

Although some health care providers have suggested that *Uncaria tomentosa* may be used to treat a variety of ailments, nowhere has there been any use or suggestion of use, of this compound or extracts thereof for the treatment of amyloid formation, deposition, accumulation and/or persistence, such as that which occurs in the amyloidoses, including Alzheimer's disease and Parkinson's disease. The present invention clearly demonstrates the effectiveness of *Uncaria tomentosa* and specific extracts and derivatives thereof obtained from different commercial sources for the 1) inhibition of Alzheimer's Aβ amyloid fibril formation (important for patients in early to mid-stage Alzheimer's disease), and 2) causing the dissolution/disruption of pre-formed Alzheimer's disease amyloid fibrils (important for patients in mid-to-late stage Alzheimer's disease).

The following drawings are illustrative of the invention and are not meant to limit the scope of the invention.

FIG. 1 is a Black and White Graph of a Thioflavin T Fluorometry Assay used to Identify Water-Soluble Fractions of *Uncaria tomentosa* that Possess Beta-Amyloid Protein (Aβ) Fibril Disruption Abilities. Thioflavin T fluorometry demonstrates that fractions 13–18 (i.e. 52–72 minutes) contain components which disrupt/dissolve pre-formed Aβ 1-40 fibrils by 60–75%.

Figure 2:
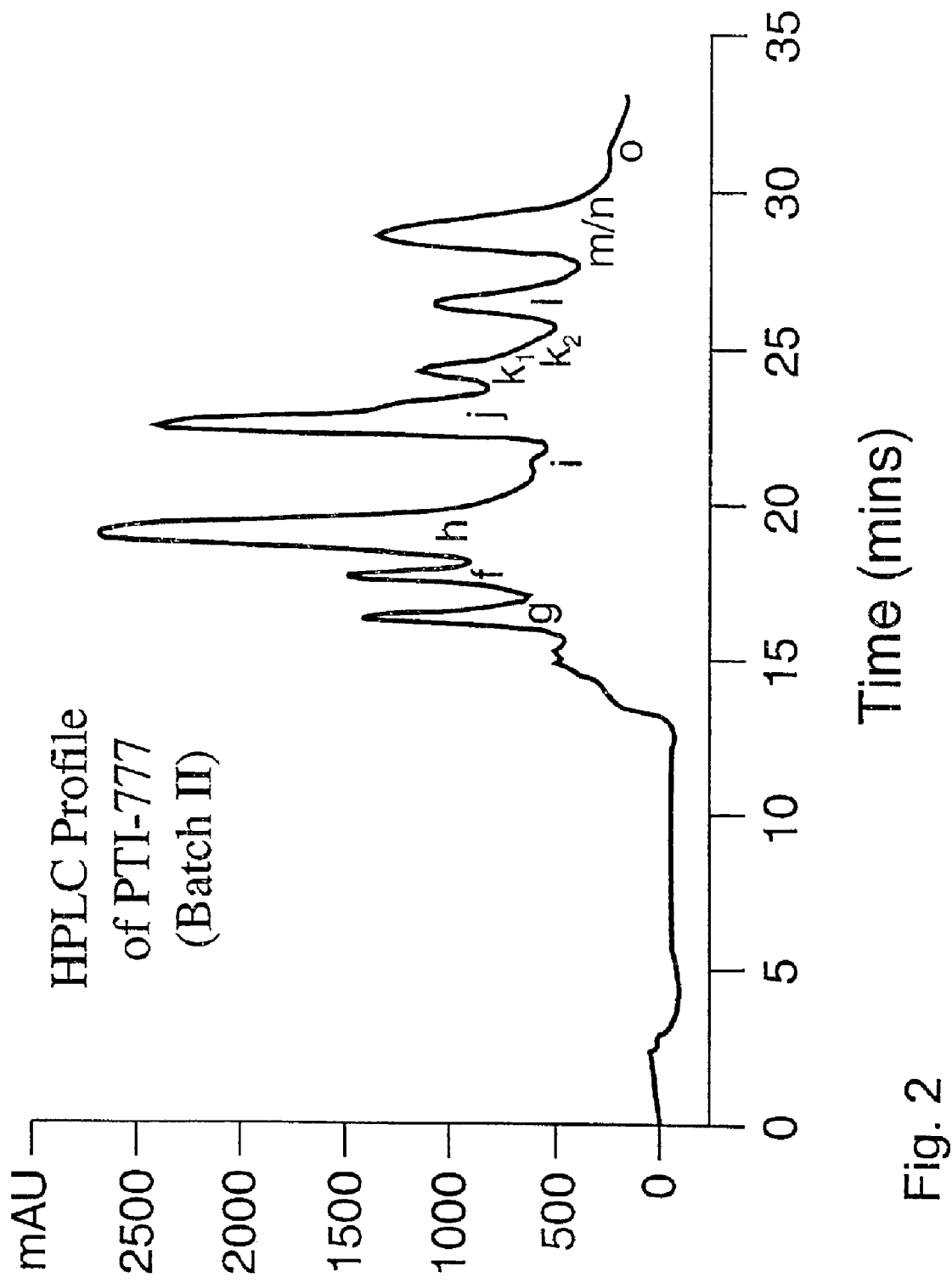
FIG. 2 is a Preparative HPLC Profile of PTI-777 (Batch II) which Demonstrates the Major Water-Soluble Amyloid Inhibitory Components Isolated form *Uncaria tomentosa*.

FIG. 2 is a Preparative HPLC Profile of PTI-777 (Batch II) which Demonstrates the Major Water-Soluble Amyloid Inhibitory Components Isolated form *Uncaria tomentosa*. HPLC was monitored at multiple wavelengths using a diode array and a representative profile at 230 nm is shown. Each of the fractions (F through O) were isolated for further purification, and initial structural characterization studies.

Figure 3:
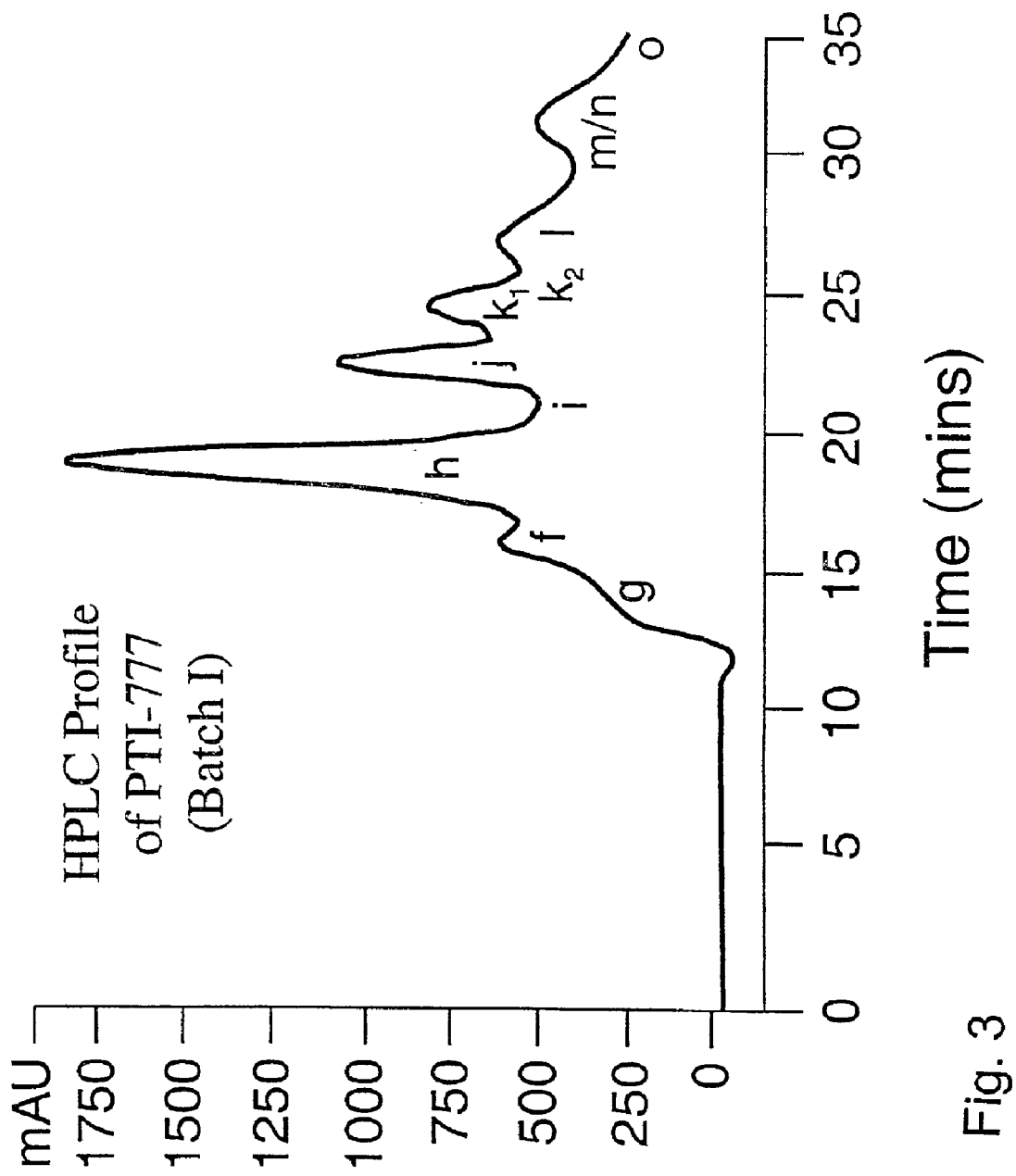
FIG. 3 is a Preparative HPLC Profile of PTI-777 (Batch I) that Demonstrates the Major Water-Soluble Amyloid Inhibitory Components Isolated from *Uncaria tomentosa*.

FIG. 3 is a Preparative HPLC Profile of PTI-777 (Batch I) that Demonstrates the Major Water-Soluble Amyloid Inhibitory Components Isolated from *Uncaria tomentosa*. HPLC was monitored at multiple wavelengths using a diode array and a representative profile at 230 nm is shown.

Figure 4:
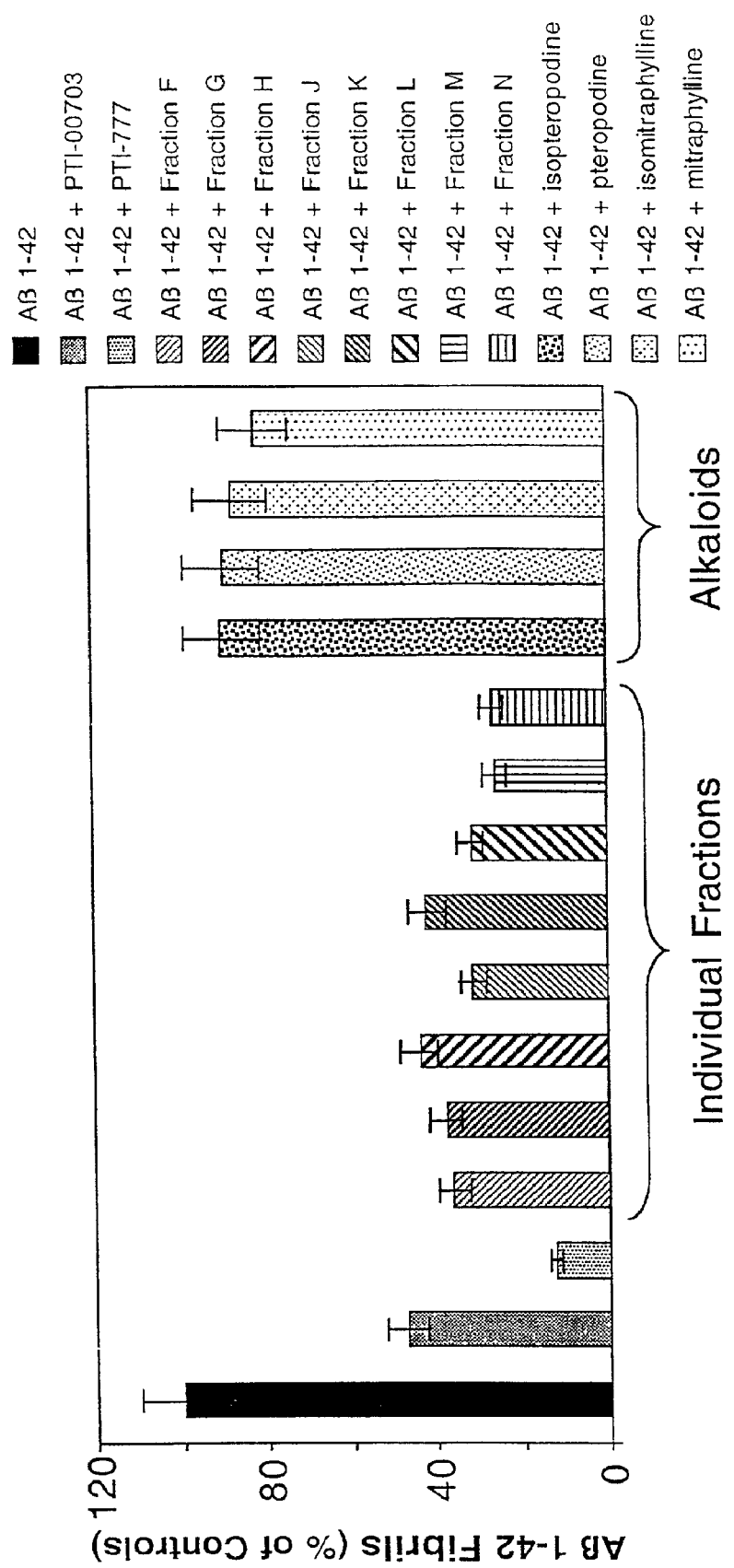
FIG. 4 is a Black and White Graph of a Thioflavin T Fluorometry Assay Demonstrating Disruption/Disassembly of Alzheimer's Aβ 1-42 Fibrils by PTI-777 and Individual PTI-777 Fractions.

FIG. 4 is a Black and White Graph of a Thioflavin T Fluorometry Assay Demonstrating Disruption/Disassembly of Alzheimer's Aβ 1-42 Fibrils by PTI-777 and Individual PTI-777 Fractions. Thioflavin T fluorometry results demonstrate a significant disruption of Aβ 1-42 fibrils by PTI-777, PTI-777 individual fractions (including fractions F, G, H, J, K, L, M and N), and to a lesser extent, PTI-00703. PTI-777 was the most effective disrupter, whereas *Uncaria tomentosa*-derived oxindole alkaloids including isopteropodine, pteropodine, isomitraphylline and mitraphylline were ineffective.

FIG. 5 is a Color Composite Demonstrating that PTI-777 and Individual Fractions of PTI-777 Cause of Disruption/Dissolution of Pre-Formed Alzheimer's Aβ Fibrils. 125 μM of Aβ 1-42 was incubated at 37° C. for 1 week either alone (Figure A), or in the presence of PTI-777 (Figure B), Fraction F (Figure C) or Fraction L (Figure D), at an Aβ:compound weight ratio of 1:5. Following staining of aliquots with Congo red, a marked reduction in amyloid congophilia (arrows in all figures; compare to Figure A) as viewed under polarized light was observed with PTI-777 (Figure B), and fractions F (Figure C) and L (Figure D).

Figure 6:
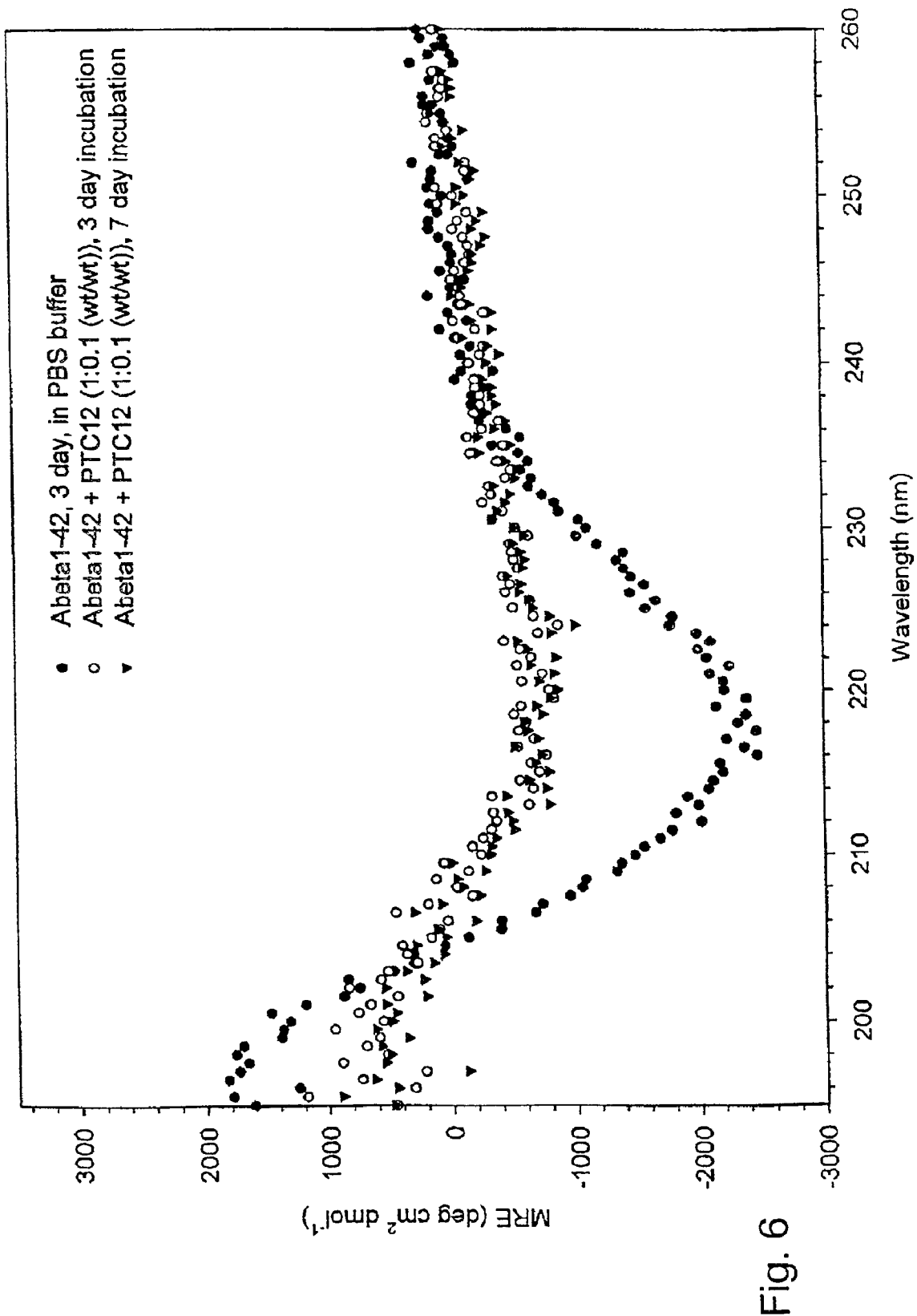
FIG. 6 is a Black and White Graph of a Circular Dichroism Spectroscopy Assay Demonstrating PTI-777 (referred to as PTC12 in this figure) Causes a Potent Disruption/Disassembly of B-sheet Structure in Aβ 1-42 Fibrils at 3 and 7 days following Incubation.

FIG. 6 is a Black and White Graph of a Circular Dichroism Spectroscopy Assay Demonstrating that PTI-777 (referred to as PTC12 in this figure) Causes a Potent Disruption/Disassembly of β-sheet Structure in Aβ 1-42 Fibrils at 3 and 7 days following Incubation. 50 μM Aβ 1-42 was incubated at 37° C. for 1 week either alone (closed circles), or in the presence of PTI-777 at an Aβ PTI-777 weight ratio of 1:0.1. At both 3 days (open circles) and 7 days (closed triangles), a 85–90% disruption/disassembly of β-sheet (at 220 nm) is shown.

FIG. 7 is a Black and White Composite Demonstrating Inhibition of Alzheimer's Amyloid Fibril Formation as Demonstrated by Negative Stain Electron Microscopy. 50 μM of Aβ 1-40 incubated for 1 week at 37° C. forms masses of Alzheimer's amyloid fibrils (arrowheads; Figure A). In the presence of PTI-777 (at an Aβ:PTI-777 weight ratio of 1:5), only amorphous non-fibrillar material is formed (Figure B, arrowheads) demonstrating that PTI-777 inhibits Alzheimer's amyloid fibril formation.

Figure 8:
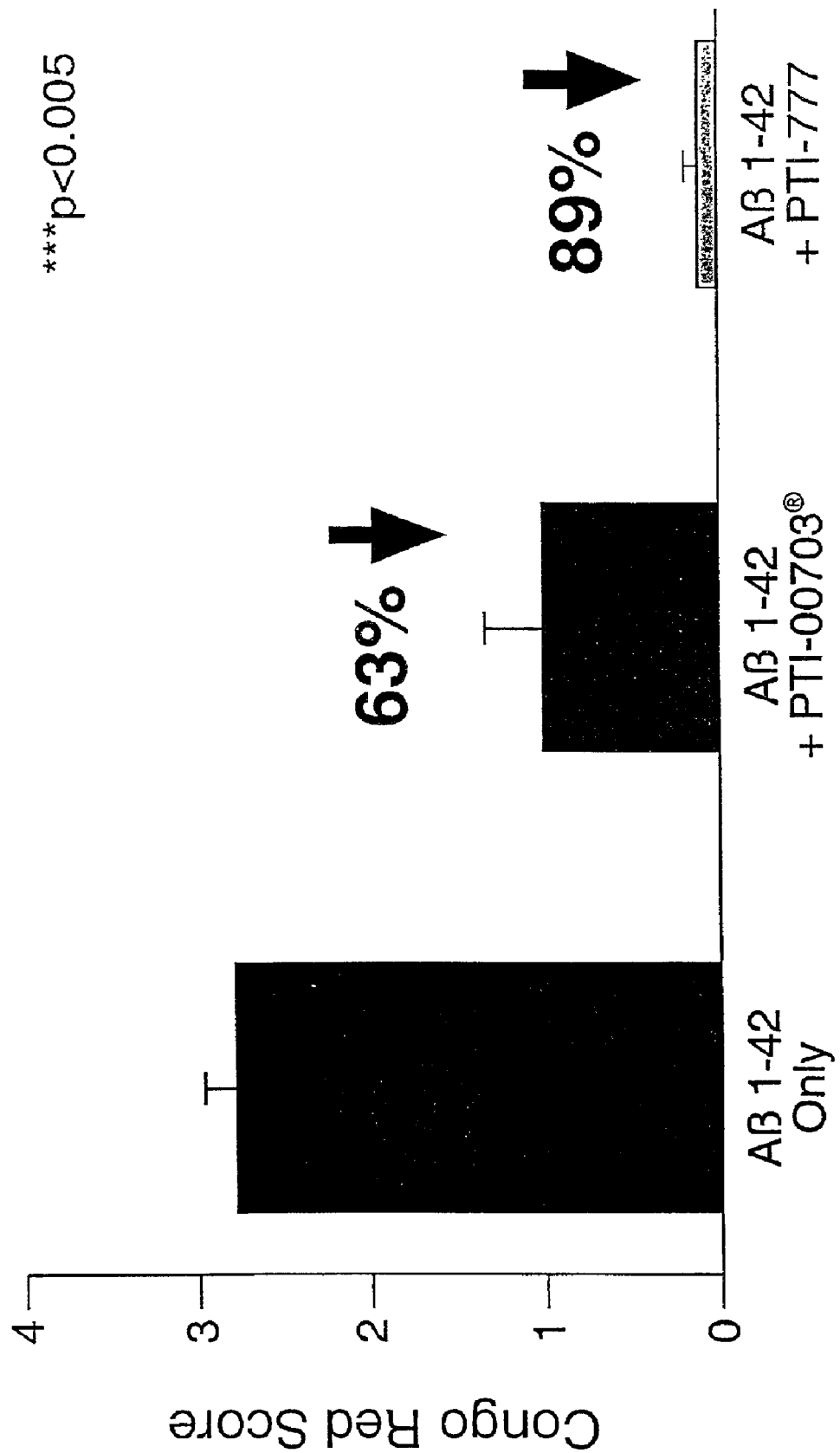
FIG. 8 is a graph Demonstrating that PTI-777 Markedly Inhibits Alzheimer's Aβ 1-42 Amyloid Deposition in a Rodent Model of Aβ Fibrillogenesis.

FIG. 8 is a graph Demonstrating that PTI-777 Markedly Inhibits Alzheimer's Aβ 1-42 Amyloid Deposition in a Rodent Model of Aβ Fibrillogenesis. 25 μg of Aβ 1-42, 25 μg of Aβ 1-42+PTI-00703, or 25 μg of Aβ 1-42+PTI-777 were directly infused into hippocampus for 1 week in adult Sprague-Dawley rats. The Aβ:PTI-00703 or Aβ:PTI-777 weight ratio was 1:5. Amyloid deposition in brain was as described previously (Snow et al, *Neuron* 12:219–234, 1994). The results demonstrated that PTI-777 was a much more potent inhibitor of Aβ 1-42 (by ~26%) fibril deposition than PTI-00703, indicating that the active ingredients of PTI-00703 were likely contained within PTI-777.

FIG. 9 is a Color Composite Demonstrating that PTI-777 Causes a Marked Inhibition of Astrocytosis in Brain. Tissue sections through dorsal hippocampus obtained from animals infused for 7 days with 25 μg of Aβ 1-42 in hippocampus (Figures A, B) or Aβ 1-42+PTI-777 (at an Aβ:PTI-777 weight ratio of 1:1)(Figures C and D) were immunostained with anti-glial fibrillary acidic protein (GFAP) to assess the degree of astrocytosis. As expected enhanced GFAP immunostaining (arrows) was observed adjacent to the cannula site (marked i) in animals infused with Aβ 1-42 only (Figures A and B). On the other hand, animals infused with PTI-777 showed a marked reduction in GFAP immunostaining (Figures C and D), suggestive of a marked inhibition in astrocytosis.

FIG. 10 are Black and White Graphs Demonstrating the $^1$H and $^{13}$C-NMR Profiles of Purified Fraction F of PTI-777.

Figure A shows the $^1$H-NMR profile of purified fraction F in pyridine (d$_5$) showing 12 discrete signals (see text for details). Figure B demonstrates the $^{13}$C-NMR profile of purified fraction F in pyridine (d$_5$) showing 16 discrete signal regions (see text for details).

Figure 11:
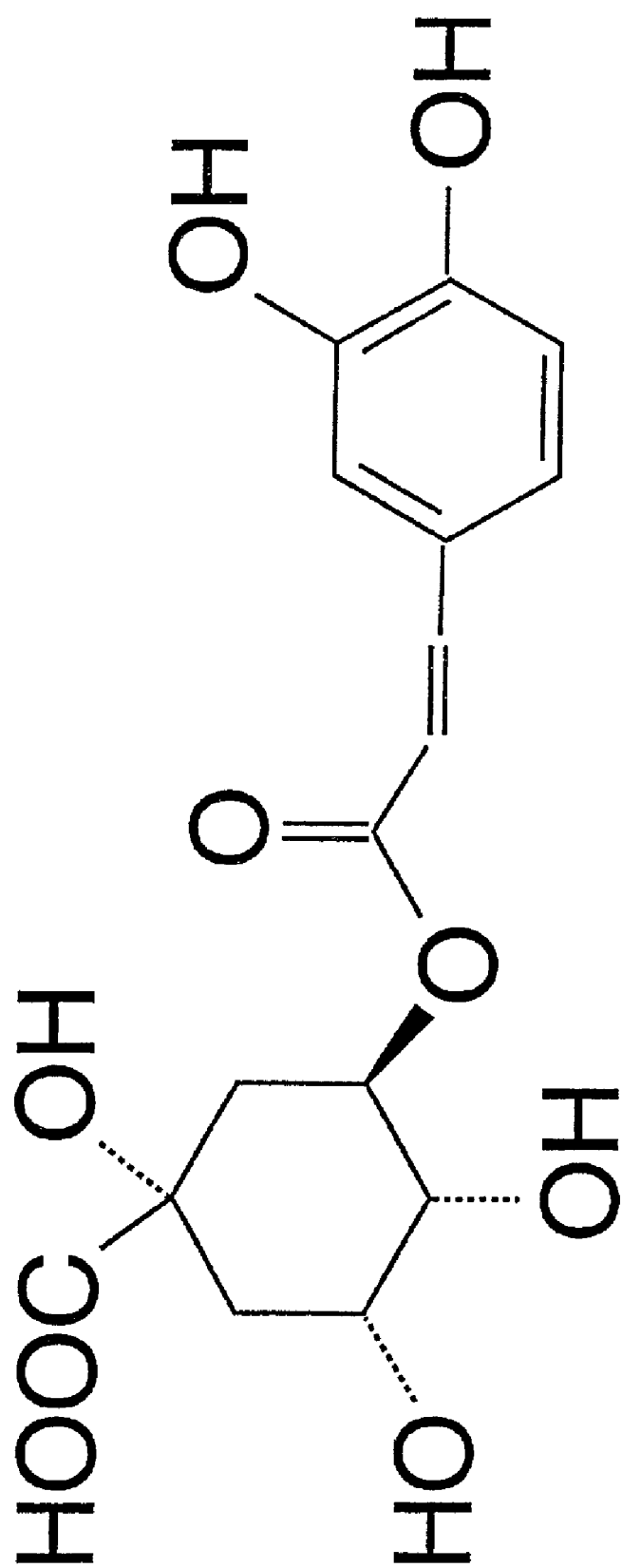
FIG. 11 is a Black and White Illustration of the Chemical Structure of Fraction F Identified as Chlorogenic Acid ($C_{16}H_{18}O_9$; molecular weight 354.31).

FIG. 11 is a Black and White Illustration of the Chemical Structure of Fraction F that was Identified as Chlorogenic Acid ($C_{16}H_{18}O_9$; molecular weight 354.31).

Figure 12A:
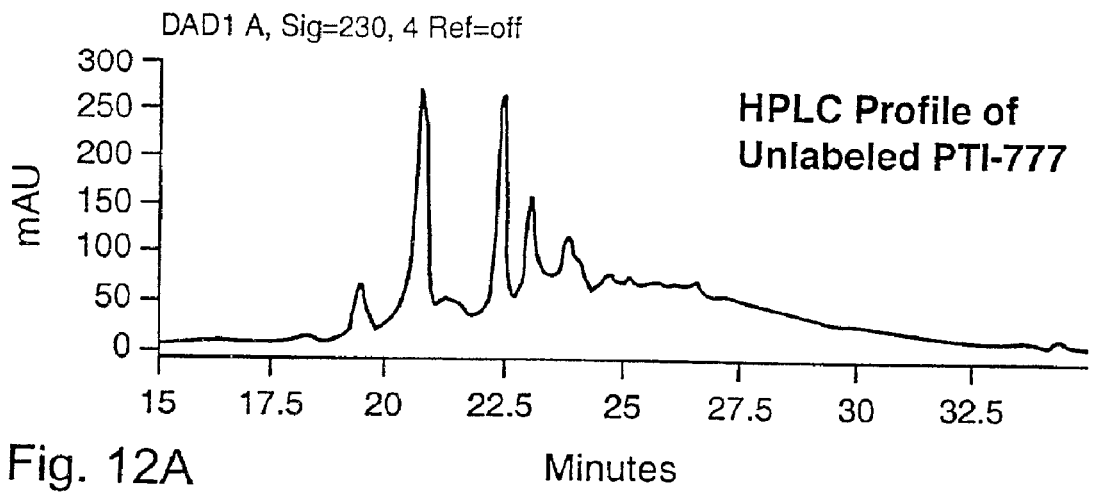
FIG. 12 is a Black and White Composite Demonstrating Successful $^3$H-Labelling of PTI-777 to Produce $^3$H-PTI-777 to be Used for Assessment of Blood-Brain-Barrier Penetration Studies.
Figure 12B:
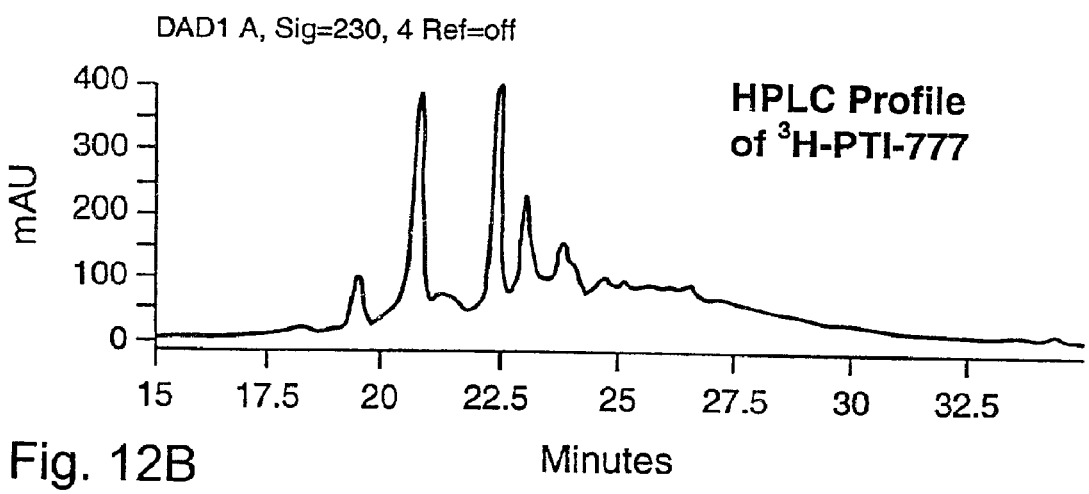
Figure 12C:
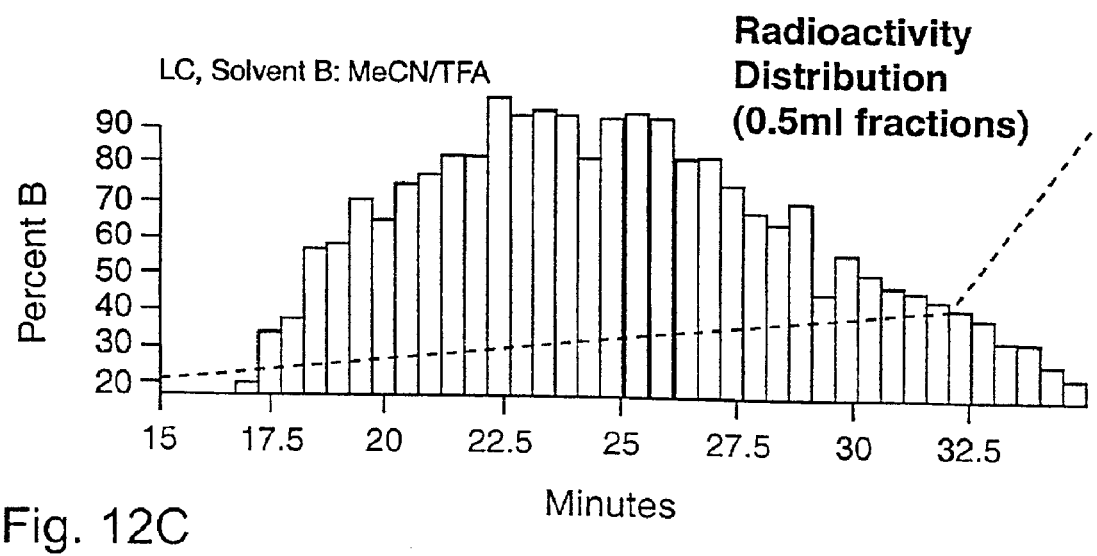

FIG. 12 is a Black and White Composite Demonstrating Successful $^3$H-Labelling of PTI-777 to Produce $^3$H-PTI-777 to be Used for Assessment of Blood-Brain-Barrier Penetration Studies. The upper panel demonstrates the HPLC profile of unlabelled PTI-777 which was monitored at multiple wavelengths using a diode array and a representative profile at 230 nm is shown. The middle profile demonstrates the HPLC profile of $^3$H-PTI-777 at 230 nm. Note that $^3$H-PTI-777 (middle panel) has nearly the identical HPLC profile as unlabelled PTI-777 (upper panel) indicating that labeling of PTI-777 with $^3$H did not structurally alter the PTI-777 compounds contained within. The lower panel demonstrates the radioactivity distribution (0.5 ml fractions) of $^3$H-PTI-777 as measured using a scintillation counter.

Figure 13:
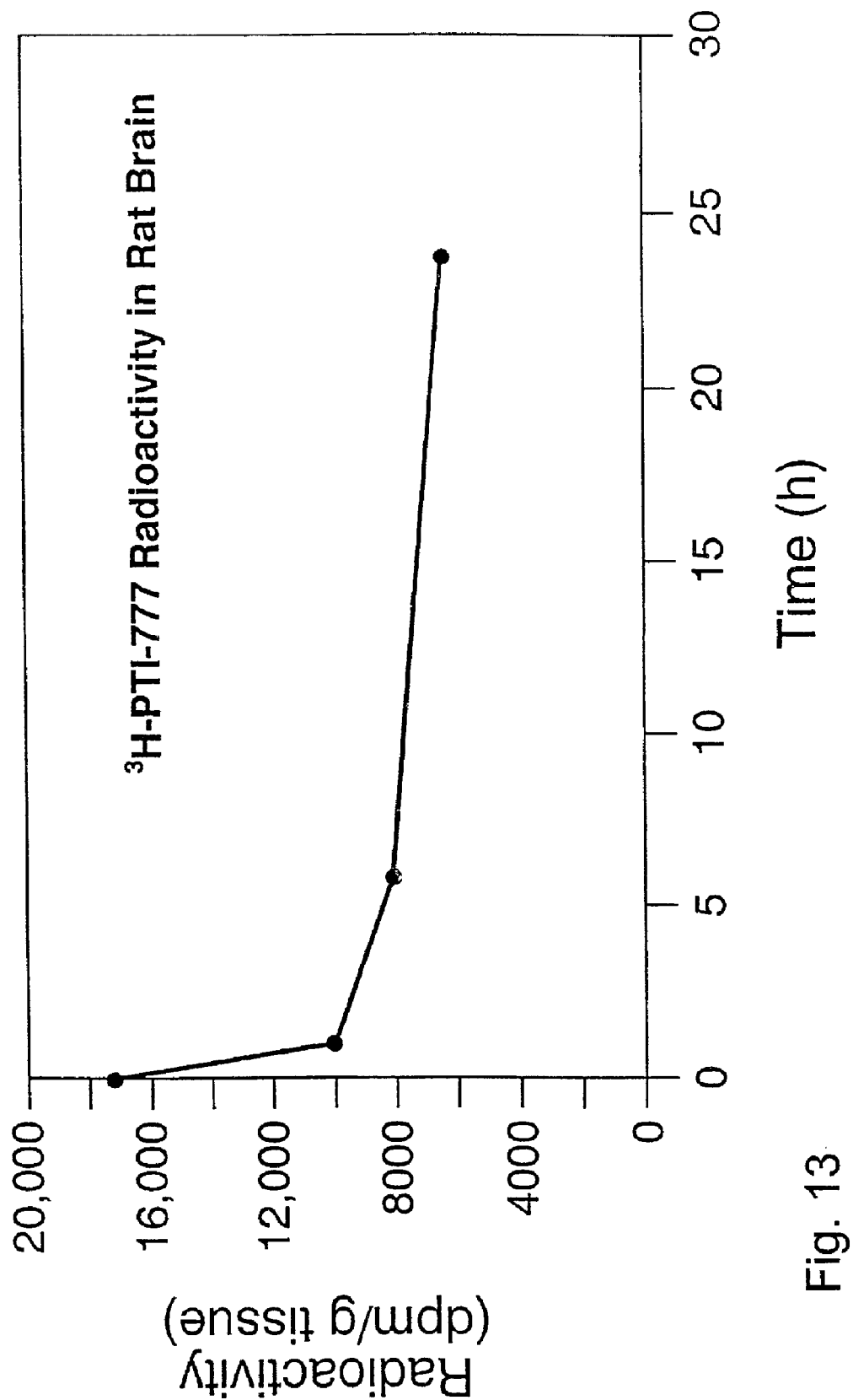
FIG. 13 is a Black and White Graph Demonstrating that Following Intravenous Administration of $^3$H-PTI-777 in Adult Sprague-Dawley Rats Radioactivity is Present in Brain Tissue.

FIG. 13 is a Black and White Graph Demonstrating that Following Intravenous Administration of $^3$H-PTI-777 in Adult Sprague-Dawley Rats Radioactivity is Present in Brain Tissue. Within 5 minutes of intravenous injection, $^3$H-PTI-777 is present in rodent brain tissue, and 40% of the radioactivity is maintained in brain over a 24-hour period. This study suggests that PTI-777 or individual components thereof have the ability to cross the blood-brain-barrier and enter the brain. Therefore, PTI-777 and components thereof have the ability to be used as a therapeutic for Alzheimer's disease and other central nervous system disorders.

Figure 14:
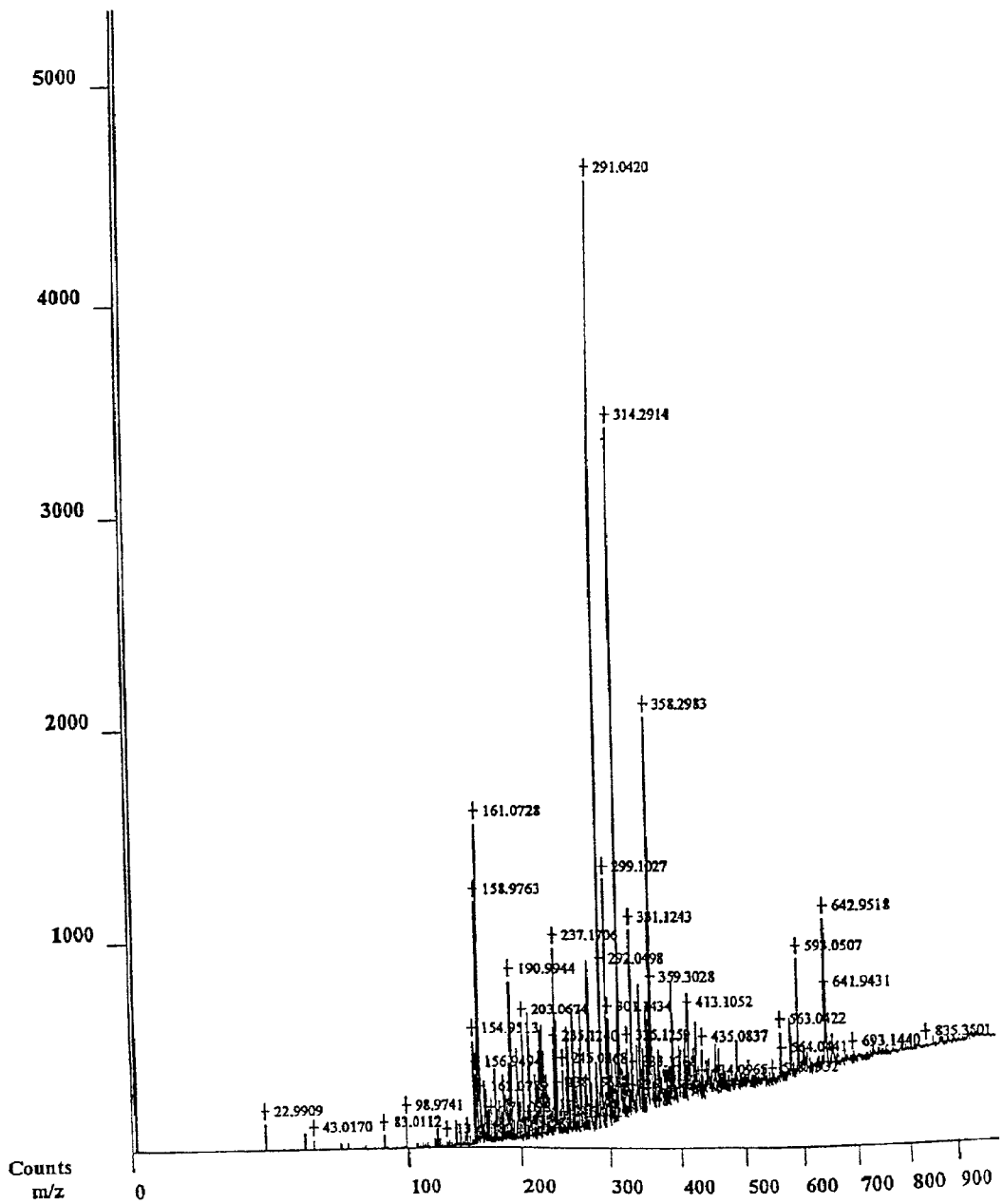
FIG. 14 is a Black and White Graph Demonstrating Electrospray Technique using Time of Flight Mass Spectroscopy of Purified PTI-777-Compound J.

FIG. 14 is a Black and White Graph Demonstrating Electrospray Technique using Time of Flight Mass Spectroscopy of Purified PTI-777-Compound J.

Figure 15:
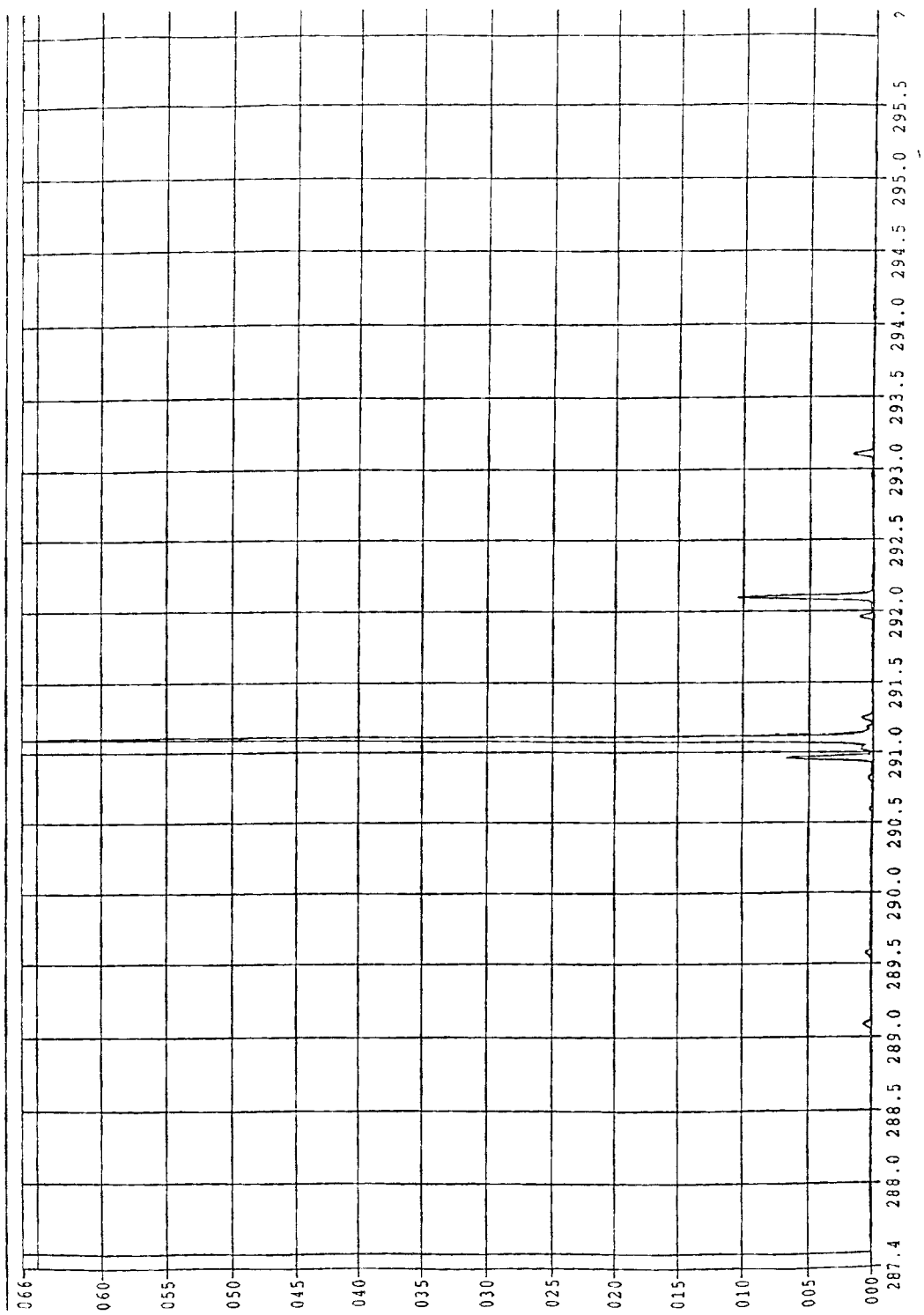
FIG. 15 is a Black and White Graph Demonstrating Electrospray Technique using Fourier Transform of Purified PTI-777-Compound J.

FIG. 15 is a Black and White Graph Demonstrating Electrospray Technique using Fourier Transform of Purified PTI-777-Compound J.

Figure 16:
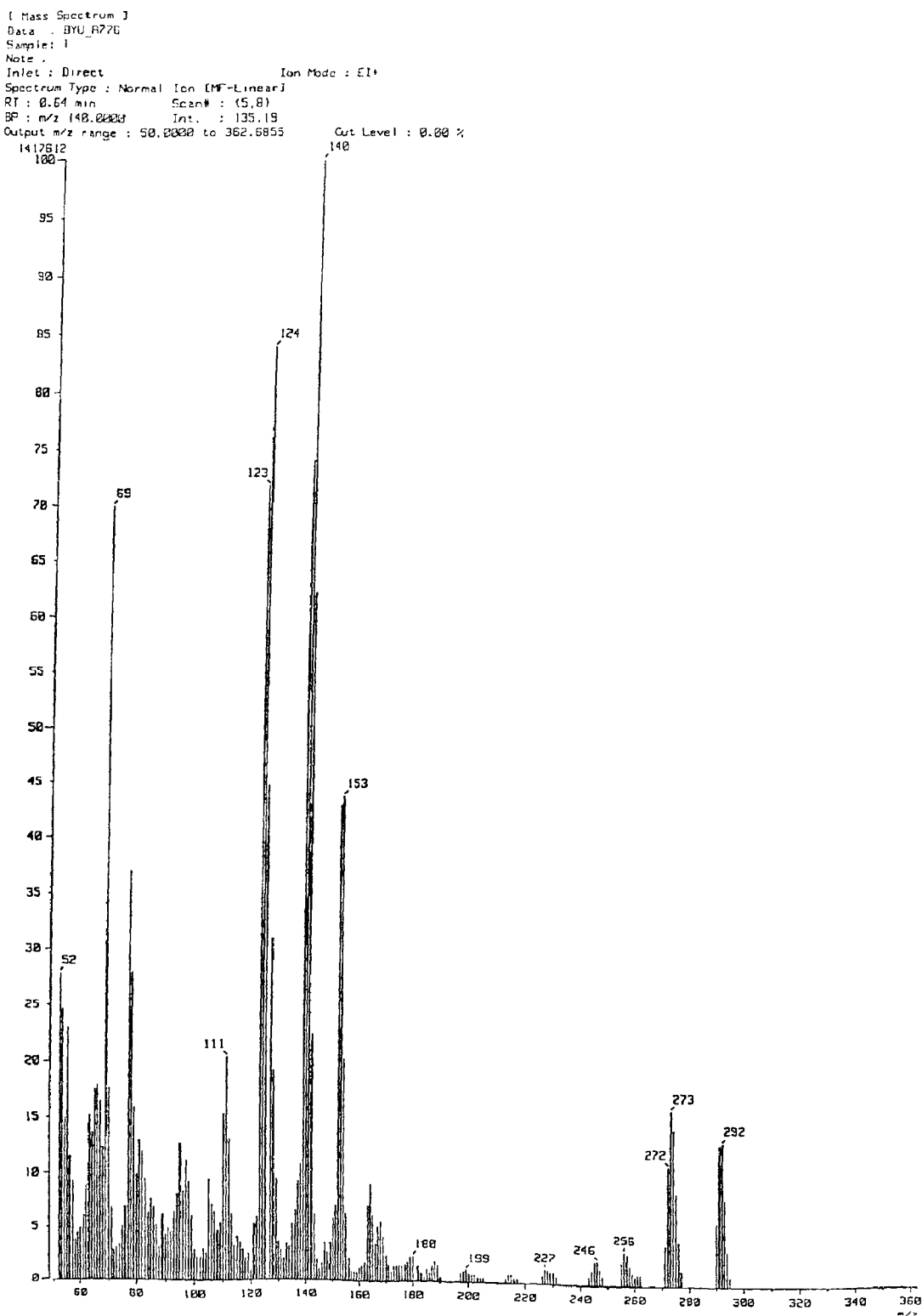
FIG. 16 is a Black and White Graph Demonstrating Electron Impact (EI) initiated Mass Spectrum of Purified PTI-777-Compound J.

FIG. 16 is a Black and White Graph Demonstrating Electron Impact (EI) initiated Mass Spectrum of Purified PTI-777-Compound J.

Figure 17:
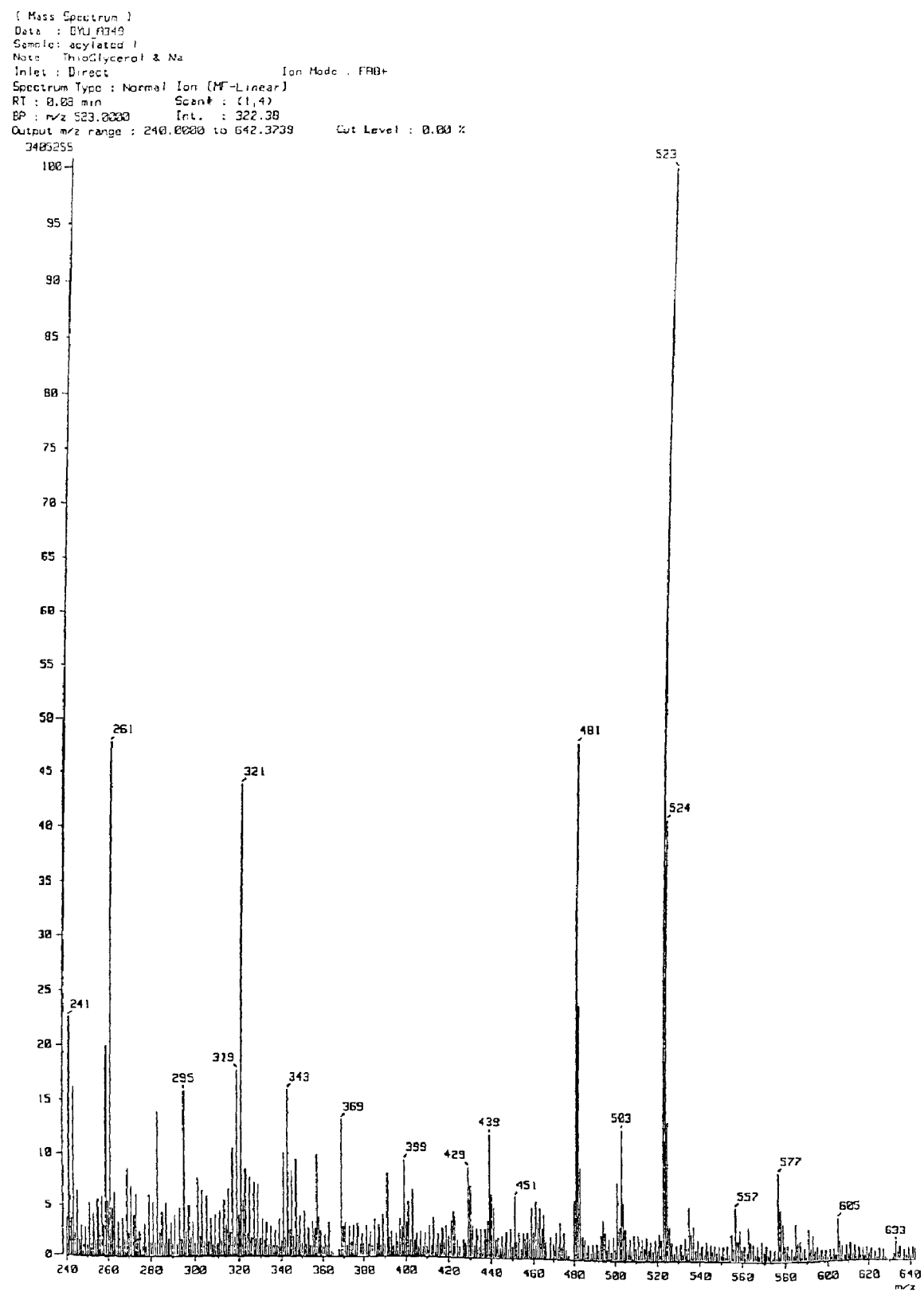
FIG. 17 is a Black and White Graph Demonstrating Fast Atom Bombardment (FAB) Mass Spectroscopy of PTI-777-Compound J that had been Acetylated.

FIG. 17 is a Black and White Graph Demonstrating Fast Atom Bombardment (FAB) Mass Spectroscopy of PTI-777-Compound J that had been Acetylated (i.e. Pentaacetate Derivative of PTI-777-Compound J).

Figure 18:
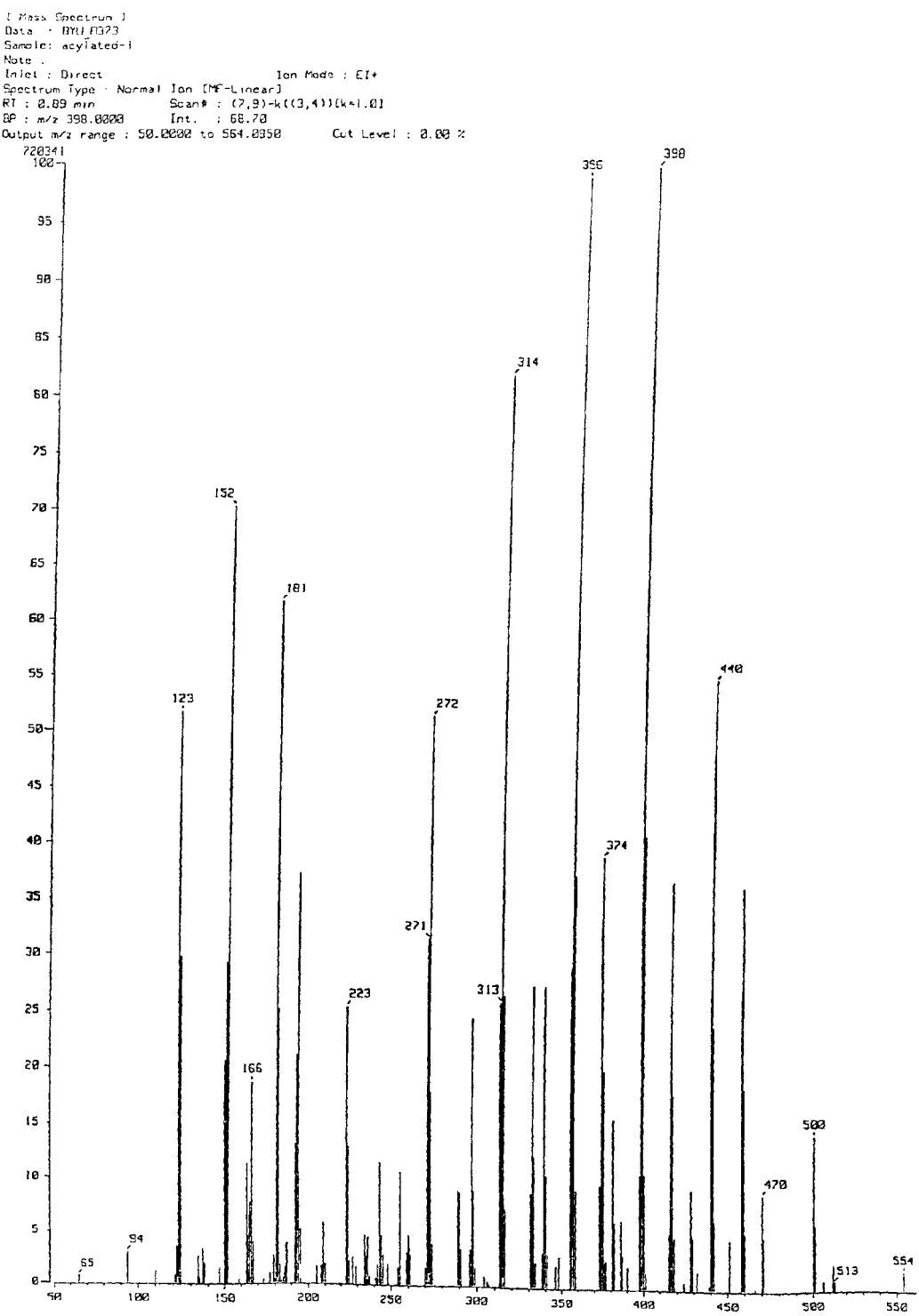
FIG. 18 is a Black and White Graph Demonstrating Electron Impact (EI) Mass Spectroscopy of PTI-777-Compound J that had been Acetylated.

FIG. 18 is a Black and White Graph Demonstrating Electron Impact (EI) Mass Spectroscopy of PTI-777-Compound J that had been Acetylated (i.e. Pentaacetate Derivative of PTI-777-Compound J).

Figure 19:
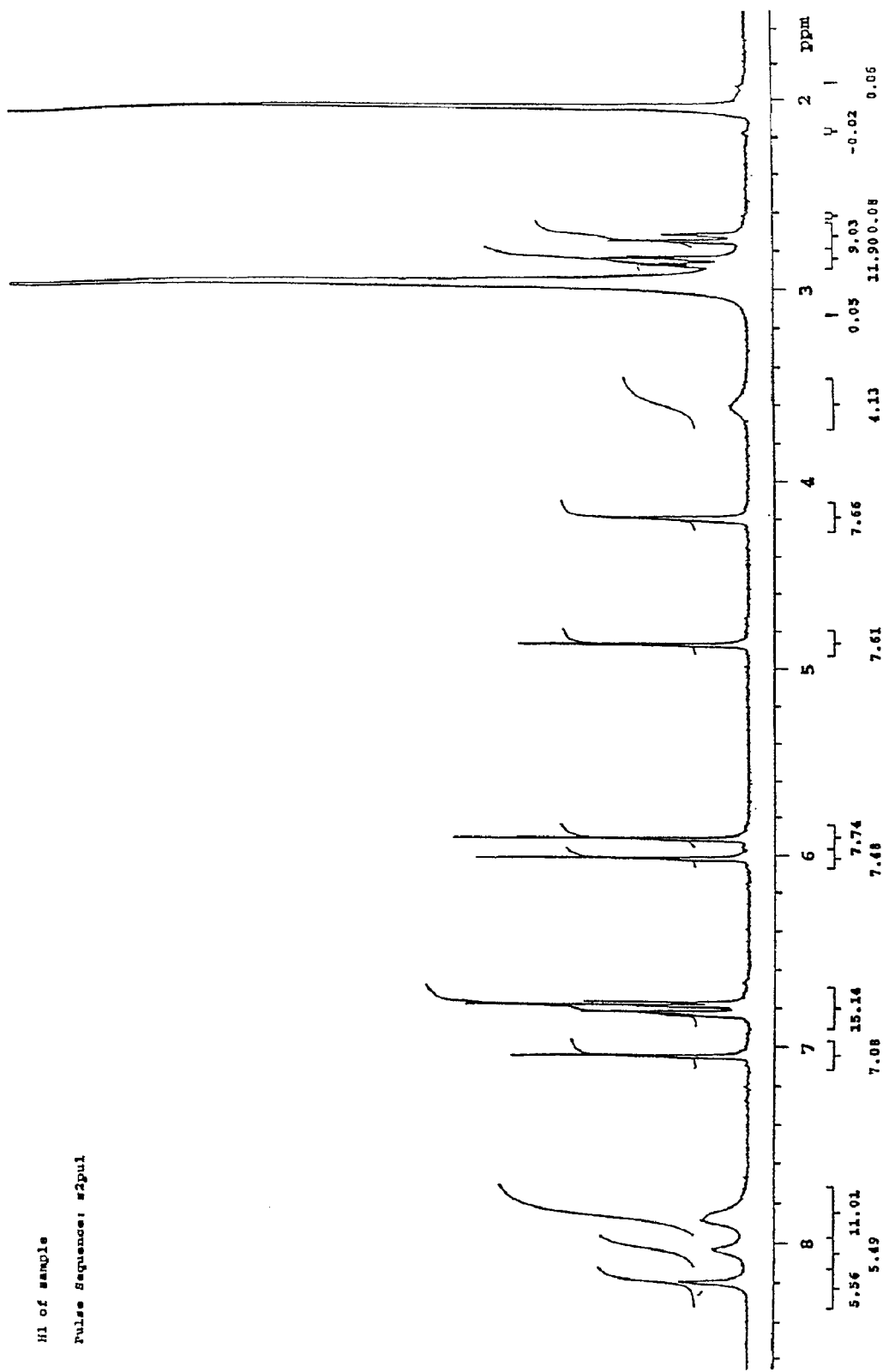
FIG. 19 is a Black and White Graph Demonstrating the $^1$H Nuclear Magnetic Resonance (NMR) Spectra of PTI-777-Compound J in $d_6$ Acetone.

FIG. 19 is a Black and White Graph Demonstrating the $^1$H Nuclear Magnetic Resonance (NMR) Spectra of PTI-777-Compound J in d$_6$ Acetone.

Figure 20:
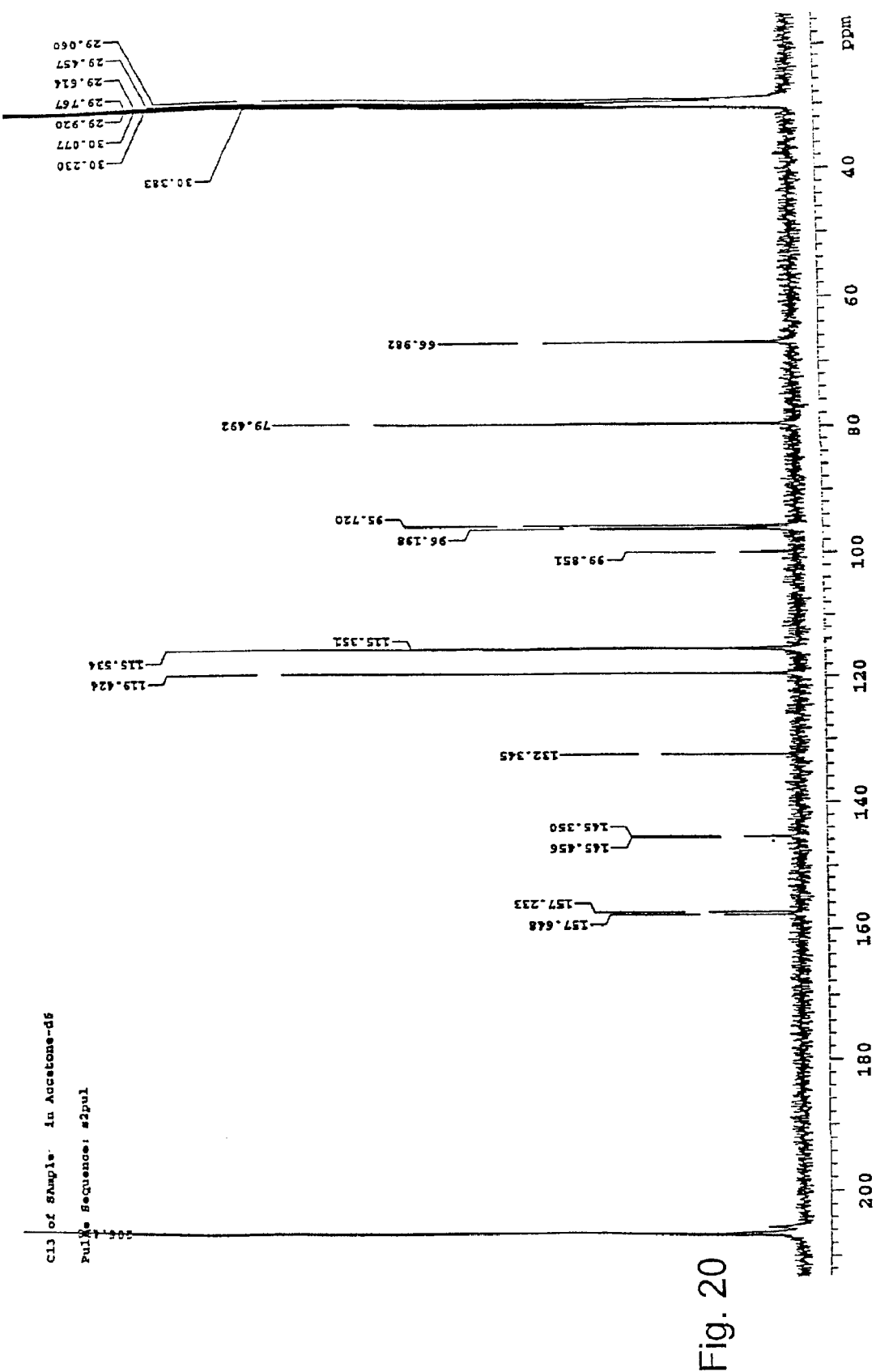
FIG. 20 is a Black and White Graph Demonstrating the $^{13}$C NMR Spectra of PTI-777-Compound J in $d_6$ Acetone.

FIG. 20 is a Black and White Graph Demonstrating the $^{13}$C NMR Spectra of PTI-777-Compound J in d$_6$ Acetone.

Figure 21:
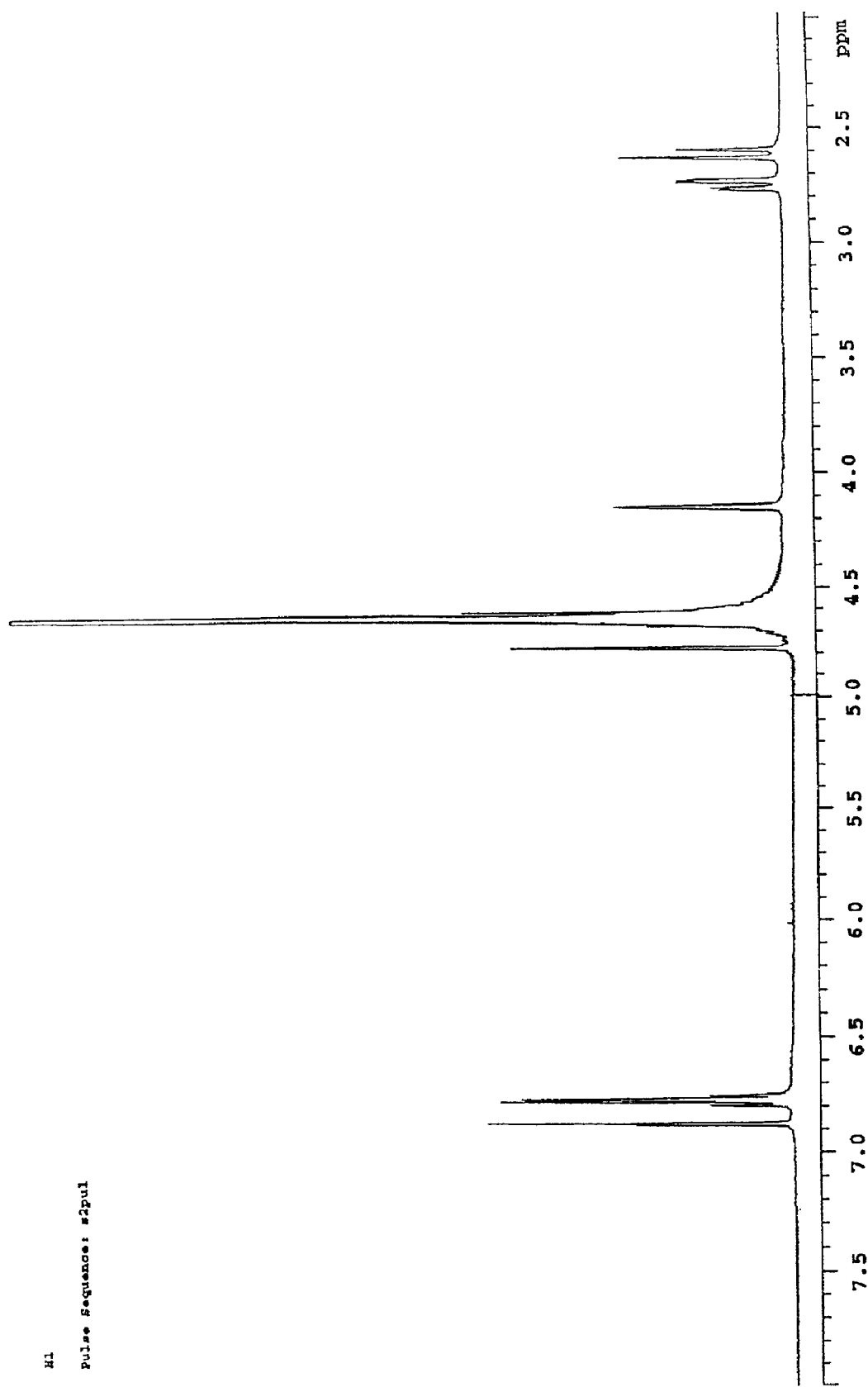
FIG. 21 is a Black and White Graph Demonstrating the $^1$H NMR Spectra of PTI-777-Compound J in $D_2O$ with 0.1% Triflouroacetic acid (TFA).

FIG. 21 is a Black and White Graph Demonstrating the $^1$H NMR Spectra of PTI-777-Compound J in D$_2$O with 0.1% Triflouroacetic acid (TFA).

Figure 22:
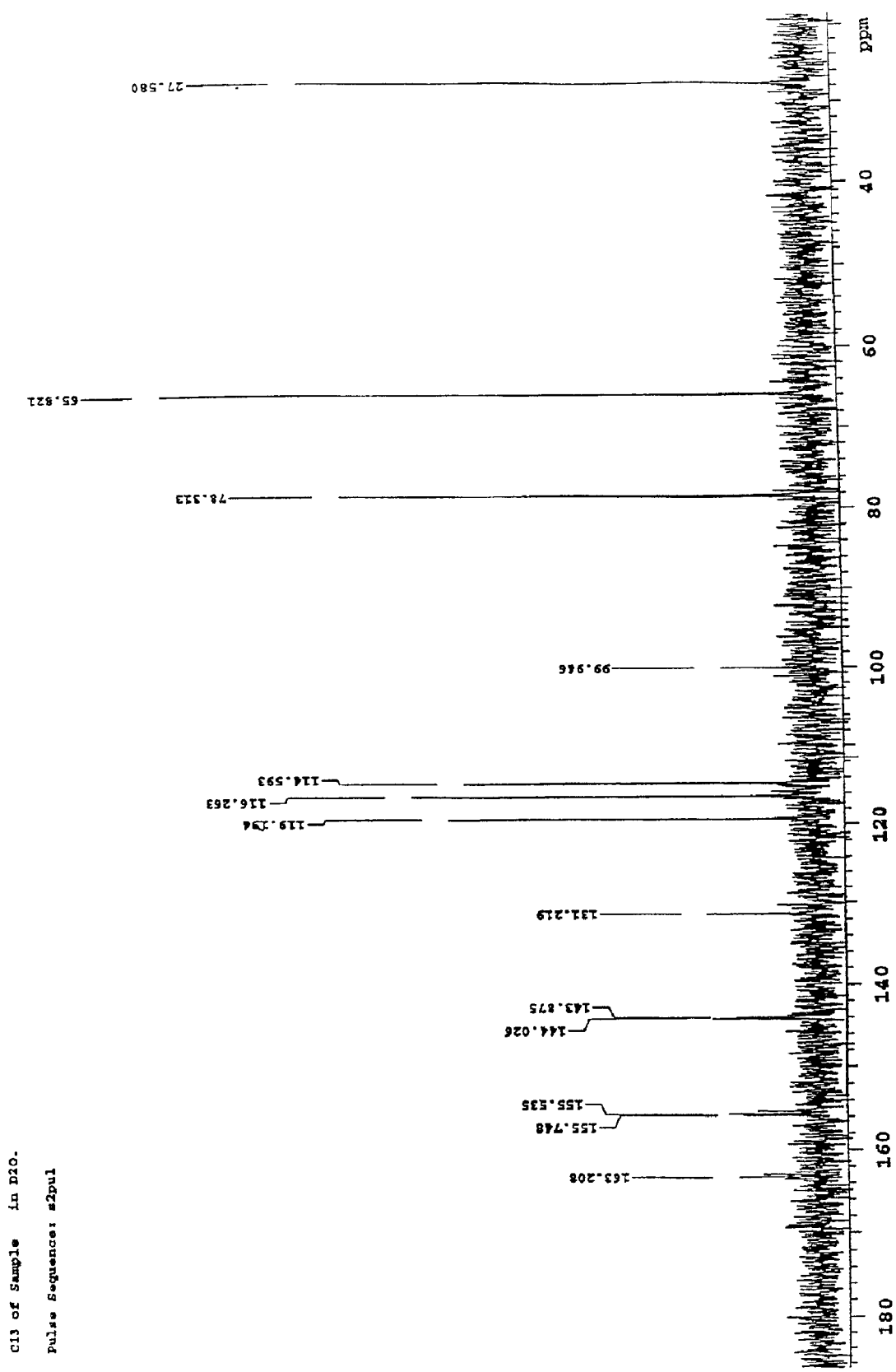
FIG. 22 is a Black and White Graph Demonstrating the $^{13}$C NMR Spectra of PTI-777-Compound J in $D_2O$ with 0.1% Triflouroacetic acid (TFA).

FIG. 22 is a Black and White Graph Demonstrating the $^{13}$C NMR Spectra of PTI-777-Compound J in D$_2$O with 0.1% Triflouroacetic acid (TFA).

Figure 23:
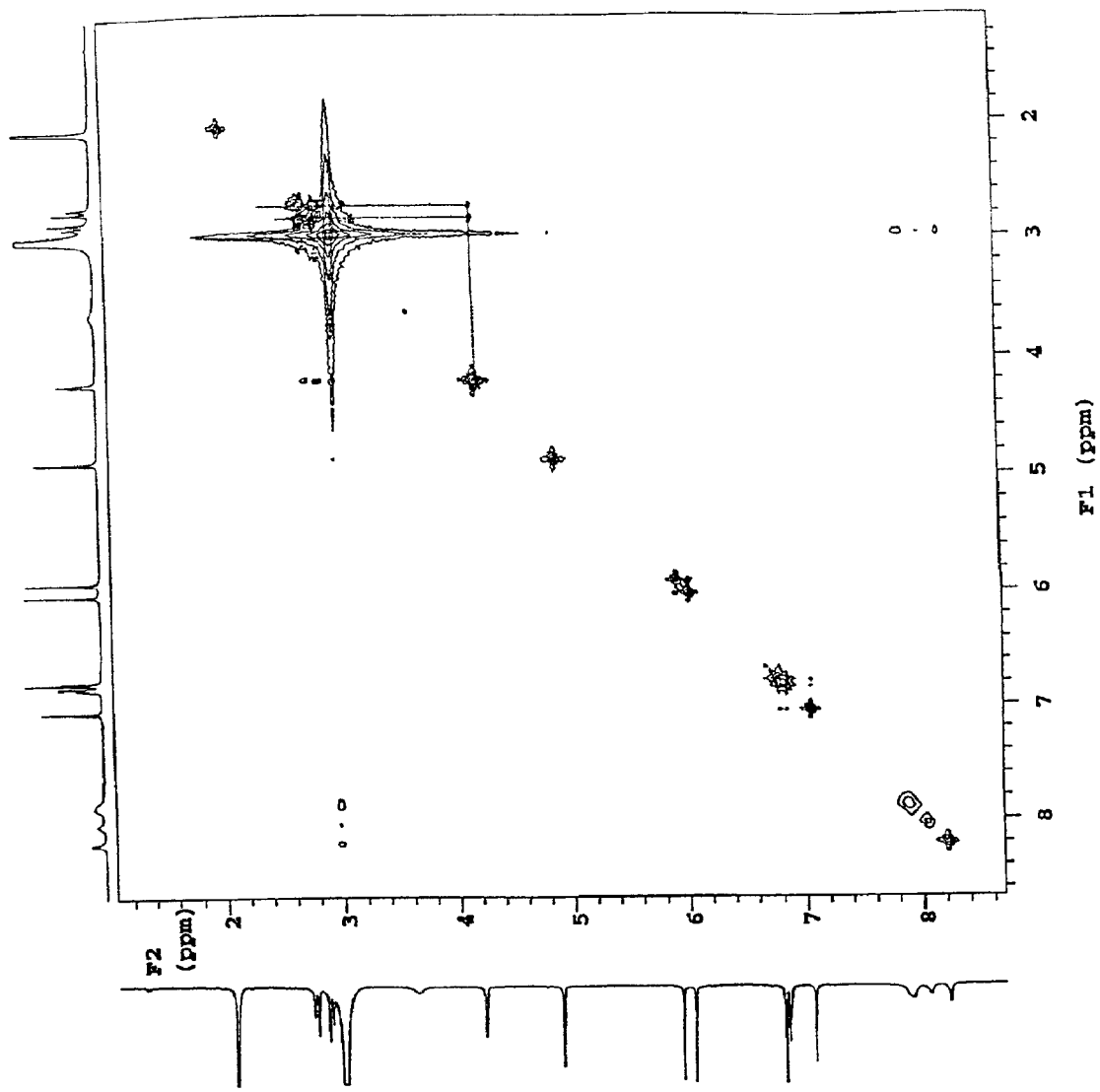
FIG. 23 is a Black and White Graph Demonstrating Correlation Spectroscopy (COSEY) of PTI-777-Compound J in $d_6$ Acetone.

FIG. 23 is a Black and White Graph Demonstrating Correlation Spectroscopy (COSEY) of PTI-777-Compound J in d$_6$ Acetone.

Figure 24A:
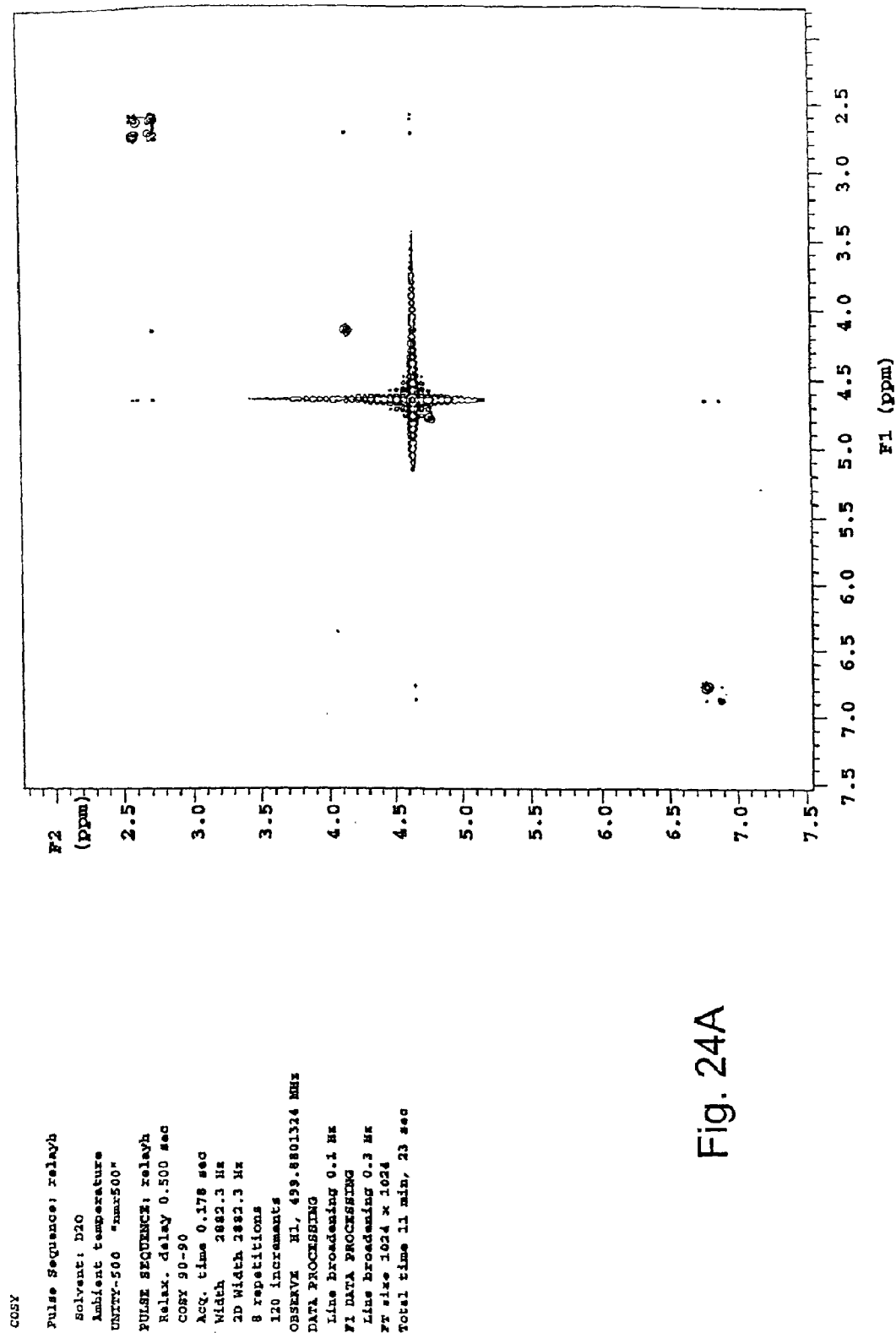
FIG. 24A is a Black and White Graph Demonstrating Correlation Spectroscopy (COSEY) of PTI-777-Compound J in acetified $D_2O$.

FIG. 24A is a Black and White Graph Demonstrating Correlation Spectroscopy (COSEY) of PTI-777-Compound J in acetified D$_2$O.

Figure 24B:
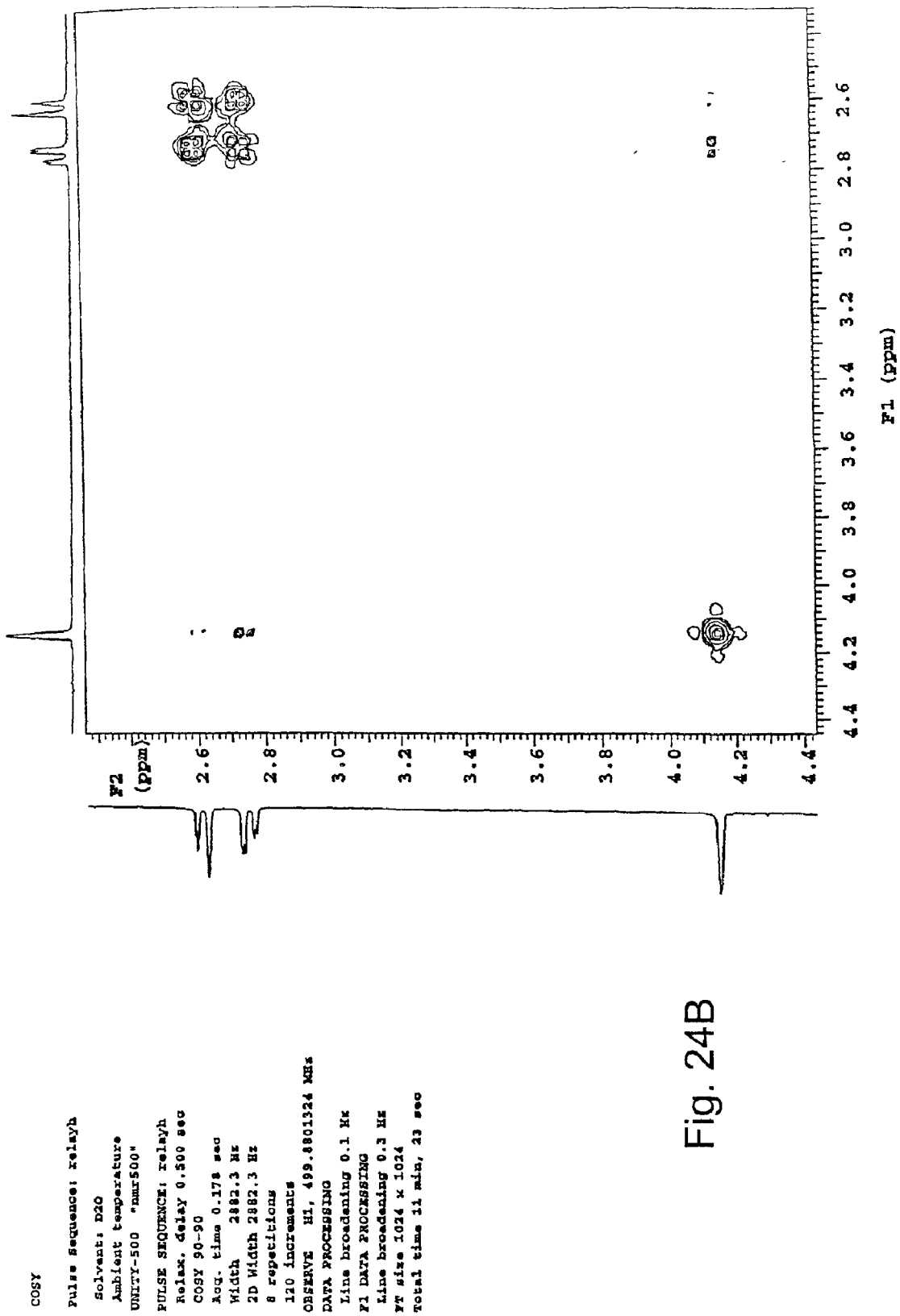
FIG. 24B is a Black and White Graph Demonstrating an Enlargement of the Upper Right Quadrant of the COSEY shown in FIG. 25A.

FIG. 24B is a Black and White Graph Demonstrating an Enlargement of the Upper Right Quadrant of the COSEY shown in FIG. 25A.

Figure 24C:
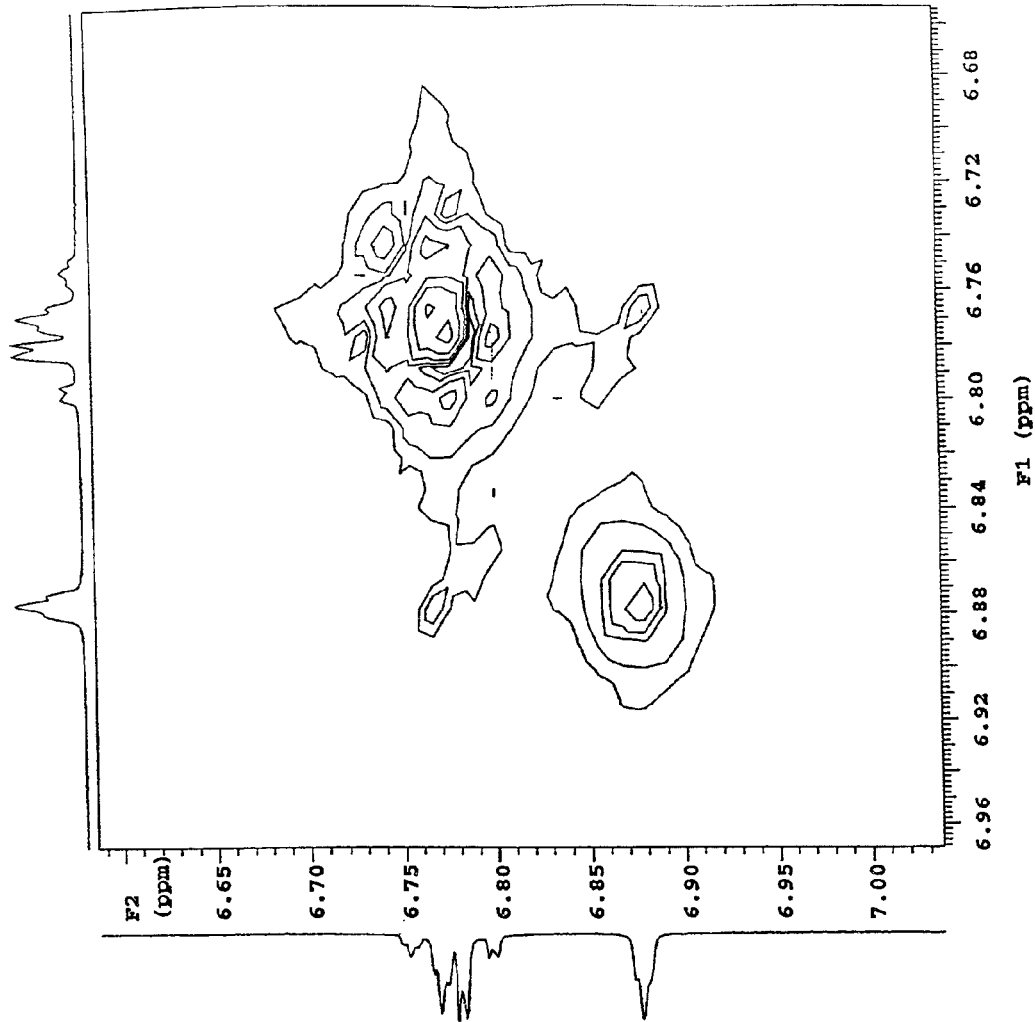
FIG. 24C is a Black and White Graph Demonstrating an Enlargement of the Lower Left Quadrant of the COSEY shown in FIG. 25A.

FIG. 24C is a Black and White Graph Demonstrating an Enlargement of the Lower Left Quadrant of the COSEY shown in FIG. 25A.

Figure 25:
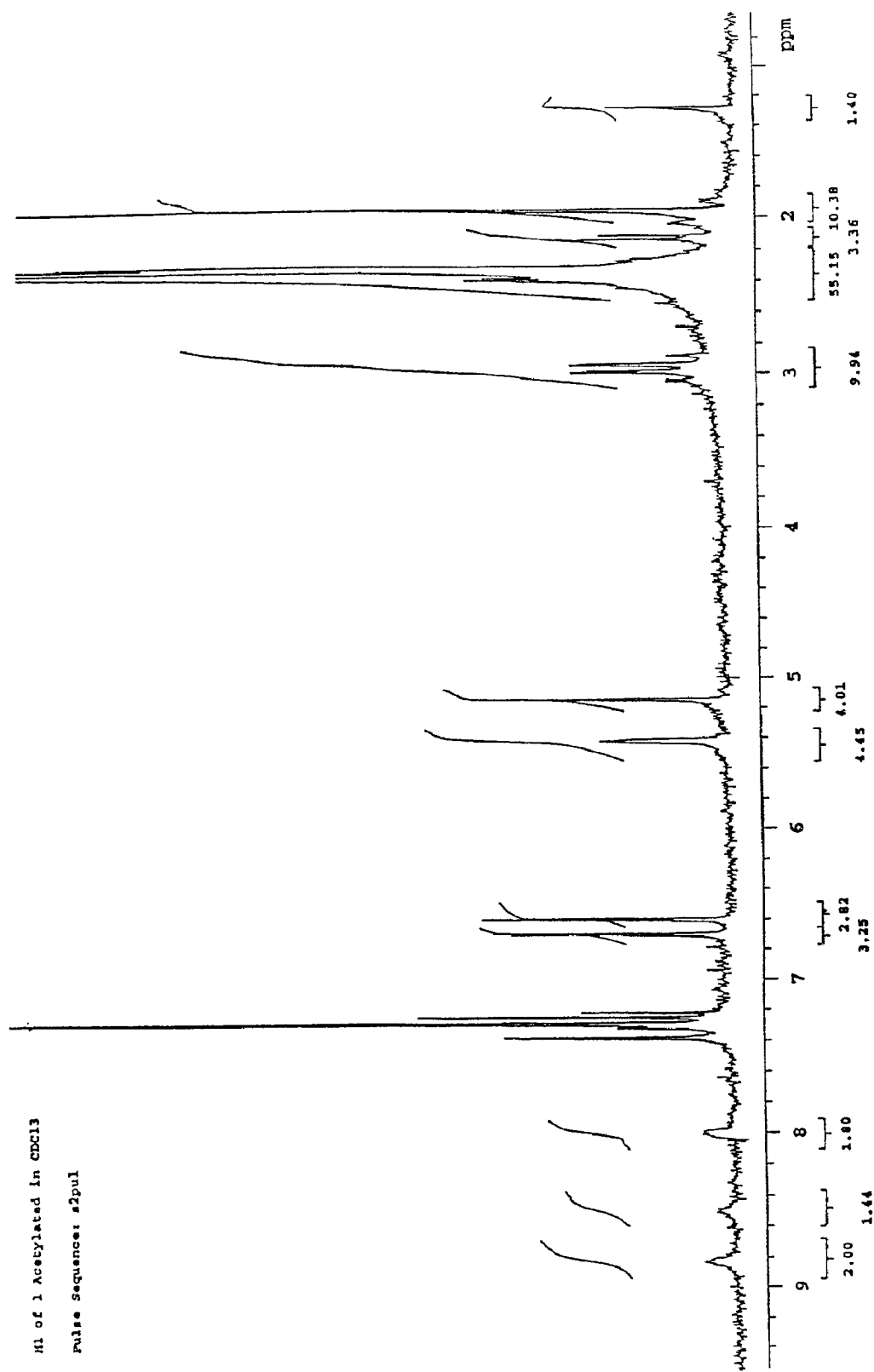
FIG. 25 is a Black and White Graph Demonstrating $^1$H NMR Spectra of PTI-777-Compound J that had been Acetylated.

FIG. 25 is a Black and White Graph Demonstrating $^1$H NMR Spectra of PTI-777 -Compound J that had been Acetylated (i.e. Pentaacetate Derivative of PTI-777-Compound J).

Figure 26:
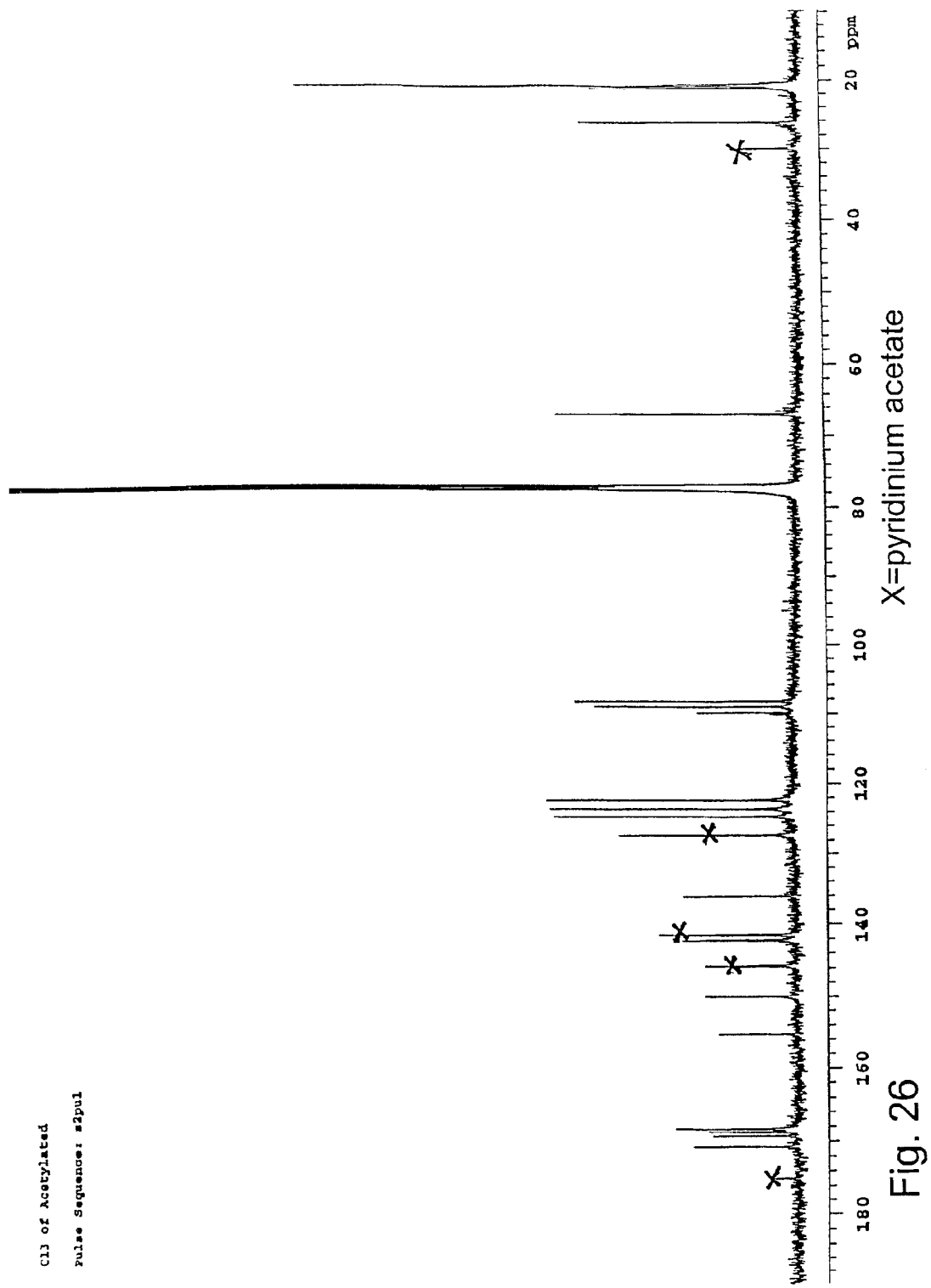
FIG. 26 is a Black and White Graph Demonstrating $^{13}$C NMR Spectra of PTI-777-Compound J that had been Acetylated.

FIG. 26 is a Black and White Graph Demonstrating $^{13}$C NMR Spectra of PTI-777 -Compound J that had been Acetylated (i.e. Pentaacetate Derivative of PTI-777-Compound J).

Figure 27:
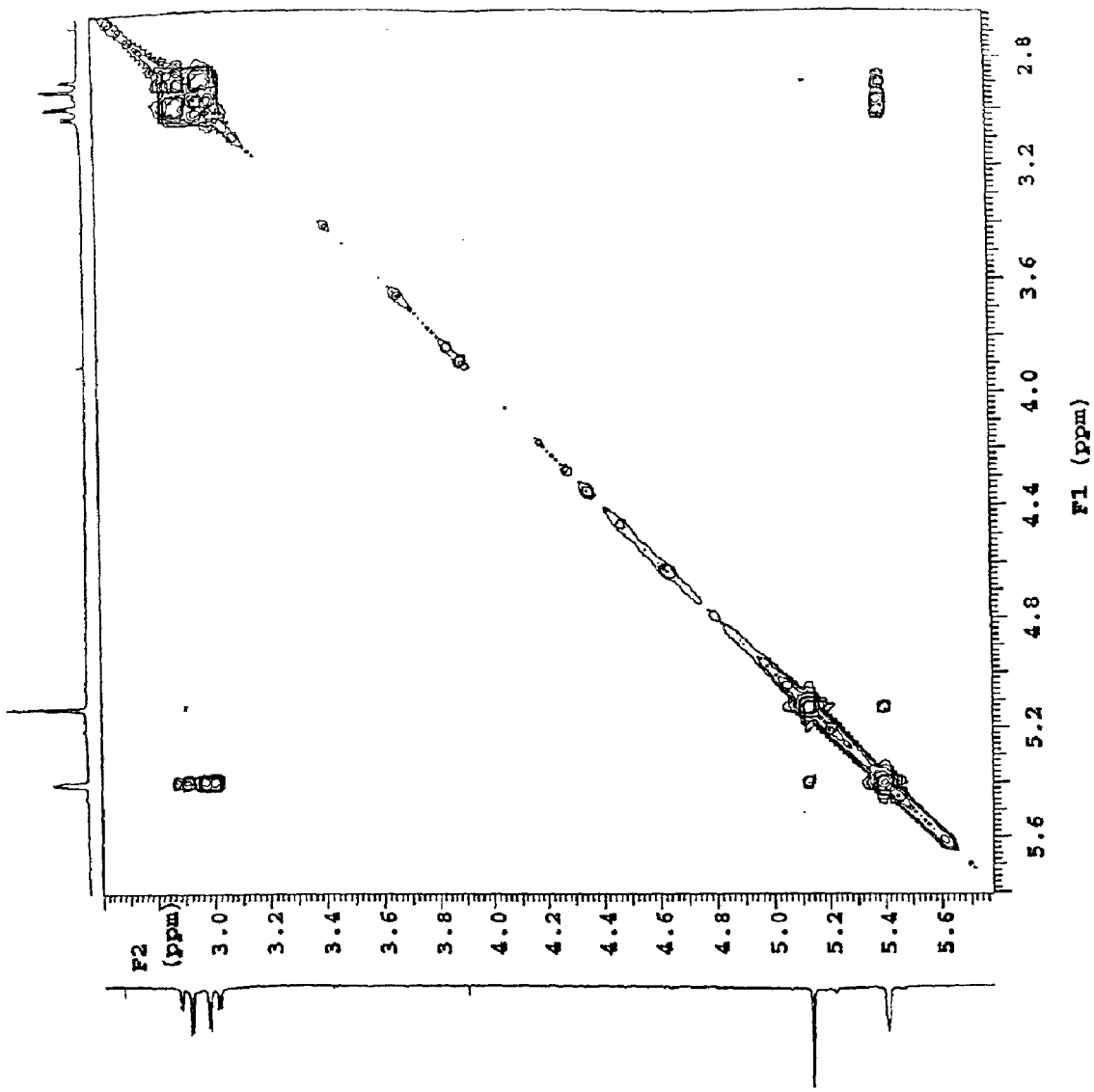
FIG. 27 is a Black and White Graph Demonstrating Correlation Spectroscopy (COSEY) of Pentaacetate Derivative of PTI-777-Compound J.

FIG. 27 is a Black and White Graph Demonstrating Correlation Spectroscopy (COSEY) of Pentaacetate Derivative of PTI-777-Compound J.

Figure 28A:
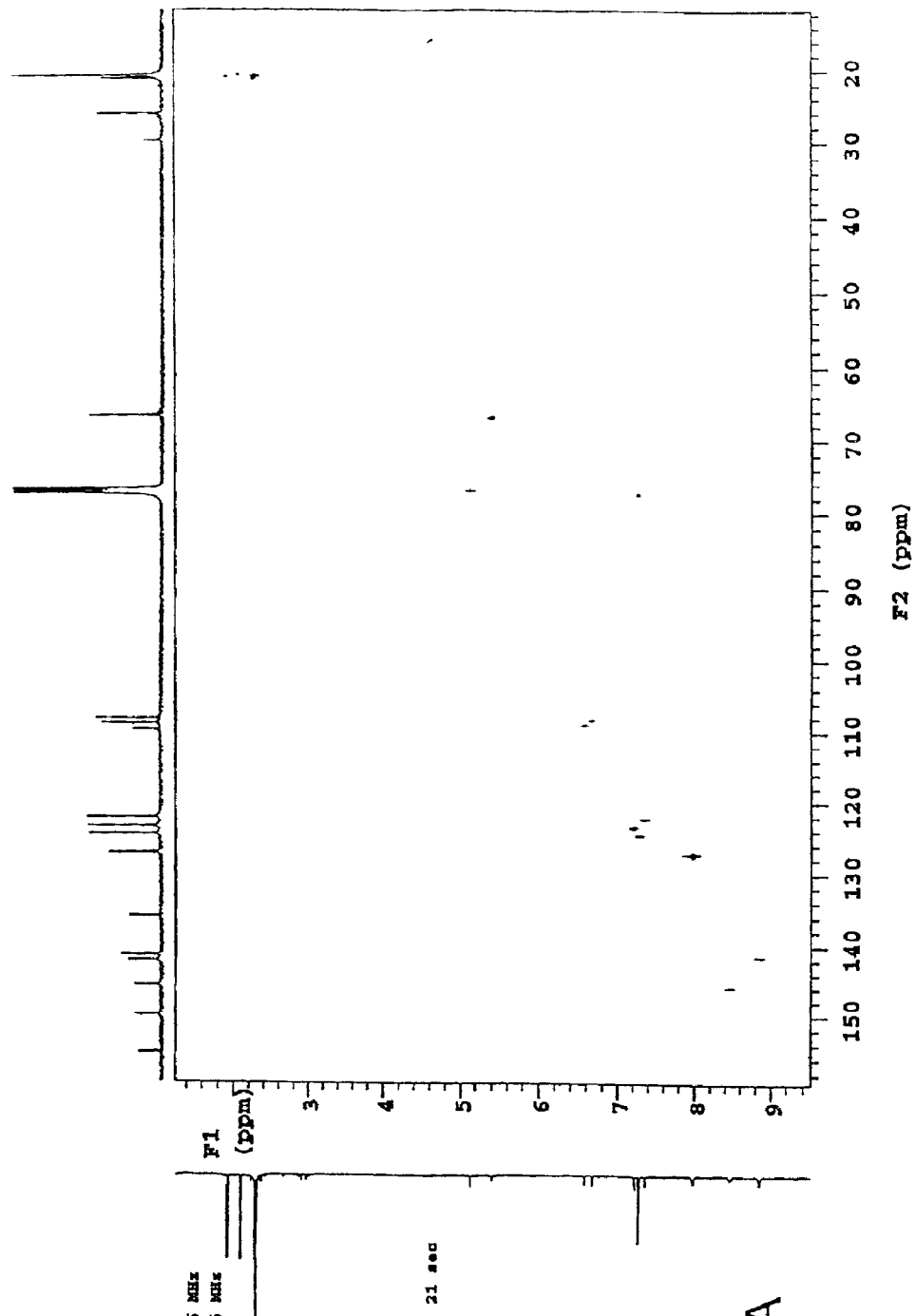
FIG. 28A is a Black and White Graph Demonstrating the Heteronuclear Correlation Spectroscopy (HECTOR) of the Pentaacetate Derivative of PTI-777-Compound J.

FIG. 28A is a Black and White Graph Demonstrating the Heteronuclear Correlation Spectroscopy (HECTOR) of the Pentaacetate Derivative of PTI-777-Compound J.

Figure 28B:
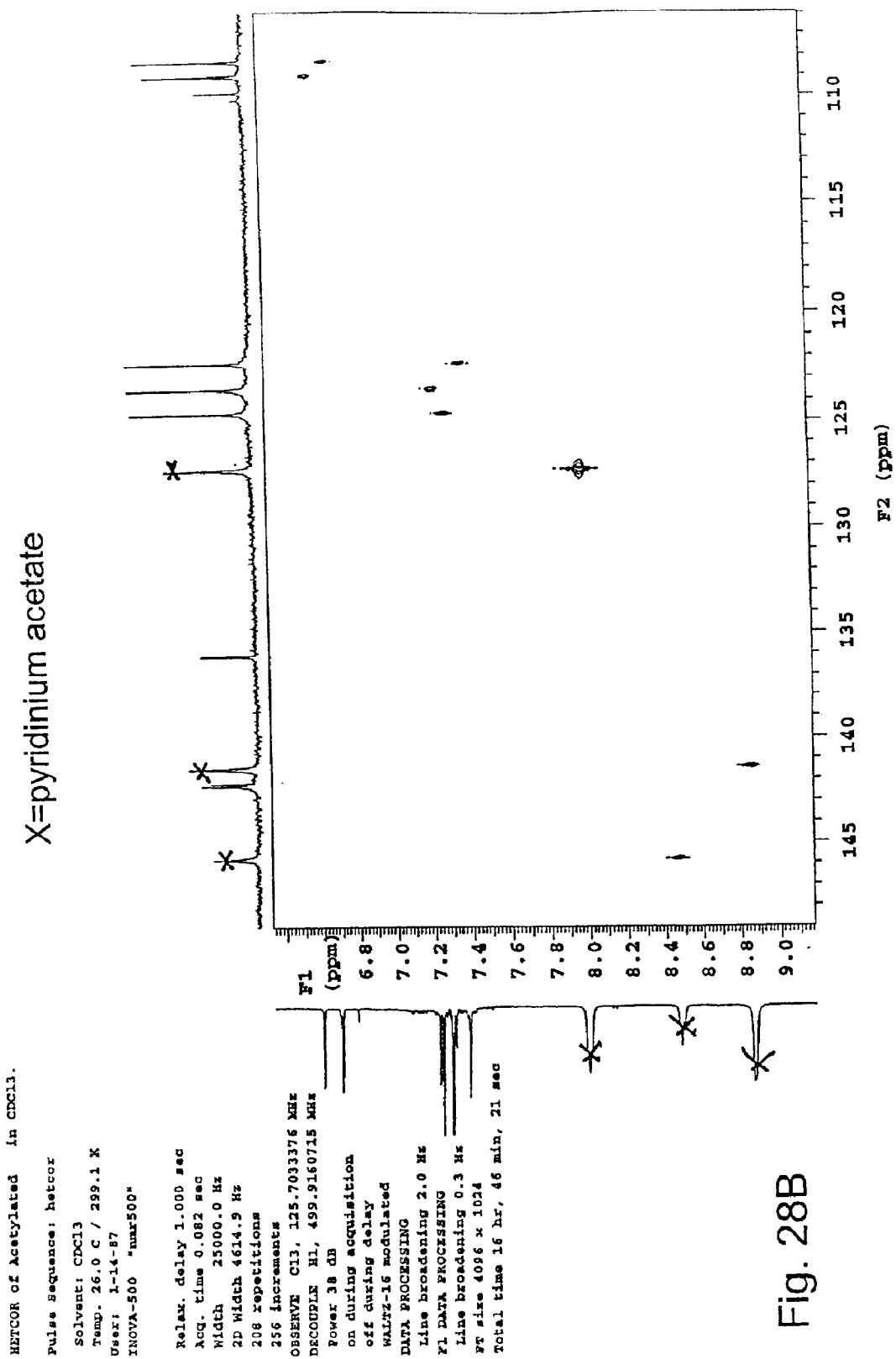
FIG. 28B is a Black and White Graph Demonstrating an Enlargement of the Aromatic Region of the HECTOR Spectra of the Pentaacetate Derivative of PTI-777-Compound J shown in FIG. 29A.

FIG. 28B is a Black and White Graph Demonstrating an Enlargement of the Aromatic Region of the HECTOR Spectra of the Pentaacetate Derivative of PTI-777-Compound J shown in FIG. 29A.

Figure 28C:
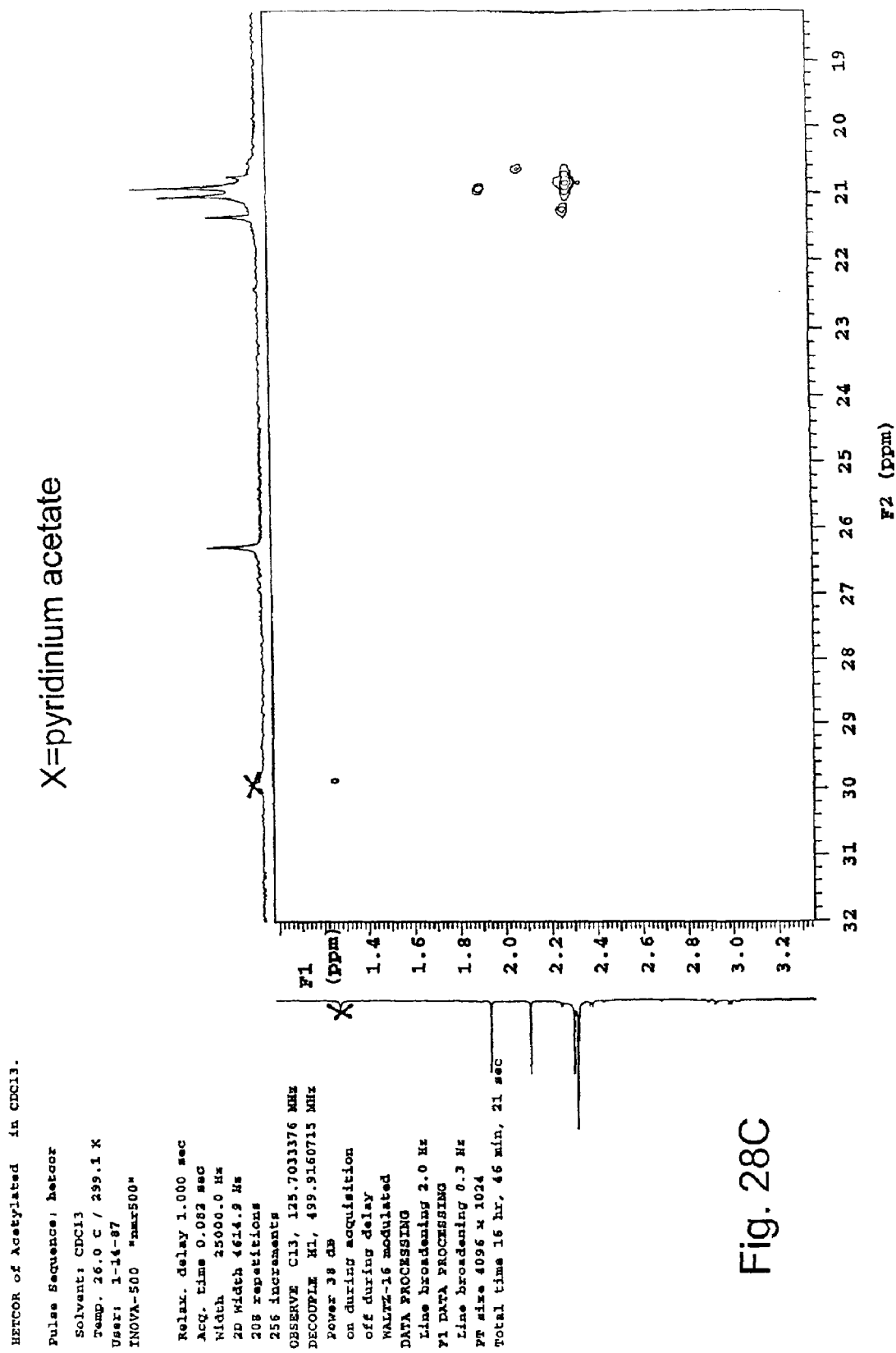
FIG. 28C is a Black and White Graph Demonstrating an Enlargement of the Methyl Region of the HECTOR Spectra of the Pentaacetate Derivative of PTI-777-Compound J shown in FIG. 29A.

FIG. 28C is a Black and White Graph Demonstrating an Enlargement of the Methyl Region of the HECTOR Spectra of the Pentaacetate Derivative of PTI-777-Compound J shown in FIG. 29A.

Figure 29:
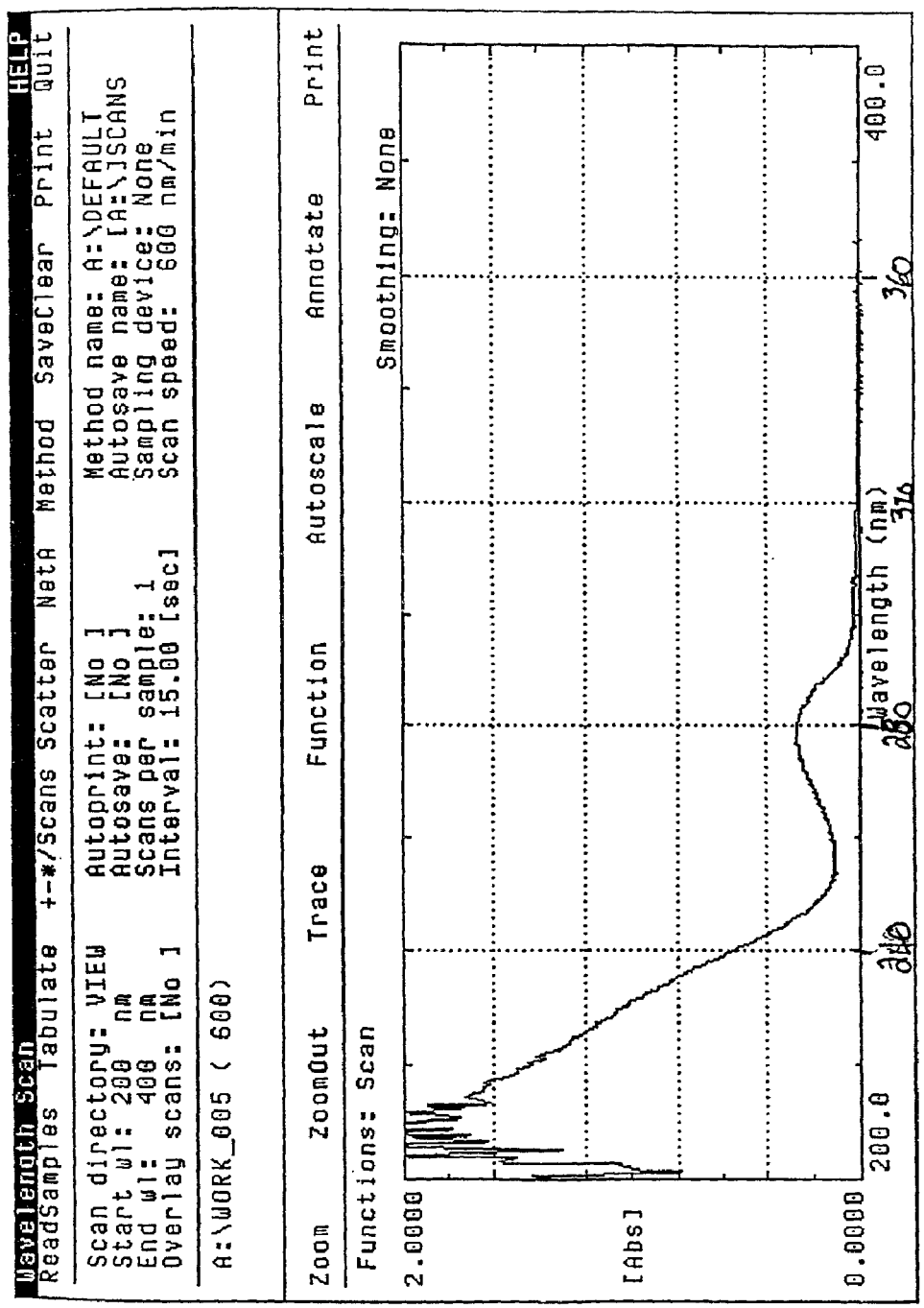
FIG. 29 is a Black and White Graph Demonstrating the Ultraviolet Spectrum of PTI-777-Compound J.

FIG. 29 is a Black and White Graph Demonstrating the Ultraviolet Spectrum of PTI-777-Compound J.

Figure 30:
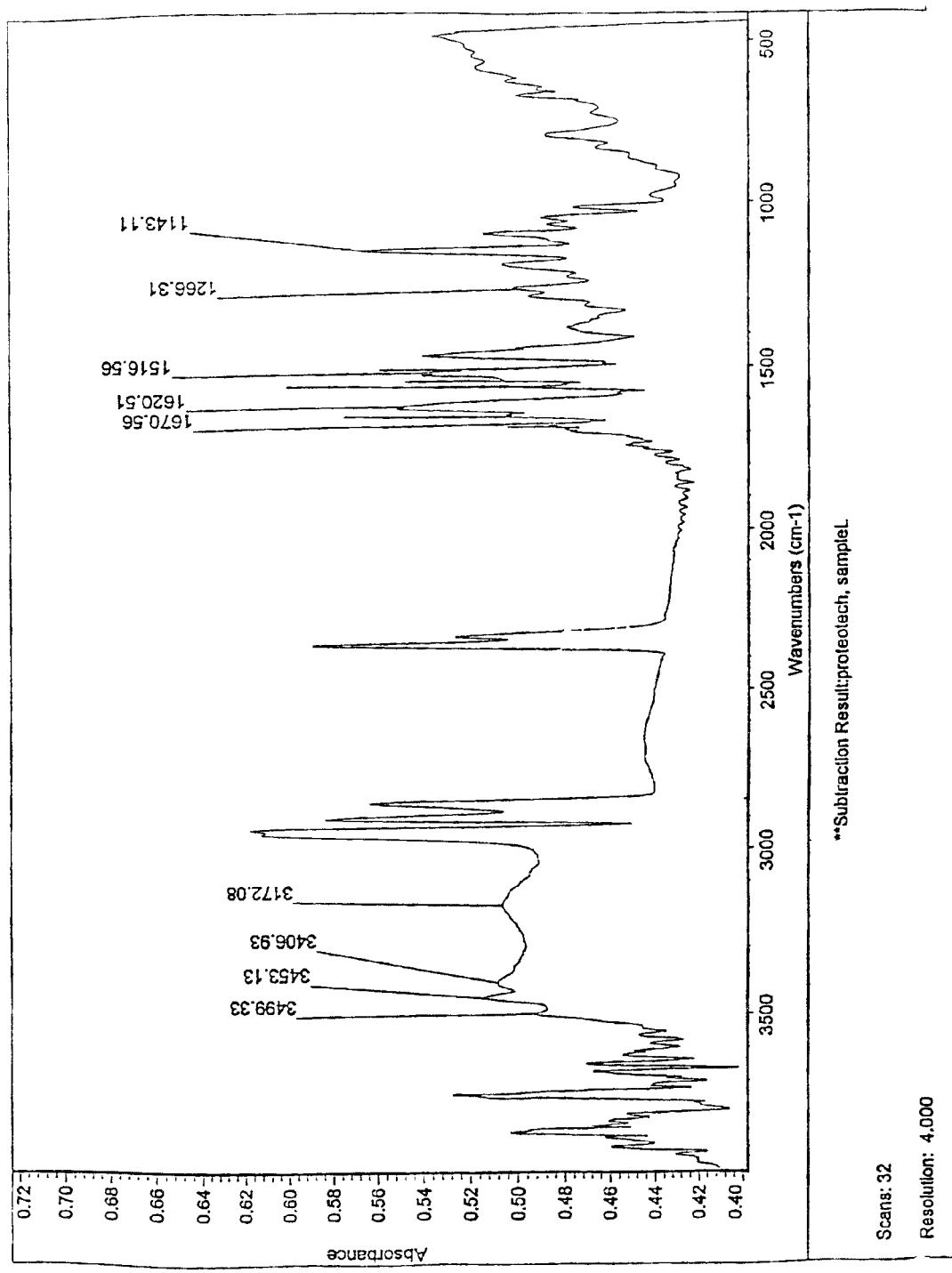
FIG. 30 is a Black and White Graph Demonstrating the Infrared Spectra of PTI-777-Compound J.

FIG. 30 is a Black and White Graph Demonstrating the Infrared Spectra of PTI-777-Compound J.

Figure 31A:
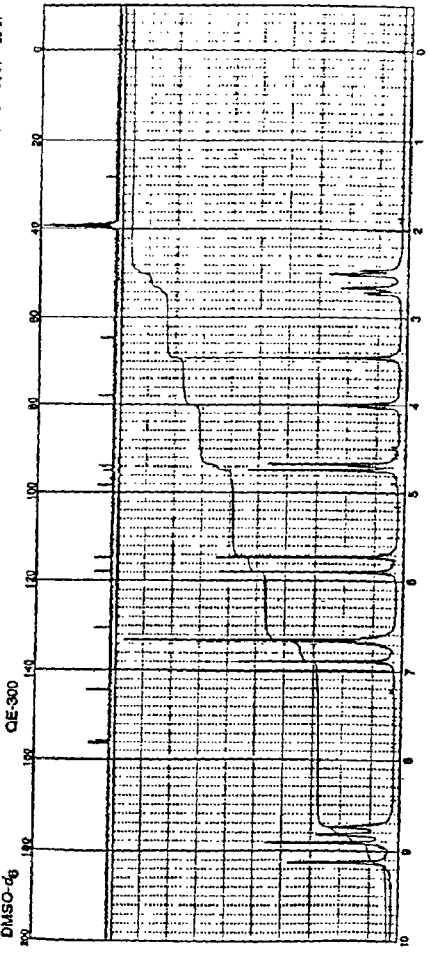
FIG. 31 are Black and White Graphs of the Published NMR Spectra of Epicatechin and Catechin Hydrate.
Figure 31B:
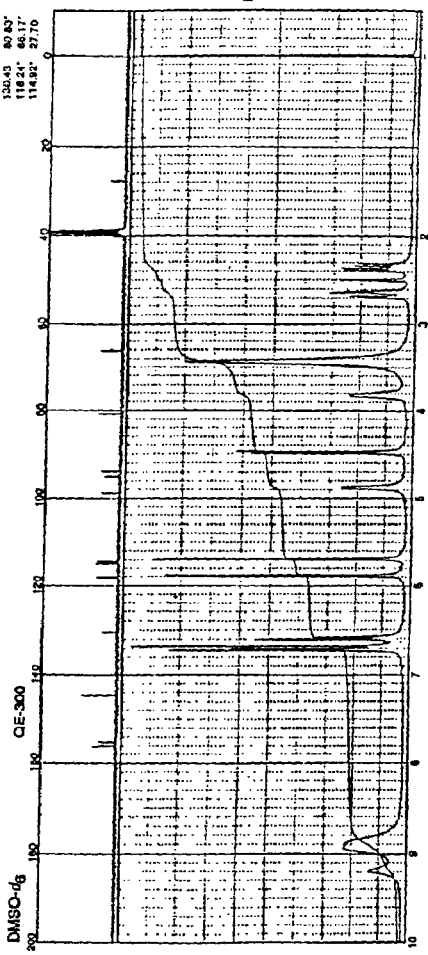

FIG. 31 are Black and White Graphs of the Published NMR Spectra of Epicatechin and Catechin Hydrate.

Figure 32A:
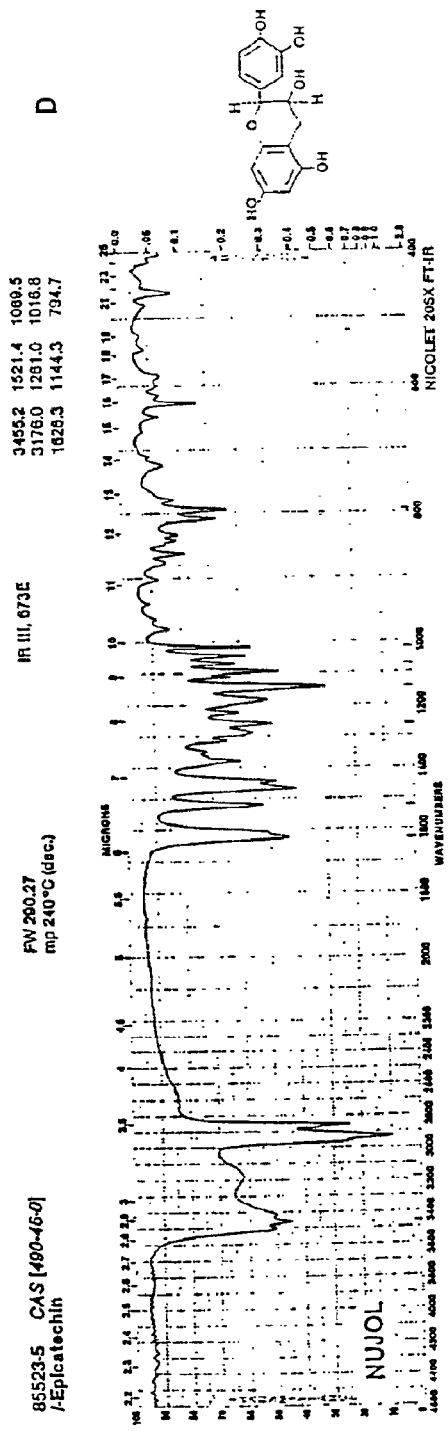
FIG. 32 are Black and White Graphs of the Published Infrared Spectra of Epicatechin and Catechin Hydrate.
Figure 32B:
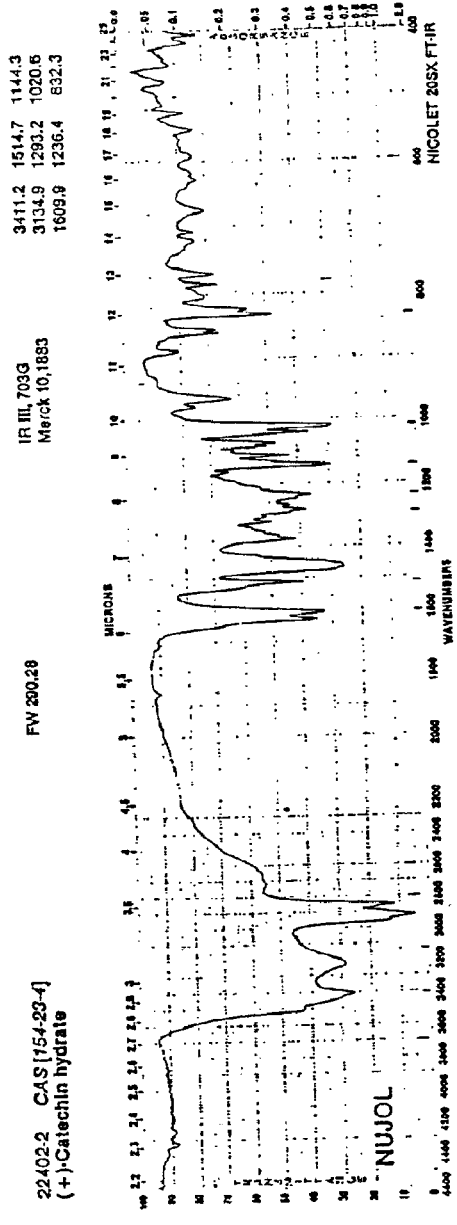

FIG. 32 are Black and White Graphs of the Published Infrared Spectra of Epicatechin and Catechin Hydrate.

Figure 33:
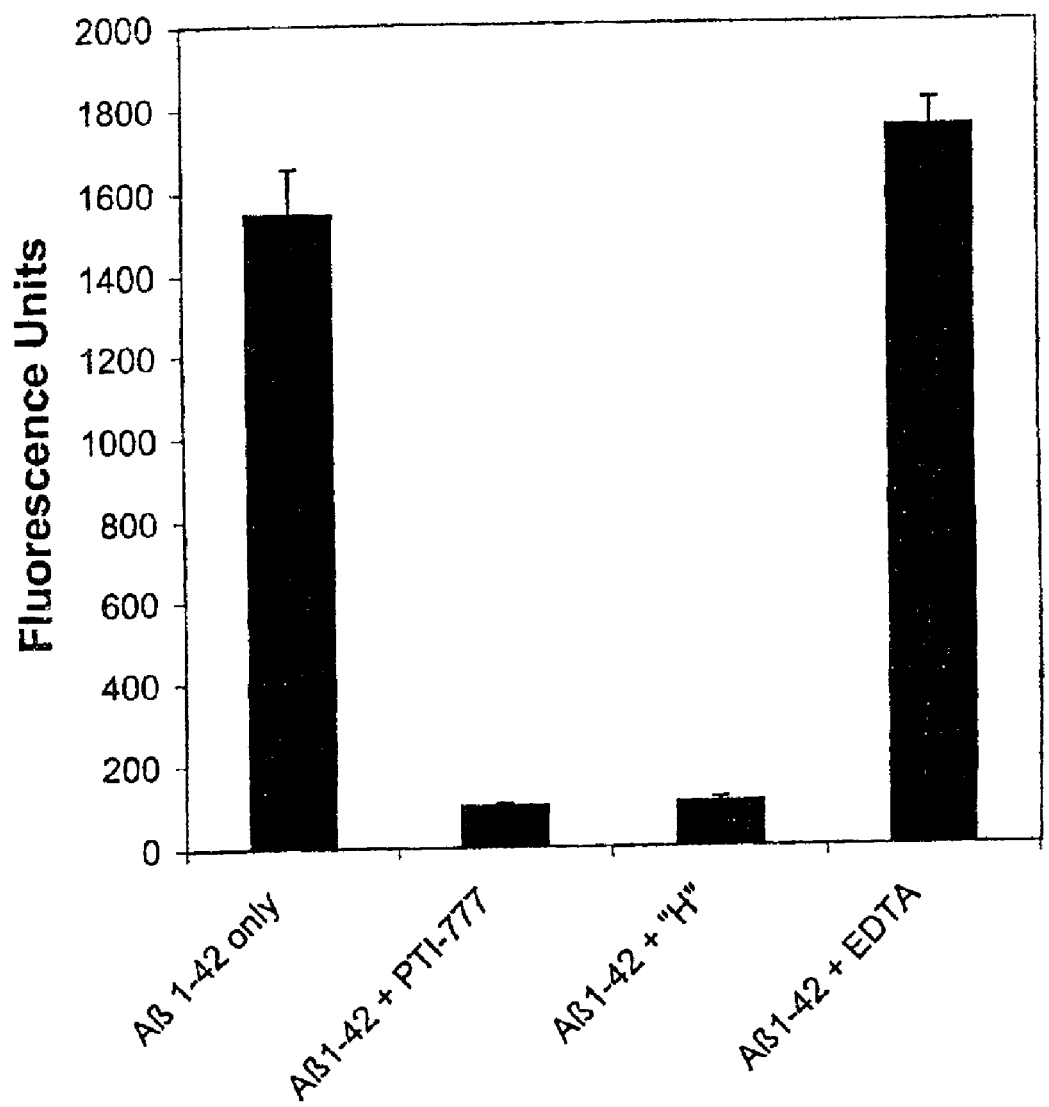
FIG. 33 is a Black and White Graph of a Thioflavin T Fluorometry Assay used to Determine the Efficacy of "Compound H" and PTI-777 on Disassembly/Dissolution of Pre-Formed Aβ 1-42 Fibrils.

FIG. 33 is a Black and White Graph of a Thioflavin T Fluorometry Assay used to Determine the Efficacy of "Compound H" and PTI-777 on Disassembly/Dissolution of Pre-Formed Aβ 1-42 Fibrils. Both "compound H: and PTI-777 cause a potent disassembly/disruption of pre-formed Aβ 1-42 fibrils.

Figure 34:
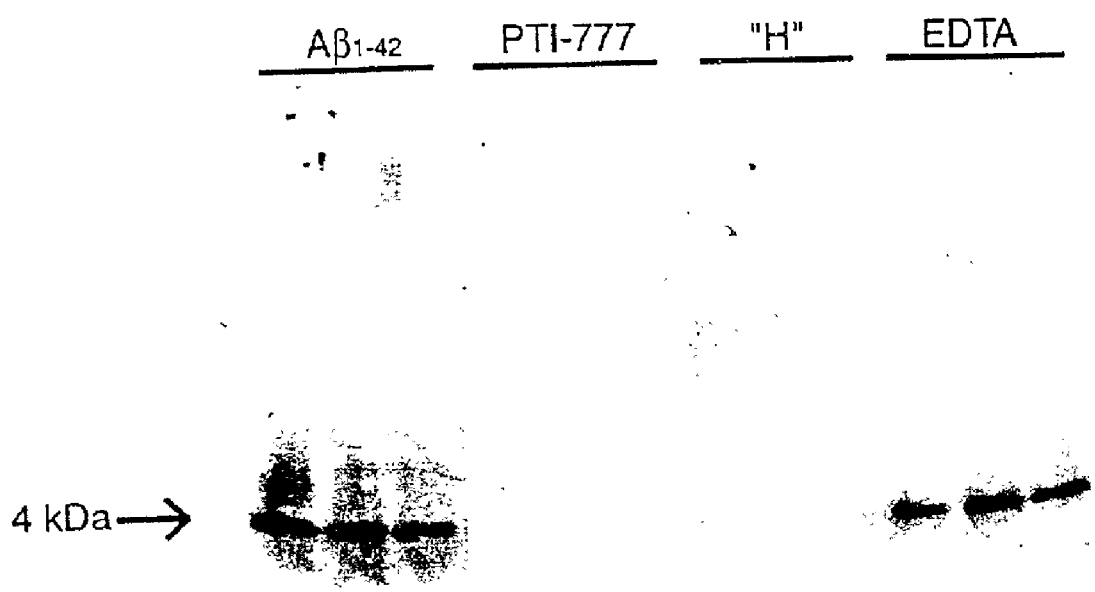
FIG. 34 is a Black and White Figure of a SDS-PAGE and Western Blot Further Demonstrating the Disruption of Aβ 1-42 Fibrils, Even in Monomeric Form by "Compound H" and PTI-777.

FIG. 34 is a Black and White Figure of a SDS-PAGE and Western Blot Further Demonstrating the Disruption of Aβ 1-42 Fibrils, Even in Monomeric Form by "Compound H" and PTI-777. 25 μM of pre-fibrillized Aβ 1-42 was incubated at 37° C. for 1 week either alone or in the presence of PTI-777 (1:1 wt/wt ratio), "compound H" (1:1 wt/wt ratio) or EDTA (1:1 wt/wt ratio). Following SDS-PAGE, Aβ was detected by ECL using anti-6E10 antibody. Aβ 1-42 monomers were not detected following the incubation of Aβ 1-42 with either PTI-777 or "compound H" suggesting that both were capable of causing a disappearance of monomeric Aβ 1-42.

EXAMPLES

The following examples are put forth so as to provide those with ordinary skill in the art with the disclosure and description of the composition, methods of isolation and use of amyloid inhibiting compounds derived from *Uncaria tomentosa* and related plants to inhibit amyloid fibril formation, and cause dissolution/disruption of preformed amyloid fibrils. However, it should not be construed that the invention is limited to these specific examples.

Example 1

Initial Isolation and Testing of Active Ingredients Derived from *Uncaria tomentosa*

Assay-guided affinity fractionation and high pressure liquid chromatography (HPLC) was used to separate and purify the major Aβ amyloid inhibitory active components present in *Uncaria tomentosa*. Several different separation techniques were evaluated to determine the best methodology to purify and test the active Aβ amyloid inhibiting components of *Uncaria tomentosa*. Initial studies utilized water extracts of *Uncaria tomentosa* applied to different Affi-Prep 10 gel columns derivatized with Tris-HCl, ammonia or ethanolamine. Methanol, ethanol or acetonitrile were found to effectively elute the *Uncaria tomentosa* active components from the column. It was also discovered that a Tris-HCl derivatized column was most effective in binding the Aβ amyloid inhibitory components of *Uncaria tomentosa* which suggested that the active ingredients may have affinity for both hydroxy (due to the Tris) and hydrophobic (due to the resin used) groups. In order to scale-up separation of the active components of *Uncaria tomentosa*, a Tris-acrylate column was prepared by rinsing 25 ml of Affi-Prep 10 gel (Biorad) with distilled water and incubating with 100 ml Tris-HCl (1 M, pH 8.0). The resulting material was packed into a 20 ml column (MT20, Biorad), attached to a 1100 series Hewlett Packard HPLC with diode array detector. The column was equilibrated at a flow rate of 0.5 ml/min with water. A water soluble extract prepared from 400 mg of lyophilized *Uncaria tomentosa* in 2 ml of distilled water was injected onto the Tris-Derivatized Affi-gel 10 column and eluted using the following profile: 0–10 min 100% water; 10–100 min, 0–100% acetonitrile, and 100–110 min, 100% acetonitrile. Fractions were collected every 4 minutes. Aliquots from fractions 1–22 (i.e. 4 mins to 84 mins) were then incubated with fibrillar Aβ 1-40 (FIG. 1) or Aβ 1-42 (not shown) for 2 hours (at a wt/wt ratio of 1:1) and tested for their ability to disrupt/disassemble pre-formed Aβ fibrils using Thioflavin T fluorometry as previously described (Castillo et al, *J. Neuroscience* 69:2452–2465, 1997). As shown in FIG. 1, fibrillar Aβ 1–1155 40 alone demonstrated a fluorescence of 836 +/-61 fluorescence units. Fractions 13–18 (i.e. 52–72 mins) demonstrated the greatest ability (from 60–75%) to disrupt/disassemble pre-formed Aβ 1-40 fibrils, as indicated by a marked lowering of fluorescence (FIG. 1). Similar results were obtained with pre-formed Aβ 1-42 fibrils (not shown). This study suggested that the most active Aβ amyloid inhibitory components present within the water soluble extract of *Uncaria tomentosa* (i.e. PTI-00703) were located within fractions 13–18.

Example 2

Purification of the Major Amyloid Inhibitory Components in the Water-Soluble Fraction of *Uncaria tomentosa* (PTI-777 Batch II Protocol)

Since our initial studies suggested that the PTI-00703 activity retained on the Tris-acrylate column may be due to the presence of hydroxy and hydrophobic groups, we implemented the use of a LH20 column (Pharmacia) as an initial column for larger scale preparations. LH20 is a carbohydrate-based resin derivatized in such a way that it acquires hydrophobic characteristics, and contains both hydroxy (from carbohydrates) and hydrophobic groups (from derivatization). When the water extract of *Uncaria tomentosa* (10 gms in 200 ml) was applied to a LH20 column, 100% of the Aβ amyloid inhibitory activity was retained by the column even after washing with 4 volumes of water. However, the Aβ amyloid inhibitory activity could be eluted with 3 volumes of 100% methanol. Materials retained on the column even following the 100% methanol wash were believed to primarily consist of tannic acids as previously described (Haegerman and Klucher, In: *Plant*

*Flavanoids in Biology and Medicine: Biochemical, Pharmacoloical and Structure-Activity Relationships*, Edited by V Cody, E. Middelton Jr., J. Harborne, Alan R. Liss, New York, 1986, pp.67–76). These tannin materials were later eluted with a 70% (v/v) acetone-water mixture applied during the column clean-up step. We found that fractions 13–18 (as described above), which consist of the major water-soluble active Aβ amyloid inhibitory components of *Uncaria tomentosa*, demonstrated similar HPLC profiles to the 100% methanol eluate of LH20. This finding indicated that regardless of whether a LH20 column or a Tris-HCl derivatized Affigel-10 column was used, similar components could be recovered. These components are collectively referred to as "PTI-777".

In our preparative protocol for isolation, purification and testing of the main active water-soluble components within *Uncaria tomentosa*, we scaled up use of the LH20 column for preparative purposes. To that end we used the following methodology for the extraction of "PTI-777 (Batch II)" (Table 1 outlines the protocol). 1 kg of *Uncaria tomentosa* was extracted using a 5 liter polypropylene container to which 4000 ml of methanol was added. Following mixing with a Barnant mixer, the extract was centrifuged at 2,500×g using a Beckman GS-6KR centrifuge for 30 minutes and the supernatant was collected. The insoluble material was extracted 3 more times in a similar manner and the combined supernatants (containing the active ingredients) were evaporated to dryness (or until 500 ml volume is reached) using a rotary evaporator at 50° C. (yield was 100 grams=~10% of starting material). The powdered extract (or 500 ml volume) was then washed 4 times with 300 ml of petroleum ether (to remove any lipids), and the ether layer was discarded. The methanol was then evaporated to dryness using a rotary evaporator at 50° C. The solid material was then extracted 5 times with 150 ml of distilled water. Each extraction was followed by centrifugation at 2,500× for 30 minutes. The combined supernatants (volume ~750 ml) were then lyophilized using a freeze-dryer. The resulting lyophilized water extract (yield was 50 grams=~5% of starting material) was dissolved in 500 ml of distilled water, and 50–100 ml portions (~3 grams) were applied to a 400 ml LH-20 column equilibrated with distilled water. The LH-20 column was then eluted with 1,100 ml of distilled water (~3 column volumes) and the amber/yellow, non-active fractions were discarded. The LH-20 column was then eluted with 1100 ml of 100% methanol (~3 column volumes) and a set of active fractions were collected and evaporated to dryness using a rotary evaporator. 12 grams of powdered extract was obtained (1.2% of the starting *Uncaria tomentosa* material) which was referred to as "PTI-777 (Batch II)".

Prior to additional purification of PTI-777 Batch II by reverse phase (C18) HPLC, the material was dissolved in distilled water (80 mg/ml) and applied 5 ml at a time to a 10 gm disposable C18 SPE column equilibrated in 95% water/5% acetonitrile/0.1% TFA (referred to as solvent A). The column was washed with 3 column bed volumes of solvent A and the eluate was discarded (which contained inactive components). The column was eluted with 3 column bed volumes of solvent A containing 12.5% solvent B (solvent B=95% acetonitrile/5% water/0.1% TFA). These fractions containing the Aβ amyloid inhibitory components were then lyophilized for further purification and analysis.

In an effort to isolate individual compounds responsible for the Aβ amyloid inhibitory activity of PTI-777 Batch II, preparative HPLC was used. For these studies, 50 mg of PTI-777 Batch II (prepared as described above) was injected multiple times into a Hewlett-Packard 1100 Series HPLC instrument with diode array detector, fitted with a 2.2 cm×25 cm Vydac 218TP1022 C18 reverse-phase column maintained at 25° C. and at a flow rate of 5 ml/min. The sample was eluted with the following solvent profile: 10% B for 0–20 mins., 10–100% B gradient for 20–30 mins., and 100–10% B gradient from 30–31 mins. where A=95% water/5% acetonitrile/0.1% TFA, and B=95% acetonitrile/5% water/0.1% TFA. Under these conditions, PTI-777 Batch II separated into 11 major components as revealed by uv/vis detection (diode array). Fractions containing 11 components were collected and labeled as follows: fraction G (16–17 mins), fraction F (17–18 mins), fraction H (19–20 mins), fraction I (21 mins), fraction J (22–23 mins), fraction $K_1$ (24 mins), fraction $K_2$ (25 mins), fraction L (26–27 mins), fraction M (28 mins), fraction N (29–30 mins) and fraction O (32–33 mins). The HPLC profile of PTI-777 Batch II is shown in FIG. 2.

TABLE 1

PTI-777 Batch II Isolation Protocol

| | |
|---|---|
| Step 1 | 1 kg of *Uncaria tomentosa* bark powder + 4000 ml methanol (mix) |
| Step 2 | Centrifuge for 30 minutes at 2,500 Xg |
| Step 3 | Collect supernatant - repeat centrifugation and supernatant collection steps 4 times |
| Step 4 | Evaporate to dryness or until volume is 500 ml at 50° C. |
| Step 5 | Wash with 300 ml of petroleum ether and discard ether layer (repeat 4 times) |
| Step 6 | Evaporate to dryness at 50° C. (100 g or ~10% of starting materials). Extract with 150 ml of distilled water, followed by centrifugation for 30 minutes at 2,500 Xg (repeat 5 times) |
| Step 7 | Lyophilize water extract (yield ~50 grams = ~5% of starting material) |
| Step 8 | Dissolve 50 g lyophilized water extract in 500 ml distilled water and apply 50–100 ml at a time on 400 ml LH-20 equilibrated with water |
| Step 9 | Elute with 1100 ml distilled water and discard |
| Step 10 | Elute with 1100 ml methanol, collect fractions and evaporate to dryness (these fractions contain mostly G, F, H, J, $K_1$, $K_2$, L, M, N, O and other more hydrophobic fractions) (yield ~12 grams = ~1.2% of starting material; these fractions are the most active against Aβ amyloid fibrillogenesis) |
| Step 11 | Clean up fractions obtained from step 10 as follows. Dissolve in water (80 mg/ml) and apply 5 ml at a time to a 10 gm of disposable C18 SPE column equilibrated in solvent A and wash with 3 volumes of solvent A and discard the eluate. Elute the clean fraction with 3 volumes of solvent A containing 12.5% solvent B. Lyophylize the corresponding fractions (~10 g from 1 kg). Where Solvent A = 95% water/5% acetonitrile/0.1% TFA, and Solvent B = 95% acetonitrile/5% water/0.1% TFA. |
| Step 12 | Fractionate fractions from step 11 on HPLC using 90 ml C18 reverse-phase HPLC column to isolate individual components (i.e. fractions F, G, H, I, J, $K_1$, $K_2$, L, M/N & O) |

Conditions; 50 mg/ml injections (in solvent A); 40 times; 5 mls/min flow rate; collect 5 ml fractions every 1 minute Gradient=10% B 0–20 minutes, 10–100% B20–30 minutes, 100–10% B30–31 minutes Run time=35 minutes Solvent A=95% water/5% acetonitrile/0.1% TFA Solvent B=95% acetonitrile/5% water/0.1% TFA Retention Times:

| | |
|---|---|
| Fraction G 16–17 minutes | Fraction $K_2$ 25 minutes |
| Fraction F 17–18 minutes | Fraction L 26–27 minutes |
| Fraction H 19–20 minutes | Fraction M 28 minutes |
| Fraction I 21 minutes | Fraction N 29–30 minutes |
| Fraction J 22–23 minutes | Fraction O 32–33 minutes |
| Fraction $K_1$ 24 minutes | |

Example 3

Modification of the PTI-777 Protocol to Reduce Fractions F, G, M, N and O (PTI-777 Batch I Protocol)

As outlined in Table 2, a second modified protocol (as described below) was also used to isolate the water-soluble amyloid inhibitory components from *Uncaria tomentosa*, and this protocol isolated a set of active fractions referred to as PTI-777 Batch I. PTI-777 Batch I components are identical to PTI-777 Batch II components, however, there is lesser amounts of fractions F, G, M, N, and O which are the yellowish components. Our data demonstrate that PTI-777 Batch I contains slightly more amyloid inhibitory activity than PTI-777 Batch II. For the isolation of PTI-777 Batch I the following methodology was used: 1 kg of *Uncaria tomentosa* was extracted using a 5 liter polypropylene container to which 4000 ml of methanol was added. Following mixing with a Barnant mixer, the extract was centrifuged at 2,500×g using a Beckman GS-6KR centrifuge for 30 minutes and the supernatant was collected. The insoluble material was extracted 3 more times in a similar manner and the combined supernatants (containing the active ingredients) were evaporated to dryness (or until volume is ~500 ml) using a rotary evaporator at 50° C. (yield was 100 grams=~10% of starting material). The powdered extract (or 500 ml volume) was then washed 4 times with 300 ml of petroleum ether (to remove any lipids), and the ether layer was discarded. The material was then evaporated to dryness using a rotary evaporator at 50° C. The solid material was then extracted 5 times with 150 ml of distilled water. Each extraction was followed by centrifugation at 2,500× for 30 minutes. The combined supernatants (volume ~750 ml) were then lyophilized using a freeze-dryer. The resulting lyophilized water extract (yield was 50 grams=~5% of starting material) was dissolved in 500 ml of distilled water, and 50–100 ml portions (~3 grams) were applied to a 400 ml LH-20 column equilibrated with distilled water. The LH-20 column was then eluted with 1,100 ml of distilled water (3 column volumes) and the amber/yellow, non-active fractions were discarded. The LH-20 column was then eluted with 1100 ml of 50% methanol/water and yellowish fractions were collected which contained mostly fractions F, G, M, N & O (yield was 6 grams=~0.6% of starting material). This added step separated away some of the less active components of PTI-777. The LH-20 column was then eluted with 1100 ml of 100% methanol (~3 column volumes) and a set of active fractions were collected (these fractions contained mostly H, J, $K_1$, $K_2$ and L) and evaporated to dryness using a rotary evaporator. 6 grams of powdered extract was obtained (0.6% of the starting *Uncaria tomentosa* material) which was referred to as "PTI-777 (Batch I)".

Prior to additional purification of PTI-777 Batch I by reverse phase (C18) HPLC, the material was dissolved in distilled water (80 mg/ml) and applied 5 ml at a time to a 10 gm disposable C18 SPE column equilibrated in 95% water/ 5% acetonitrile/0.1% TFA (referred to as solvent A). The column was washed with 3 volumes of solvent A and the eluate was discarded (which contained inactive components). The column was eluted with 3 volumes of solvent A containing 12.5% solvent B (solvent B=95% acetonitrile/5% water/0.1% TFA). These fractions containing the Aβ amyloid inhibitory components were then lyophilized for further purification and analysis.

As an alternative to the use of C18 SPE columns the PTI-777 material can also be further purified by flash chromatography techniques. As one example, 5 grams of post LH-20 lyophilized material containing PTI-777 was dissolved with 20 ml of distilled water. The solubilized solution was then transferred into a 50 ml disposable centrifuge tube and spun for 15 minutes on a centrifuge at ~6,000×g. A Varian Chromozone apparatus (set at about 85 psi) was then used at a flow rate setting of level 5, and then the column was equilibrated with 500 ml of solvent A (solvent A=95% water/5% acetonitrile/0.1% TFA). A 20 ml solution of the PTI-777 solublized material was loaded into a syringe and inserted into the sample port and loaded. With the flow rate setting at 5 or 6, the column was then washed with 500 ml of solvent A (equivalent to 3 column bed volumes) and the eluate which does not contain amyloid inhibitory activity, was discarded. The clean fraction containing the PTI-777 active fractions were then eluted with 550 ml of solvent A (equivalent to close to 3 column bed volumes) containing 12% solvent B (solvent B=95% acetonitrile/5% water/0.1% TFA). The first 50 ml of the eluate was discarded. The PTI-777 fraction was collected into a 1 liter pyrex bottle for further purification as described below.

In an effort to isolate individual compounds responsible for the Aβ amyloid inhibitory activity of PTI-777 Batch I, preparative HPLC was used. For these studies, 50 mg of PTI-777 Batch I (prepared by methods as described above) was injected multiple times into a Hewlett-Packard 1100 Series HPLC instrument with diode array detector, fitted with a 2.2 cm×25 cm Vydac 218TP1022 C18 reverse-phase column (95 ml) maintained at 25° C. and at a flow rate of 5 ml/min. The sample was eluted with the following solvent profile: 10% B for 0-20 mins., 10–100% B gradient for 20–30 mins., and 100–10% B gradient from 30–31 mins. where A=95% water/5% acetonitrile/0.1% TFA, and B=95% acetonitrile/5% water/0.1%TFA. Under these conditions, PTI-777 Batch I separated into components (FIG. 5), as revealed by uv/vis detection (diode array). These fractions were collected and labeled as follows: fraction G (13–14 mins), fraction F (15–16 mins), fraction H (17–20 mins), fraction 1 (21 mins), fraction J (22–23 mins), fraction $K_1$ (24 mins), fraction $K_2$ (25 mins), fraction L (26–27 mins), fraction M (27–28 mins), and fraction N (28–29 mins). This modification led to the reduction of fractions F, G, M, N and O. The HPLC profile of PTI-777 Batch I is shown in FIG. 3.

TABLE 2

| PTI-777 Batch I Isolation Protocol | |
|---|---|
| Step 1 | 1 kg of *Uncaria tomentosa* bark powder + 4000 ml methanol (mix) |
| Step 2 | Centrifuge for 30 minutes at 2,500 Xg |
| Step 3 | Collect supernatant - repeat centrifugation and supernatant collection steps 4 times |
| Step 4 | Evaporate to dryness or until volume is 500 ml at 50° C. |
| Step 5 | Wash with 300 ml of petroleum ether and discard ether layer (repeat 4 times) |
| Step 6 | Evaporate to dryness at 50° C. (100 g or ~10% of starting materials). Extract with 150 ml of distilled water, followed by centrifugation for 30 minutes at 2,500 Xg (repeat 5 times) |
| Step 7 | Lyophilize water extract (yield ~50 grams = ~5% of starting material) |
| Step 8 | Dissolve 50 g lyophilized water extract in 500 ml water and apply 50–100 ml at a time on 400 ml LH-20 equilibrated with water |
| Step 9 | Elute with 1100 ml water and discard |
| Step 9A | Elute with 1100 ml of 50% methanol/distilled water and collect fractions (these fractions contain mostly F, G, M and N) (yield ~6 grams = ~0.6% of starting material) |

TABLE 2-continued

PTI-777 Batch I Isolation Protocol

Step 10  Elute with 1100 ml methanol and collect fractions (these fractions contain mostly H, J, K$_1$, K$_2$, L and other more hydrophobic fractions) (yield ~6 gram = ~0.6% of starting material; these fractions are the most active against Aβ amyloid fibrillogenesis)
Step 11  Clean up fractions obtained from steps 9a and 10 as follows. Dissolve in water (80 mg/ml) and apply 5 ml at a time to a 10 gm of disposable C18 SPE column equilibrated in solvent A and wash with 3 volumes of solvent A and discard the eluate. Elute the clean fraction with 3 volumes of solvent A containing 12.5% solvent B. Lyophilize the corresponding fractions (~5 g each obtained from steps 9A and 10). Where, Solvent A = 95% water/5% acetonitrile/ 0.1% TFA, and Solvent B = 95% acetonitrile/5% water/0.1% TFA.
Step 12  Fractionate fractions from step 11 (which consists of two separate fractions) on HPLC using 90 ml C18 reverse-phase HPLC column to isolate individual components.

Conditions; 50 mg/ml (in solvent A) injections; 40 times; 5 mls/min flow rate; collect 5 ml fractions every 1 minute
Gradient=10% B0–20 minutes, 10–100% B20–30 minutes, 100–10% B30–31 minutes
Run time=35 minutes
Solvent A=95% water/5% acetonitrile/0.1% TFA
Solvent B=95% acetonitrile/5% water/0.1% TFA

| Retention Times: | |
|---|---|
| Fraction G 13–14 minutes | Fraction K$_1$ 24 minutes |
| Fraction F 15–16 minutes | Fraction K$_2$ 25 minutes |
| Fraction H 17–20 minutes | Fraction L 26–27 minutes |
| Fraction I 21 minutes | Fraction M 27–28 minutes |
| Fraction J 22–23 minutes | Fraction N 28–29 minutes |

Example 4

Analytical/Semi-Preparative Fractionation

Fractions from step 11 (see Table 2 above) can also be analyzed by HPLC using a C18 reverse-phase HPLC column (10×250 mm; 20 ml resin) to fractionate the various components including fractions F, G, H, I, J, K$_1$, K$_2$, L, M/N and O, as well as more hydrophobic components. Using these conditions ~50 μg in solvent A was fractionated using the HPLC apparatus at a flow rate of ~1.5 ml/minute. The gradient run was 10% B from 0 to 20 minutes, 10%–100% B gradient from 20 to 30 minutes, and 100%–10% B gradient from 30 to 31 minutes. Solvent B=95% acetonitrile/ 5% water/0.1% TFA. Using this method, the retention times of the various fractions were as follows: Fraction G (12–13 minutes), Fraction F (13–14 minutes), Fraction H (15 minutes), Fraction I (16 minutes), Fraction J (18–19 minutes), Fraction K$_1$ (20 minutes), Fraction K$_2$ (21 minutes), Fraction L (21–23 minutes), Fraction M (23 minutes), Fraction N (24 minutes) and Fraction O (26–27 minutes).

Example 5

Scale-Up Procedures for the Isolation of the Amyloid Inhibitory Components of *Uncaria tomentosa*

Based on our work 1 kg of *Uncaria tomentosa* (i.e. Cat's claw) bark powder is expected to yield 300–500 mg of each of the purified amyloid inhibitory components from PTI-777 (i.e. fractions G through O). Scale up procedures may be utilized for the isolation of PTI-777 and its individual components. For these procedures the *Uncaria tomentosa* bark powder can be extracted in 1 kg batches as described in detail in Examples 2 and 3. The only difference in procedure is that the centrifugation steps can take place at higher speeds/centrifugation force (i.e. ×20,000 g instead of ×2,500 g) using a Sorvall Discovery 100S or equivalent ultracentrifuge. Methanol eluted fractions from the LH-20 column are collected and will contain the PTI-777 fractions. Prior to preparative HPLC, the PTI-777 containing fractions (80 mg/ml) are applied 5 ml at a time to a 10 gm disposable C18 SPE column equilibrated in 95% water/5% acetonitrile/ 0.1% TFA (i.e. solvent A). The column is then washed with 3 volumes of solvent A and the resulting eluate discarded (contains remaining inactive components). The material containing PTI-777 is then eluted from the column with 3 volumes of solvent mixture comprising 87.5% A and 12.5% solvent B (solvent B=95% 71288 acetonitrile/5% water/ 0.1% TFA) and lyophilized prior to further purification and analysis.

Preparative HPLC is used to separate the PTI-777 mixture and obtain pure samples of the compounds isolated from the mixture. For faster and scale-up preparations, samples of PTI-777 (1 g in 5–10 ml in solvent A) are injected onto a 4.14 cm×25 cm Varian Dynamax C-18 reverse phase column fitted to a Varian Prostar 215 solvent delivery system, and a Varian model 320 UV-Vis detector. The separation is carried out at ambient temperature, a flow rate of 50 ml/min, and UV detection at 230 nm. The solvent gradient profile is as follows:0–4 min, 25% B; 4–11 min, 25–30% B; 11–14 min, 30–90% B; 14–17 min, 90% B; and 17–19 min, 90–25% B; where A is distilled water with 0.1% TFA and B is methanol with 0.1% TFA. Based on our work, these modified HPLC conditions will also result in the separation and purification of the 11 major fractions (G–O incl. K$_1$ and K$_2$) previously isolated from PTI-777. The fractions obtained under these procedures can be correlated with the original fractions by HPLC under conditions described in the Examples above. Final purification of PTI-777 individual components within each fraction may require additional HPLC to separate each of the major compounds within each fraction, from any minor components that may be present. The major components of each fraction (which usually represent 90% of the material) are isolated by the pooling (and drying) of fractions comprised of a single major peak when viewed at 210 nm on HPLC. The resulting pure material can be used for in vitro/in vivo testing and structural elucidation as described herein. To assess the purity of individual major PTI-777 components HPLC/diode array detection is used as well as mass spectroscopy and nuclear magnetic resonance (NMR) spectroscopy.

Example 6

In Vitro Testing of Individual Fractions within PTI-777 for Aβ Amyloid Inhibitory Activity The bioactivities of PTI-777 (either derived from Batch I or Batch II) and its isolated individual fractions (i.e. fractions F through O) were evaluated in a number of different in vitro assays. Testing included the use of Thioflavin T fluorometry, Congo red staining assays, solid phase binding immunoassays (for analysis of inhibition of Aβ—Aβ and Aβ-glycosaminoglycan interactions) and negative stain electron microscopy to assess the effects on inhibition of Aβ fibril formation and growth, interactions with specific glycosaminoglycans, as well as ability to disrupt/disassemble pre-formed Aβ fibrils. In most experiments, individual isolated fractions of PTI-777 were directly compared to a water extract of *Uncaria tomentosa* (i.e. PTI-00703), PTI-777 (containing the mixture of fractions F through O), and the major oxindole alkaloids isolated from *Uncaria tomentosa* and thought to contain important bioactivity as previously described in two US patents (U.S. Pat. No. 4,844,901 and U.S. Pat. No. 4,940,725). These oxindole alkaloids are believed to provide a general boost to the immune system as well as have a profound effect on the ability of white blood cells and macrophages to phagocytize harmful microorganisms and foreign matter (U.S. Pat. No. 4,940,725). The *Uncaria tomentosa* oxindole alkaloids tested in these experiments (described below) included isopteropodine, pteropodine, isomitraphylline and mitraphylline. Access to these alkaloids also allowed us to use them as markers to see if they were present in our bioactive extracts and fractions of PTI-777.

Example 7

Inhibition of Aβ Fibrillogenesis by PTI-777 and PTI-777 Individual Fractions

In one set of studies, Thioflavin T fluorometry and Congo red staining assays were used to compare the ability of PTI-777, PTI-777 individual fractions (including fractions F, G, H, J, K, L, M and N), PTI-00703, and alkaloids isolated from *Uncaria tomentosa*, to cause a disruption/disassembly of pre-formed Aβ 1-42 fibrils. As shown in FIG. 4, the results of 5 different Thioflavin T fluorometry experiments indicated that PTI-00703 caused a significant 53+/−2.5% disruption of pre-formed Aβ 1-42 fibrils. On the other hand, individual PTI-777 fractions including fraction F (64.0+/−1.7% inhibition), fraction G (62.3+/−8.5% inhibition), fraction H (56.3+/−2.1% inhibition), fraction J (68.7+/−2.0% inhibition), fraction K (which consisted of both $K_1$ and $K_2$; 58.0 +/−4.6% inhibition), fraction L (68.3+/−2.3% inhibition), fraction M (64.0+/−1.5% inhibition) and fraction N (63.0+/−1.0% inhibition) were all similarly quite effective in causing a significant disruption/disassembly of pre-formed Aβ 1-42 fibrils. Surprisingly, PTI-777 (i.e. mixture of fractions F through O) was a significantly more effective disrupter of Aβ 1-42 fibrils (by 87.3+/−3.0%) than any of the individual fractions tested. The alkaloids isolated from *Uncaria tomentosa* (isopteropodine, pteropodine, isomitraphylline and mitraphylline) had little or no effect on disruption disassembly of pre-formed Aβ 1-42 fibrils. These studies indicated that PTI-777 and its individual fractions were more effective Aβ amyloid disrupters, than PTI-00703 alone. In addition, it was evident that the combination of fractions such as observed with PTI-777 (a mixture of 7–11 major components) were even more active than any of the individual PTI-777 fractions alone, suggesting a possible synergistic effect between different PTI-777 components. Lastly, the fact that isolated alkaloids from Cat's claw (i.e. *Uncaria tomentosa*) were basically ineffective in the disruption of pre-formed Aβ 1-42 fibrils, suggested that oxindole alkaloids were not likely responsible for the Aβ amyloid inhibitory effects exerted by PTI-777, the individual PTI-777 fractions tested above, and PTI-00703. It is likely that compounds not previously isolated and identified from *Uncaria tomentosa* were actually responsible for the observed anti-Aβ amyloid inhibitory effects.

Figure 5A:
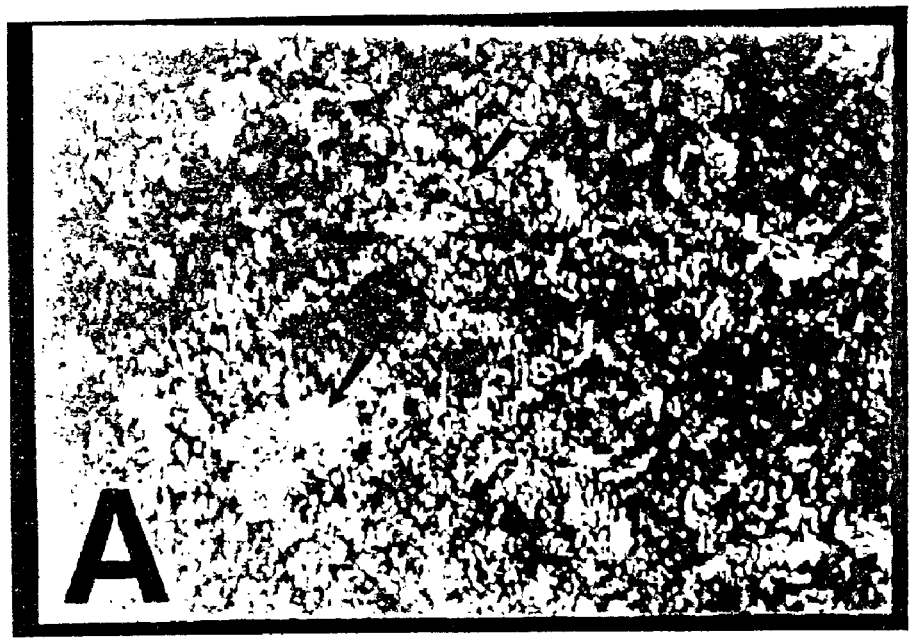
FIG. 5 is a Color Composite Demonstrating that PTI-777 and Individual Fractions of PTI-777 Cause of Disruption/Dissolution of Pre-Formed Alzheimer's Aβ Fibrils.
Figure 5B:
Figure 5C:
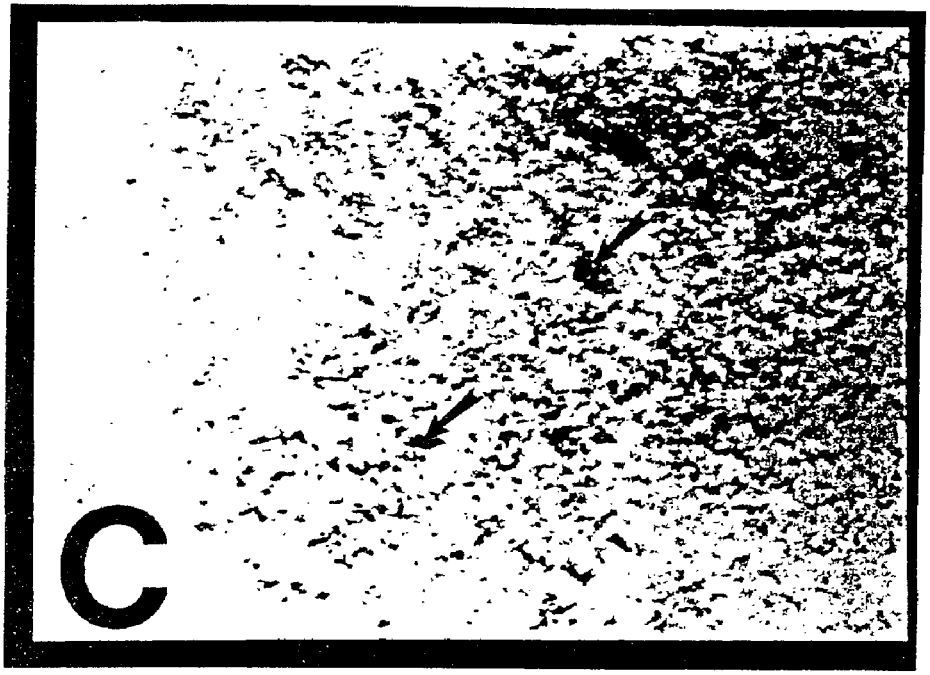
Figure 5D:

Congo red staining assay experiments confirmed the results of the Thioflavin T fluorometry studies, and revealed the efficacy of PTI-777 and individual PTI-777 fractions on their ability to disrupt Alzheimer's Aβ 1-40 and Aβ 1-42 pre-formed fibrils, as well as to inhibit Aβ 1-40 fibril formation. In these experiments, 125 μM of Aβ 1-40 or Aβ 1-42 was incubated at 37° C. for 1 weekin TBS either alone, or in the presence of increasing amounts of PTI-777, individual PTI-777 fractions isolated from HPLC, or PTI-00703. At 1, 3 and 7 days, 10 μl aliquots were taken, put on glass slides, air-dried, stained with Congo red and viewed under polarized light. Usually testing of Aβ:PTI-777 or individual PTI-777 fractions were at an Aβ:compound weight ratio of 1:1 or 1:5. An example of the results of one of these experiments is shown in FIG. 5. In this particular experiment, Aβ 1-42 was incubated either alone, or in the presence of PTI-777, fractions F, G, H, J, K (combined $K_1$ and $K_2$), L, M and N at 37° C. for 1 week at an Aβ:compound weight ratio of 1:5. As shown in FIG. 5A, Aβ 1-42 alone at 7 days displayed extensive amyloid congophilia (i.e. red/green birefringence) when viewed under polarized light indicative of massive amounts of amyloid fibrils (Puchtler et al, *J. Histochem. Cytochem.* 10:355–364, 1962). In contrast, Aβ 1-42 in the presence of PTI-777 (FIG. 5B), or other individual PTI-777 fractions including fraction F (FIG. 5C), G, H, J, K (not shown), L (FIG. 5D), M and N (not shown), all displayed a marked reduction in amyloid congophilia indicative of an inhibition of Aβ amyloid fibril formation.

Example 8

Disruption of β-Sheet Structure in Aβ 1-42 Fibrils by PTI-777 as Demonstrated by Circular Dichroism Spectroscopy In this study the effects of PTI-777 on potential disruption/disassembly of β-pleated sheet structure in Aβ 1-42 fibrils was determined by circular dichroism (CD) spectroscopy. 50 μM Aβ 1-42 (Bachem Inc) was incubated at 37° C. for 1 week in phosphate-buffered saline (pH 7.4) either alone or in the presence of PTI-777 (referred to as PTC12 in FIG. 6) at an Aβ:PTI-777 weight ratio of 1:0.1. CD spectra were collected at 25° C. on an AVIV CD Spectrometer 62DS. Measurements were carried out in a 0.5 mm path length quartz cuvette, over the range of 190–260 nm. The instrument was calibrated with an aqueous solution of (+)-10-camphorsulfonic acid. CD spectra consisted of an average of a series of scans made at 0.5 nm intervals. As shown in FIG. 6, Aβ 1-42 at 3 days (closed circles) and at 7 days (not shown) demonstrated a characteristic pattern of extensive β-pleated sheet structure as shown by the curve and minima at ~220 nm. In the presence of PTI-777 at both 3 days (open circles) and 7 days (closed triangles) an 85–90% disruption/disassembly of β-pleated sheet was observed as shown by a smoothing of the curve especially at 220 nm. This study indicated that PTI-777 is a potent disrupter of the β-sheet structure characteristic of Alzheimer's amyloid fibrils.

Example 9

Figure 7A:
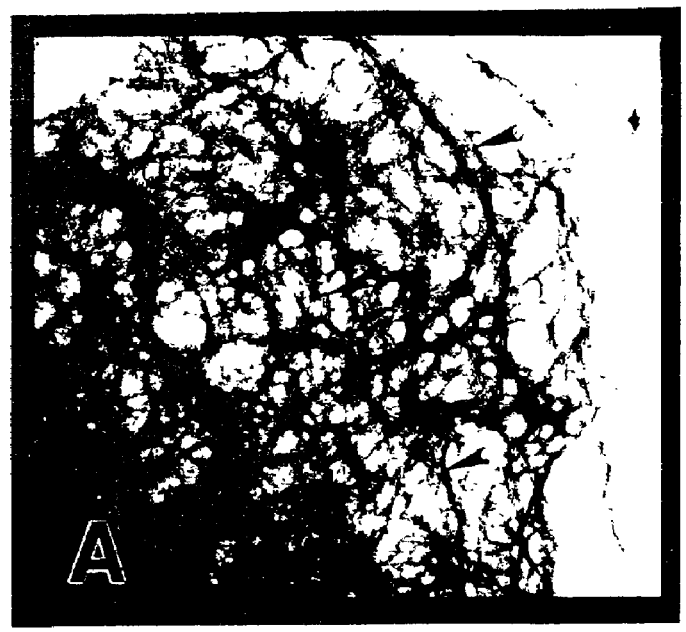
FIG. 7 is a Black and White Composite Demonstrating Inhibition of Alzheimer's Amyloid Fibril Formation as Demonstrated by Negative Stain Electron Microscopy.
Figure 7B:
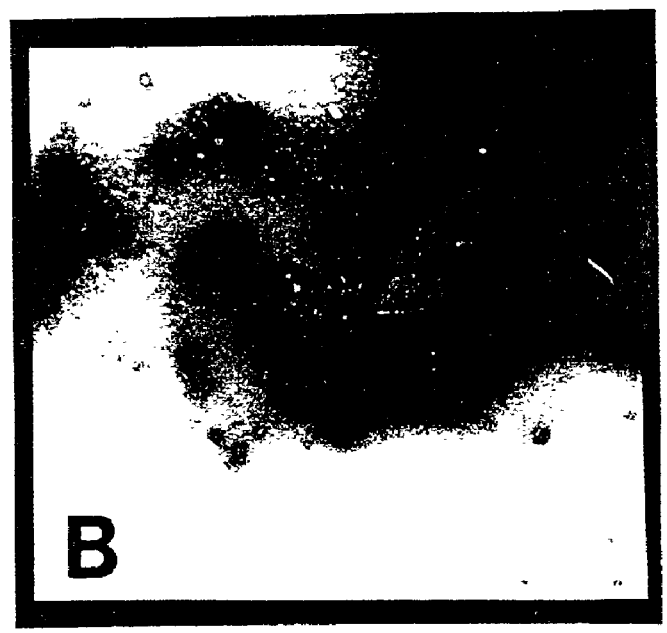

Inhibition of Alzheimer's Aβ Fibril Formation by PTI-777 as Demonstrated by Negative Stain Electron Microscopy The potent inhibition of Aβ 1-40 fibril formation by PTI-777, and to a lesser extent PTI-00703, observed at the light microscopic level by Thioflavin T fluorometry and Congo red staining assays, was confirmed by negative stain electron microscopy. A number of different experiments were initialized to further test the efficacy of PTI-777 and PTI-00703 on inhibition of Aβ 1-40 fibril formation. As an example in one study, 50 μM Aβ 1-40 was incubated at 37° C. for 7 days in the absence or presence of PTI-777 at an Aβ:compound weight ratio of 1:1, with aliquots taken at 0, 1, 3 and 7 days of incubation for analysis by negative stain electron microscopy. As shown in FIG. 7, amyloid fibrils were observed at 3 days of incubation of Aβ 1-40 alone (FIG. 7A, arrowheads). PTI-777 (FIG. 7B), and to a lesser extent, PTI-00703 (not shown), were both effective in preventing Aβ 1-40 amyloid fibril formation. Only amorphous non-fibrillar material was observed when Aβ 1-40 was incubated in the presence of PTI-777 (FIG. 7B, arrowheads). Similar observations on the ability of PTI-777 to cause a disruption/disassembly of pre-formed Alzheimer's Aβ 1-40 and 1-42 fibrils were also verified using electron microscopy (not shown).

Example 10

Marked Inhibition of Aβ 1-42 Amyloid Deposition by PTI-777 in a Rodent Model of Aβ Fibrillogenesis In one study, the Aβ amyloid inhibitory ability of PTI-00703 was directly compared to PTI-777 (on a weight to weight basis) in a rodent model of Aβ 1-42 amyloid deposition. 25 μg Aβ 1-42, 25 μg Aβ 1-42+PTI-777 or 25 μg Aβ 1-42+PTI-00703 were directly infused (using Alzet osmotic pumps) into hippocampus for 1 week in adult Sprague-Dawley rats (250–300 grams; 3 months old; n=9 per group). The Aβ:PTI-777 or Aβ:PTI-00703 weight ratio was 1:5. Amyloid deposition was assessed by the blind scoring of Congo red stained brain sections throughout the infusion site using an arbitrary scale (from 0 to 5), as previously described (Snow et al, *Neuron* 12:219–234, 1994). The results demonstrated that PTI-777 was a much more potent inhibitor of Aβ 1-42 fibril deposition than PTI-00703 (FIG. 8). Whereas animals infused with PTI-00703 showed a 62.7% inhibition, animals infused with PTI-777 demonstrated an impressive ($p<0.005$) 89.2% inhibition, of Aβ 1-42 fibril deposition. This study indicated that PTI-777 was ~26% more effective than PTI-00703 in inhibition of Aβ 1-42 fibril deposition in brain tissue.

Example 11

Marked Inhibition of Astrocytosis by PTI-777

In all animal model studies as described above, tissue sections throughout the infusion site were immunostained using a number of different glial marker antibodies to assess the effects of PTI-777 on both microgliosis (i.e. anti-OX 42 or anti-MAC1) and astrocytosis (i.e. anti-GFAP). Brain tissues obtained from animals infused with Aβ 1-42 only, or Aβ 1-42+PTI-777, and immunostained with microglial markers demonstrated positive infiltrating microglia at the infusion site (not shown), with no apparent reduction in microgilal infiltration by PTI-777. In fact, animals infused with PTI-777 actually demonstrated a greater number of infiltrating macrophages/microglia at the amyloid infusion sites. This is expected since *Uncaria tomentosa* (i.e. Cat's claw), from which PTI-777 is derived, is a known inducer of macrophage activation and infiltration (Keplinger et al, U.S. Pat. Nos. 4,844,901; 4,940,725; Laus and Keplinger, *J. Chromatography* 662:243–249, 1994; Laus et al, *Phytochem.* 45:855–860, 1997).

Figure 9A:
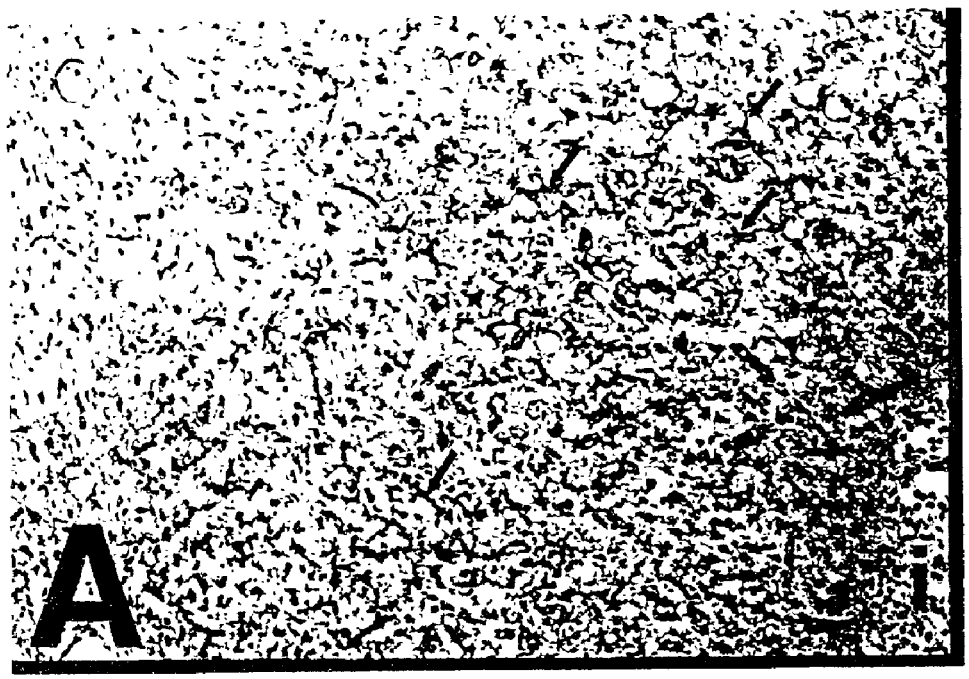
FIG. 9 is a Color Composite Demonstrating that PTI-777 Causes a Marked Inhibition of Astrocytosis in Brain.
Figure 9B:
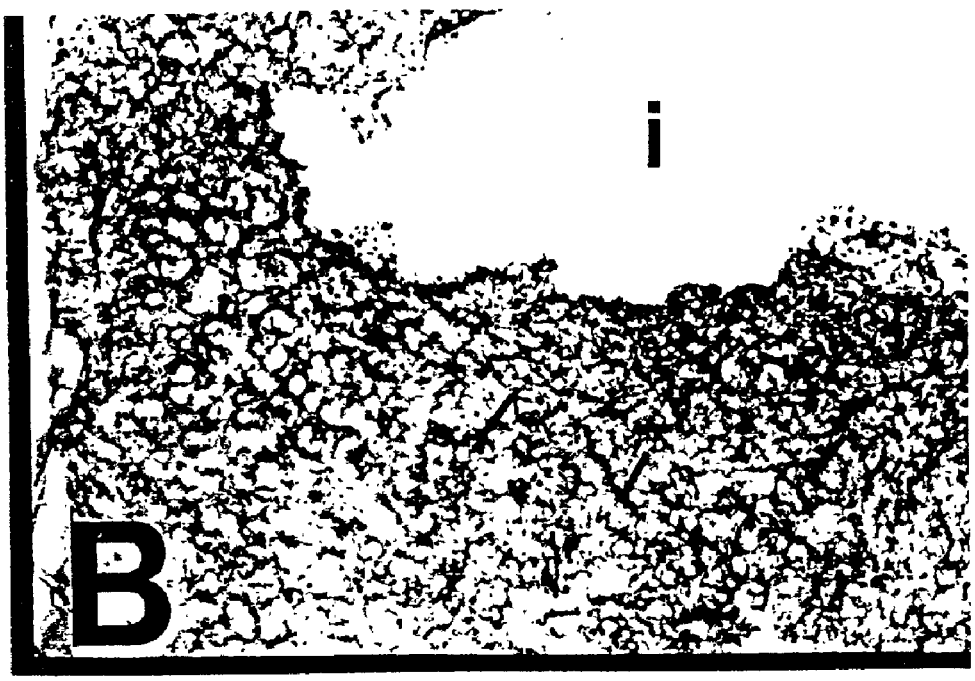
Figure 9C:
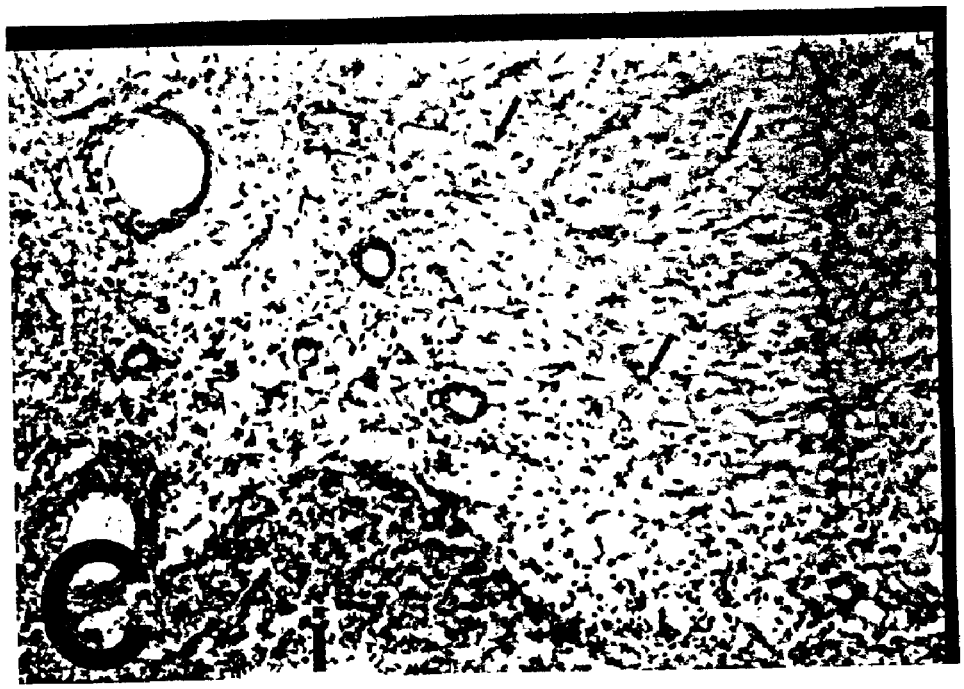
Figure 9D:

As expected, animals infused with Aβ 1-42, or due to the placement of the cannulae in hippocampus alone, showed a marked astrocytosis at the amyloid deposition and cannulae injury sites (FIGS. 9A, B). Surprisingly, however, hippocampi from animals infused with PTI-777 showed a marked reduction in GFAP immunostaining (FIGS. 9C, D), suggestive of a marked inhibition of astrocytosis by PTI-777.

Example 12

Final Purification of the PTI-777 Active Components: Fractions F and J

The preparative HPLC work on PTI-777 described above resulted in 11 major water-soluble active fractions, each of which contained at least one major compound. Compositional and structural studies demand that the major individual compounds within each fraction be purified to homogeneity in sufficient quantity for NMR and other spectroscopic studies (about 30–50 mg). Although each of the 11 fractions of PTI-777 showed significant activity in the in vitro assays, fractions F, J and H were singled out for initial final purification based on their starting purity as determined by analytical HPLC and the amount of material. These fractions were passed through the preparative HPLC column until they were deemed pure by comparison of the UTV diode array spectra taken at four points across the single chromatographic peak, and assessment.

Example 13

Fraction F Structurally Identified as Chlorogenic Acid

Fraction F was the first material to be purified in a quantity sufficient for structural elucidation work. Mass spectroscopy and NMR spectroscopic analysis were initially employed. Several different types of mass spectra [(chemical ionization (CI), fast atom bombardment (FAβ), and electron impact (EI)] were taken of the purified sample. A clear spectrum that revealed the molecular weight of the compound was never obtained under standard sampling conditions.

Figure 10A:
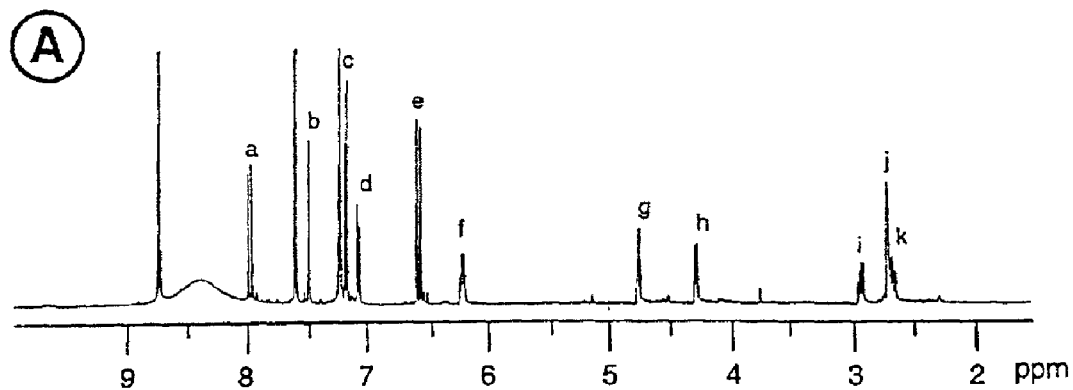
FIG. 10 are Black and White Graphs Demonstrating the $^1$H and $^{13}$C-NMR Profiles of Purified Fraction F of PTI-777. Figure A shows the $^1$H-NMR profile of purified fraction F in pyridine ($d_5$) showing 12 discrete signals. Figure B demonstrates the $^{13}$C-NMR profile of purified fraction F in pyridine ($d_5$) showing 16 discrete signal regions

The $^1$H-NMR (500 MHz) of fraction F in pyridine ($d_5$) showed 12 signals (FIG. 10A). A broad signal at about 8.4 ppm was attributed to OH groups on the compound. Two strongly coupled signals at 8.0 and 6.8 ppm and three aromatic signals at 7.5, 7.16 and 7.07 ppm were present in the spectrum, all indicative of H bound to $sp^2$ hybridized carbon atoms. There were also signals at 6.2, 4.75, 4.3, 2.9, 2.72 and 2.7 ppm. All of these signals with the exception of the ones at 8.4 and 2.72 ppm showed integration consistent with one proton. The integration of the 2.72 ppm signal was closer to 2 protons and the OH signal at 8.4 ppm was not integrated. The Correlation Spectroscopy (COSY) spectrum (a two dimensional NMR experiment identifying adjacent protons) showed that the protons responsible for the signals at 8.0 and 6.8 ppm were adjacent to each other. The large coupling constant of these two signals as well as their chemical shifts were indicative that these protons were attached to a carbon-carbon double bond system with trans geometry coupled to an aromatic ring. The COSY spectrum also revealed that the three aromatic protons were all on the same benzene ring and that the remaining six signals all showed connectivity indicating five contiguous carbon atoms.

Figure 10B:
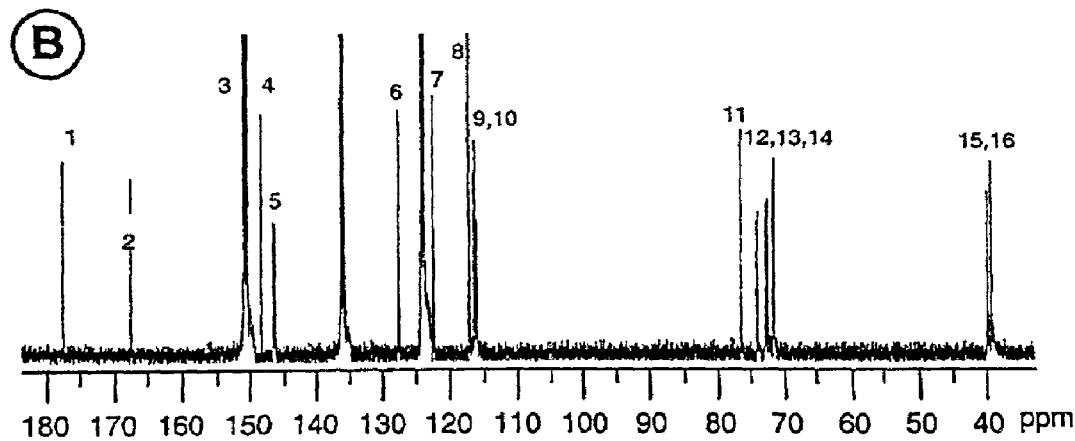

The $^{13}$C NMR (500 MHz) in pyridine ($d_5$) showed 16 discrete signal regions (FIG. 10B). The two signals at 177 and 167 ppm indicated the presence of two carbonyl C atoms. There were 8 carbons found in the shift range for $sp^2$ carbons (signals at 150, 147, 146, 127, 122, 117, 116 and 115 ppm). Three of these carbons showed doubled signals (146, 116 and 115 ppm). There were four signals (76, 74, 72 and 71 ppm) indicative of $sp^3$ carbons bonded to oxygen atoms. Three of these signals were doubled (74, 72 and 71 ppm). The two signals at 39.7 and 39.2 ppm were representative of $sp^3$ carbon atoms not bonded to oxygen. The six doubled signals were assumed to be due to a mixture of isomers. The Distortionless Enhancement by Polarization Transfer (DEPT) experiment (distinguishes between carbon atoms bonded to 1, 2, 3 or no H atoms) indicated that the aromatic carbon atoms showing signals at 150, 147 and 127 ppm were not bonded to H. This was also the case for the atom responsible for the signal at 76 ppm. The Heteronuclear Correlation Spectroscopy (HECTOR) experiment helped confirm which $^1H$ signals were associated with individual $^{13}C$ signals.

The diode array ultraviolet (UV) spectrum of fraction F showed a peak at 330 nm indicating a possible presence of an aromatic ring with extended conjugation. Analysis of both the $^1H$ and $^{13}C$ NMR data pointed to the presence of a tri-substituted aromatic ring with two phenolic groups and a conjugated ethylene group with trans geometry. The chemical shift of the carbonyl carbon at 177 pp, suggested that this signal was due to a carboxylic acid group attached to this conjugated system. The COSY data suggested a chain of five contiguous carbon atoms, three of which were oxygenated. Attachment of the remaining $sp^3$ quaternary carbon atom (76 ppm) to both ends of the five-carbon atom chain would form a cyclohexane ring, which would be consistent with the data. The remaining carbonyl carbon atom was assigned as a carboxylic acid group attached to the cyclohexane ring. The conjugated aromatic and the cyclohexane portions of the molecule were connected via an ester linkage, again consistent with the chemical shift data.

The structural features of fraction F were consistent with the compound, chlorogenic acid ($C_{16}H_{18}O_9$ MW 354.31) (FIG. 11). The structural assignment of fraction F as chlorogenic acid was confirmed by comparison of both the $^1H$ and $^{13}C$ NMR spectra of Fraction F with the published spectra of chlorogenic acid [("Aldrich Library of $^{13}C$ and $^1H$ FT NMR Spectra" I (2) 1235C)]. The spectra were identical when solvent dependent chemical shift changes were taken into account. The published UV spectrum of chlorogenic acid was also compared with that of fraction F and found identical. This study indicated that the major compound within fraction F was identified as chlorogenic acid.

Chlorogenic acid can be found in green coffee beans, and also occurs with its isomers (isochlorogenic acid and neochlorogenic acid) in fruit, leaves, and other tissues of dicotyledeneous plants. This compound forms caffeic acid on hydrolysis (Barnes et al, *J. Am. Chem. Soc.* 72:4178–4182, 1950; Corse et al, *Tetrahedron* 18:1207–1210, 1962), and due to its polyphenolic content (see FIG. 12) turns black with ferric chloride (Barnes et al, *J. Am. Chem. Soc.* 72:4178–4182, 1950; Harborne in *Phytochemical Methods. A Guide to Modern Technicues and Analysis.*, Chapman and Hill, London, N.Y., 1984, pp.38). Initial in vitro testing of commercially available chlorogenic acid (Sigma/Aldrich) indicated that it is a potent Aβ fibrillogenesis inhibitor (not shown) as determined by Thioflavin T fluorometry and Congo red staining assays as described herein.

Example 14

Successful Labeling of PTI-777 with $^3H$

In order to determine whether PTI-777 and/or its components have the capacity to cross the blood-brain-barrier and enter the brain, PTI-777 had to be effectively radiolabeled without affecting its structure. Due to its highly electron rich structure due the presence of OH groups such as those found in chlorogenic acid (i.e. fraction F), PTI-777 was initially labeled with tritium using proprietary atom bombardment technologies. 0.9 mCi of $^3H$-PTI-777 with specific activity of 1.25 mCi/mg (at a concentration of 1 mCi/ml) was prepared and used for animal work. FIG. 12 demonstrates the HPLC profile of unlabelled PTI-777 (upper panel) which is nearly identical to the HPLC profile of $^3H$-PTI-777, indicating that radiolabeling with tritium did little to alter the structure of PTI-777. The bottom panel of FIG. 12 demonstrates the distribution of radioactivity measured in 0.5 ml fractions that were eluted from the HPLC column and collected beginning at 16.5 minutes. This graph demonstrates that the HPLC peaks of PTI-777 also demonstrate the greatest radioactivity.

Example 15

Penetration of $^3H$-PTI-777 into Brain Tissue Following a Single Intravenous Administration In order to determine the potential ability of $^3H$-PTI-777 to enter into brain tissue (and cross the blood-brain-barrier), male and female Sprague-Dawley rats were administered with a single intravenous injection of $^3H$-PTI-777. Two animals per group were then sacrificed at 5 minutes, 1 hour, 6 hours and 24 hours following administration and the amount of $^3H$-PTI-777 in brain tissue was determined. As shown in FIG. 13, ~18,000 dpm/gram of brain tissue was found within 5 minutes following intravenous administration. By 1 hour, this had decreased to ~10,100 dpm/g brain tissue. However, at 24 hours, the brain tissue still contained ~7,000 dpm/gram brain tissue, indicating that ~41% of the initial dose found to enter the brain was retained in the brain tissue over a 24-hour period. This study suggested that the water-soluble amyloid inhibitory components of *Uncaria tomentosa* (i.e. PTI-777) have the capability to enter the brain, an d thus are anticipated to be effective for the inhibition of amyloid protein fibrillogenesis for central nervous system disorders, such as Alzheimer's disease, Down's syndrome, Parkinson's disease (with fibrils formed consisting of alpha-synuclein), and other amyloid disease as described herein.

Example 16

Fraction J Structurally Identified as Epicatechin

Fraction J was the second material to be purified in a quantity sufficient for structural elucidation work. Following the isolation and purification of PTI-777-compound "J", spectroscopic studies on the compound and its pentaacetate derivative revealed its structure to be the same as epicatechin ($C_{15}H_{14}O_6$; FW 290.27). The results of these spectroscopic studies are discussed below.

Mass Spectroscopy

PTI-777-Comoound J: Numerous attempts to obtain a reliable molecular ion peak of the compound using both the fast atom bombardment (FAB+) and chemical ionization (CI) techniques were unsuccessful. A reliable molecular ion peak (M+1 with m/z of 291.05) was however, obtained using electrospay techniques using both time-of-flight (FIG. 14) and fourier transform (FIG. 15) mass spectroscopy. This mass to charge (m/z) ratio of 290 is consistent with a possible molecular formula of $C_{14}H_{12}O_7$ or $C_{15}H_{14}O_6$. An electron impact (EI) initiated mass spectrum showed large m/z fragments at 123 ($C_7H_7O_2$), 139 ($C_7H_7O_3$), and 152 ($C_9H_8O_3$)(FIG. 16).

Pentaacetate derivative of compound J: Mass spectra taken in both the FAB+ (FIG. 17) and electron impact (EI) modes (FIG. 18) gave molecular ion peaks of 523 and 500 respectively correlating with a sodiated and non-sodiated pentaacetate derivative of a compound with molecular weight 290. High resolution spectra taken in these modes gave observed m/z ratios of 523.1214 ($C_{25}H_{24}O_{11}Na$ error–0.4 ppm/–0.2 mmu) and 500.1317 ($C_{25}H_{24}O_{11}$, error–0.2 ppm/–0.1 mmu). This information firmly established the molecular formula of the pentaacetate derivative of PTI-777-compound J as $C_{25}H_{24}O_{11}$ and hence, compound J to have the molecular formula corresponding to $C_{15}H_{14}O_6$.

Nuclear Magnetic Resonance (MNR) Spectroscopy.

PTI-777-Compound J: In $d_5$ acetone, the $^1H$ NMR spectrum (FIG. 19) of PTI-777 -compound J showed a doublet of doublets centered on 2.8 ppm (2H), a sharp multiplet at 4.2 ppm (1H), an apparent singlet at 4.85 ppm (1H), two singlets at 5.9 (1H) and 6.0 ppm (1H), two multiplets at 6.8 ppm (1H), a sharp multiplet at 7.02 ppm (1H) and four hydroxy signals at 7.83 (2H), 8.03 (1H), 8.2 (1H), and 3.6 ppm (1H). The $^{13}C$ NMR spectrum (FIG. 20) displayed 15 signals at 29.06, 66.98, 79.49, 95.72, 96.20, 99.85, 115.35, 115.53, 119.42, 132.35, 145.35, 145.46, 157.23, 157.65, and 157.65 ppm.

Both the $^1H$ (FIG. 21) and $^{13}C$ (FIG. 22) spectra in $D_2O$ with 0.1% triflouroacetic acid were significantly different form the above reported spectra. The $^1H$ spectrum (FIG. 21) differed most strikingly in the absence of the two singlets at 5.9 and 6.0 ppm. In the $^{13}C$ spectrum (FIG. 22), the three signals between 90 and 100 ppm moved to just above 160 ppm. The sample remained stable in the acidified $D_2O$ when stored over the course of several months at room temperature, but it begins to degrade in acetone within 24 hours.

Correlation spectroscopy (COSEY) spectra of the sample in both $d_6$ acetone (FIG. 23) and acidified $D_2O$ (FIGS. 24A–C) revealed coupling between the 3 signals from 6.8 to 7.1 ppm and the signals at 2.8 and 4.2 ppm.

Pentaacetate derivative of PTI-777-compound J: The expected methyl groups and carbonyl carbon atoms were present in both the proton and carbon spectra of the acetylated derivative of J. The most striking changes in the $^1H$ MNR spectrum ($CDCl_3$) upon acetylation (FIG. 25) were the downfield shifts of about 0.6 ppm of the two singlets at 5.9 and 6.0 ppm and the downfield shift of 1.2 ppm of the apparent singlet at 4.85 ppm (compare to FIG. 21). The $^{13}C$ spectrum (FIG. 26) was less affected, but the aromatic carbon atoms were, in general, shifted downfield upon acetylation. All 15 carbon signals associated with compound J were readily seen in the spectrum.

In addition to the $^1H$-$^1H$ coupling detected in the COSEY spectrum of the unacetylated compound (FIG. 23, 24A–C), the derivative (FIG. 27) showed a connection between the apparent singlet at 4.85 ppm and the sharp multiplet at 4.2 ppm of the original compound. The heteronuclear correlation spectroscopy (HETCOR) spectrum (FIGS. 28A–28C) of the acetylated derivative was consistent with expectation and confirmed and the assignment and the identity of the protonated carbon atoms.

Ultra Violet (UV) Spectroscopy: The UV spectrum of PTI-777-compound J showed a maximum at 278 nm consistent with an aromatic phenolic compound (FIG. 29).

Structural Assignment: The $^{13}C$ NMR spectrum showed the presence of three $sp^3$ type carbon atoms, 9 $sp^2$ carbon atoms (no carbonyl carbons) and 3 carbon atoms that were either very upfield $sp^2$ type or very downfield $sp^3$ type carbon atoms. The $^1H$ MNR spectrum indicated the presence of 4 phenolic hydroxyl groups and one non-aromatic hydroxyl group. The major fragments observed in the EI mass spectrum corresponded to dihyroxylated benzene rings without and with carbon group substitution (m/z of 123, 139 and 152). The proton NMR data (6.8–7.02 ppm) showed evidence for a tri-substituted benzene ring that was hydroxylated. Comparison of $^1H$ NMR spectra data of model compounds with that of compound J, showed that the observed splitting pattern and chemical shifts of the signals were consistent with a 1-substitued, 3,4-dihydroxy benzene structure.

The COSEY spectra showed $^1H$-$^1H$ coupling in a contiguous three-carbon fragment. The relative chemical shifts of two of these carbon atoms indicated that they were directly bonded to oxygen atoms. The large chemical shift change observed for the signal at 4.85 ppm upon acetylation indicated the location of the non-aromatic hydroxyl group and the chemical shift of the third carbon atom implied that it was benzylic. Together, these data were consistent with the following structure, Ar—$CH_2$—CH(OH)—CH(R)O.

The above fragments accounted for all but 4 hydrogen atoms (two of which are found in phenolic type OH groups) and for all but 6 carbon atoms (3 $sp^2$ type and 3 intermediate between $sp^3$ and $sp^2$ type). The $C_6H_4$ formula indicated a high degree of unsaturation consistent with a second aromatic ring. The remaining unaccounted for singlets in the $^1H$ NMR at 5.9 and 6.0 ppm revealed that this ring was tetra substituted and electron rich. These data indicated that this benzene ring was bonded to three oxygen atoms (two hydroxy groups and one ether) and one carbon atom.

These three structural units (two phenolic rings and the three carbon fragment) when connected together form a flavanol structure identical to the diastereomers, catechin and epicatechin. Comparison of the $^1H$ and $^{13}C$ NMR spectra, as well as the infrared (IR) spectra, of compound J with the published spectra (Aldrich collection) for catechin and epicatechin (FIGS. 31, 32) established the identity of PTI-777-compound J as epicatechin. The splitting pattern of doublet of doublets center on 2.8 ppm in the $^1H$ NMR spectrum matches that of the epicatechin reference spectrum. The pattern of the aromatic signals between 6.8 and 7.02 ppm is also most similar to that of epicatechin (allowance must be made for differences in solvents and spectrometer field strengths). The IR spectrum of compound J matches closely with that of epicatchin, while the IR spectrum of catechin differs significantly in the fingerprint region.

Example 17

Compound "H" Demonstrates Potent Disassembly/Dissolution of Aβ 1-42 Fibrils

Further purification of fraction H led to the isolation of the major compound within this fraction (known as compound H), which ran as a single peak on HPLC (not shown). The following methodology was used to isolate compound H from PTI-777. This methodology is different in some ways to the previous examples presented in the specification.

PTI-777 was placed on an LH-20 column. The material was eluted with successive column volumes of water/methanol mixtures containing 0.1% TFA, beginning with 25% methanol and increasing to 100% menthol in 25% increments. These fractions were analyzed by analytical HPLC, those fractions containing the peak designated as "compound H", were combined, and the solvent removed with the aid of a rotary evaporator. A Dynamax C-18, 5 m column (with dimensions of 4.6 mm×25 cm) was used for analytical HPLC using a gradient of distilled water (solvent A) and methanol (solvent B) each containing 0.1% TFA, with detection at 280 nm. The gradient conditions were 0.0 to 9.0 min (25% to 36% B gradient), 3.0 to 10.0 min (36 to 100% B gradient), 10.0 to 12.0 min (100% B) and 12.0 to 13.0 min (100 to 25% B gradient), all at a flow rate of 20.0 ml/min.

The resulting material was dissolved in water/methanol (80/20) containing 0.1% TFA and applied (150 mg/run) to a preparative HPLC column (Dynamx C-18, 5 m, 21.4 mm×25 cm) fitted with an appropriate guard column. The following gradient conditions were used where solvent A was water with 0.1% TFA and solvent B was methanol with 0.1% TFA. The preparative HPLC gradient conditions were 0.0 to 3.0 min (20% B to 25% B), 3.0 to 9.0 min (25 to 45% B), 9.0 to 10.0 min (45 to 100% B), 10.0 to 12.0 min (100% B) and 12.0 to 13.0 min (100 to 25%), all at a flow rate of 20.0 ml/min. Detection was at 280 and 300 nm.

The H containing fractions obtained from the preparative column, were reanalyzed by analytical HPLC and appropriately combined. They were then concentrated on a rotary evaporator and the remaining solvent was removed using a Speed-Vac® drying apparatus. The material was re-chromatographed using the preparative procedure outlined above until a pure material, known as "compound H", was obtained as determined by analytical HPLC and a dry sample of the compound was obtained as described.

Initial characterization studies of "compound H" indicates that it also contains an aromatic ring to which hydroxyl groups are attached (not shown)

Thus, "compound H" appears to belong to the group of compounds known as "polyphenolics". Compound "H" was tested in direct comparison to PTI-777 in order to determine its relative efficacy in causing disassembly/disruption of pre-formed Aβ 1-42 fibrils. Although the exact structure of this compound is unknown at this time, the data described below indicates that "compound H" is potent in causing disassembly/dissolution of pre-formed Aβ 1-42 fibrils and is therefore an important amyloid inhibiting component of PTI-777.

In one study, Thioflavin T fluorometry was used to determine the effects of PTI-777, "compound H" and EDTA (as a negative control) on disassembly/dissolution of pre-formed Aβ 1-42 fibrils. In this study, 25 μM of pre-fibrillized Aβ 1-42 (Bachem Inc) was incubated at 37° C. for 1 week either alone, or in the presence of PTI-777, "compound H", or EDTA at an Aβ:test compound weight ratio of 1:1 (approximate molar ratio of 1:10). Following a 1 week incubation 50 μl of each incubation mixture was transferred into a 96-well microtiter plate containing 150 μl of distilled water and 50 μl of a Thioflavin T solution (i.e. 500 mM Thioflavin T in 250 mM phosphate buffer, pH 6.8). The fluorescence was read at 485 nm (444 nm excitation wavelength) using an Elisa plate fluorometer after subtraction of buffer alone as blank. As shown in FIG. 33, whereas EDTA caused no significant inhibition of Aβ 1-42 fibrils, PTI-777 demonstrated a significant 93.7% disruption/disassembly of pre-formed Aβ 1-42 fibrils, whereas "compound H" caused a significant 93.2% disruption/disassembly of pre-formed Aβ 1-42 fibrils, as indicated by the marked lowering of fluorescence.

The disruption of Aβ 1-42, even in its monomeric form, was confirmed by a study involving the use of SDS-PAGE and Western blotting methods. In this latter study, triplicate samples of pre-fibrillized Aβ 1-42 (25 μM) was incubated at 37° C. for 1 week either alone or in the presence of PTI-777 (1:1 wt/wt ratio), compound "H" (1:1 wt/wt ratio) or EDTA (1:1 wt/wt ratio). 5 μg of each sample was then filtered through 0.22 μfilter. 1 μg of protein recovered from the filtrate was then loaded per lane, and ran on 10–20% Tris-Tricine SDS-PAGE, blotted to nitrocellulose and detected by ECL using an anti-Aβ antibody (clone 6E10; Senetek). As shown in FIG. 34, Aβ 1-42 was detected as a ~4 kilodalton band (i.e. monomeric Aβ) following incubation alone, or in the presence of EDTA. Aβ 1-42 monomers were not detected following the incubation of Aβ 1-42 with either PTI-777 or "compound H" (FIG. 34) suggesting that both were capable of causing a disappearance of monomeric Aβ 1-42.

Further Aspects and Utilizations of the Invention

Therapeutic Applications

One embodiment of the present invention is to formulate prior to administration in a patient, a pharmaceutical formulation comprising PTI-777 (and/or one or more of its individual components such as chlorogenic acid, epicatechin or "compound H") in one or more pharmaceutical acceptable carriers, diluents or excipients. In a preferred embodiment, a patient who has Alzheimer's disease, type II diabetes, Parkinson's disease, or any other amyloidosis, would orally consume PTI-777 or components thereof in pill, tablet, caplet, soft and hard gelatin capsule, lozenge, vegicap, liquid drop, solution, syrup, tea bag, and/or bark powder form.

In another preferred embodiment PTI-777 (and/or one or more of its individual components) in any form could be further modulated using suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweeting agents or flavoring agents. The compositions of the invention may be formulated so as to provide quick, sustained or delayed response of the active ingredient after administration to the patient. The compositions are preferably formulated in a unit dosage form, each dosage containing from about 1 to about 1000 mg of PTI-777 (and/or one or more of its individual components) more usually about 400 to about 750 mg of PTI-777 (and/or one or more of its individual components). However, it will be understood that the therapeutic dosage administered will be determined by the physician in the light of the relevant circumstances including the clinical condition to be treated, the organ or tissues affected or suspected to be affected with amyloid accumulation, and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. For each formulation provided as an example, lowering or raising of the PTI-777 (and/or one or more of its individual components) concentration will cause a proportional lowering or raising of the other ingredients as indicated. Hard gelatin capsules may be prepared by using 500 mg of PTI-777 (and/or one or more of its individual components), 400 mg of starch, and 20 mg of magnesium stearate. The above ingredients are mixed and filled into hard gelatin capsules in 920 mg quantities.

A tablet is prepared by using 500 mg of PTI-777 (and/or one or more of its individual components), 800 mg of microcrystalline cellulose, 20 mg of fumed silicon dioxide and 10 mg of stearic acid. The components are blended and compressed to form tablets each weighing 1230 mg.

An aerosol solution is prepared by using 0.25 active ingredient, 29.75 ethanol, and 70 of propellant 22 (chlorodifluoromethane). The PTI-777 (and/or one or more of its individual components) is mixed with ethanol. The mixture is added to a portion of the Propellent 22, cooled to −30° C., and transferred to a filling device. The required amount is then fed to a stainless steel container and diluted with the remainder of the propellent. The value units (listed above) are then fitted to the container. Such an aerosol form of PTI-777 (and/or one or more of its individual components) may be useful for the treatment of amyloids involving the brain (such as Alzheimer's disease, Down's syndrome, prion diseases, Parkinson's disease etc) by using an aerosol or nasal spray. Previous studies have suggested that in these central nervous system amyloidoses the initial form of entry of a possible environmental agent which may be playing a role in pathogenesis may be derived from the outside world through the nasal passages.

Tablets are made by using 120 mg of PTI-777 (and/or one or more of its individual components), 90 mg of starch, 70 mg of microcrystalline cellulose, 8 mg of polyvinylpyrrolidone (as 10% in water), 9 mg of sodium carboxymethyl starch, 1 mg of magnesium stearate and 1 mg of talc (total=300 mg). PTI-777 (and/or one or more of its individual components), starch and cellulose are passed through a No.45 mesh U.S. sieve and mixed thoroughly. The solution of polyvinylpyrrolidone is mixed with the resultant powders which are then passed through a No. 14 mesh U.S. sieve. The granules so produced are dried at 50oC. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 300 mg.

Capsules each containing 160 mg of medicant are made by using 160 mg of PTI-777 (and/or one or more of its individual components), 118 mg of starch, 118 mg of microcrystalline cellulose, and 4 mg of magnesium stearate (total=400 mg). The PTI-777 (and/or one or more of its individual components), cellulose, starch and magnesium stearate are blended, passed through a No. 45 mesh U.S. sieve, and filled into hard gelatin capsules in 400 mg quantities.

Suppositories each containing 225 mg of PTI-777 (and/or one or more of its individual components) are made by using 225 mg of PTI-777 (and/or one or more of its individual components), 2,000 mg of saturated fatty acid glycerides (total=2,225 mg). The PTI-777 (and/or one or more of its individual components) are passed through a No. 60 mesh U.S. sieve and suspended in the saturated fatty acid glycerides previously melted using the minimum heat necessary. The mixture is then poured into a suppository mold of nominal 2 g capacity and allowed to cool.

Suspensions each containing 50 mg of medicant per 5 ml dose are made by using 50 mg of PTI-777 (and/or one or more of its individual components), 50 mg of sodium carboxymethyl cellulose, 1.25 ml of syrup, 0.10 ml of benzoic acid solution, flavor, color, and purified water to total 5 ml. The medicant is passed though a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

An intravenous formulation is prepared by using 250 mg of PTI-777 (and/or one or more of its individual components), and 1000 mg of isotonic saline. The solution of the above ingredients is administered intravenously at a rate of 1 ml per minute to a subject in need of treatment.

In a preferred embodiment the therapeutic compound of the invention can be administered in any pharmaceutically acceptable vehicle. As used herein "pharmaceutically acceptable vehicle" includes, but is not limited to, any and all solvents, sterile liquids, such as water and oils, including those of petroleum, animal, vegetable or synthetic origin, such as peanut oil, soybean oil, mineral oil, sesame oil and the like, dispersion media, coatings, antibacterial and antifungal agents, isotonic and adsorption delaying agents, and the like which are compatible with the activity of the compound and are physiologically acceptable to the subject. An example of a pharmaceutically acceptable vehicle is buffered normal saline (0.15 molar NaCl). The use of such media and agents for pharmaceutically active substances is well known in the art. Supplementary active compounds can also be incorporated into the compositions. Suitable pharmaceutical excipients include starch, glucose, lactose, sucrose, gelatin, malt, rice, fluor, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

In the methods of the invention, amyloid formation, deposition, accumulation and/or persistence in a subject is inhibited by administrating PTI-777 (and/or one or more of its individual components) in a therapeutic dosage to the subject. The term subject is intended to include living organisms in which amyloidosis can occur. Examples of subjects include humans, monkeys, cows, dogs, sheep, cats, mice, rats, and transgenic species thereof. Administration of the compositions of the present invention to a subject to be treated can be carried out using known procedures, at dosages and for periods of time effective to inhibit amyloidosis in the subject. An effective amount of the therapeutic compound necessary to achieve a therapeutic effect may vary according to factors such as the amount of amyloid already deposited at the organ or tissue site in the subject, the age, sex and weight of the subject, and the ability of the therapeutic compound to inhibit amyloid formation, deposition accumulation, persistence, and/or to cause dissolution of pre-formed amyloid in the subject. Dosage regimens can therefore be adjusted to provide the optimum therapeutic response. For example, several divided doses may be administered daily or the dose may be proportionally reduced as indicated by the needs of the therapeutic situation. A non-limiting example of an effective dose range for PTI-777 (and/or one or more of its individual components) is between 400 and 1000 mg/kg of body weight/per day.

Different modes of delivery of PTI-777 (and/or one or more of its individual components) may be used. Accordingly, a preferred route of administration is oral administration. Alternatively, PTI-777 (and/or one or more of its individual components) may be administered by other suitable routes such as subcutaneous, intravenous, intraperitoneal, all routes administered by injection.

Depending on the route of administration, the active compound may be coated in a material to protect the compound from the action of acids and other natural conditions which may inactivate the compound.

To administer PTI-777 (and/or one or more of its individual components), it may be necessary to coat the compound with, or co-administer the compound with, a material to prevent its activation. For example, the therapeutic compound may be administered to a subject in an appropriate carrier, for example, liposomes or a diluent. Pharmaceutically acceptable diluents include saline and aqueous buffer solutions. Liposomes include water-in-oil-in-water CGF emulsions as well as conventional liposomes.

The PTI-777 (and/or one or more of its individual components) may also be administered parenterally or intraperitoneally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions or dispersions and sterile powders for the preparation of sterile injectable solutions or dispersion. In all cases, the composition must be sterile and must be fluid to the extent that easy use in the syringe exists. It must be stable under the conditions of manufacture and storage and must be preserved against the contaminating action of microorganisms such as bacteria and fungi. The vehicle can be a solvent or dispersion medium containing, for example, water, ethanol, polyol (for example glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, prabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the therapeutic agent plus any desired ingredients from a previously sterile-filtered solution thereof.

The PTI-777 (and/or one or more of its individual components) for Alzheimer's disease and other central nervous system amyloidoses may be optimized to cross the blood-brain barrier, although initial studies as shown in Example 14 demonstrate that PTI-777 (and/or one or more of its individual components) has the ability to cross the blood-brain-barrier and enter the brain. However, if optimization is necessary, methods of introductions include but are not limited to systemic administration, parenteral administration i.e., via an intraperitoneal, intravenous, perioral, subcutaneous, intramuscular, intraarterial, intradermal, intramuscular, intranasal, epidural and oral routes. In a preferred embodiment, PTI-777 (and/or one or more of its individual components) may be directly administered to the cerebrospinal fluid by intraventricular injection. In a specific embodiment, it may be desirable to administer PTI-777 (and/or one or more of its individual components) locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment PTI-777 (and/or one or more of its individual components) may be delivered in a controlled release system, such as an osmotic pump. In yet another embodiment, a controlled release system can be placed in proximity to the therapeutic target, ie. the brain, thus requiring only a fraction of the systemic dose.

INDUSTRIAL APPLICABILITY

Methods of isolation for the identification and purification of the potent amyloid inhibitory ingredients are disclosed. Use of such extracts from the inner bark and root parts of *Uncaria tomentosa* and related plant materials are anticipated to be of enormous benefit to human patients with Alzheimer's disease, type II diabetes, Parkinson's disease and other amyloidoses throughout the world, due to the previously unknown ability of these compounds to inhibit amyloid fibril formation, and cause disruption/ dissolution of pre-formed amyloid fibrils.

The disclosed methods are currently the only known methods by which to produce these previously unknown extracts and compounds. They are anticipated to be readily manufacturable in scaled up commercial production facilities, and made available to the world's population.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

We claim:

1. A method for isolating amyloid inhibitory components from *Uncaria tomentosa*, the method comprising the steps:
   a) adding 4000 ml of methanol to 1 kg of *Uncaria tomentosa* and mixing;
   b) centrifuging the mixture at ×2,500 g using a centrifuge for 30 minutes and pouring off the supernatant from a remaining residue;
   c) adding a second volume of methanol to the residue and repeating step b;
   d) combining the supernatants from step b and c and evaporating until reduced in volume to about 4–5% of the volume of the supernatents using a rotary evaporator at 50° C.;
   e) taking the reduced volume, washing 4 times with 300 ml of petroleum ether, and discarding the ether layer;
   f) evaporating the methanol to dryness to form a solid material using a rotary evaporator at 50° C.;
   g) extracting the solid material 5 times with 150 ml of distilled water, followed by centrifugation at 2,500×g for 30 minutes each time;

h) combining the supernatants from step g and then lypohilizing using a freeze-dryer;

i) dissolving the resulting lypohilized extract into about 500 ml of distilled water, and applying 50–100 ml portions of the dissolved extract to a 400 ml LH-20 column equilibrated j) eluting the LH-20 column with ~3 column volumes of distilled water and discarding the amber/yellow eluate;

k) eluting the LH-20 column with ~3 column volumes of methanol, collecting the eluate and evaporating it to dryness using a rotary evaporator at 50° C;

l) dissolving the product of step k in water to a concentration of ~80 mg/ml and applying 5 ml at a time to a 10 gm disposable C18 SPE column equilibrated in solvent A, where solvent A is 95% water/5% acetonitrile/0.1% TFA;

m) washing the column with 3 volumes of solvent A and discarding the eluate;

n) eluting the column with 3 volumes of solvent A containing 12.5% solvent B, where solvent B is 95% acentronitrile/5% water/0.1% TFA, and lyophilizing the eluate;

o) injecting 50 mg portions of the lyophilized eluate of step n into a Hewlett-Packard 1100 Series HPLC instrument with diode array detector, fitted with a 2.2 cm×25 cm Vydac 218TP1022 C18 reverse-phase column maintained at 25° C. and at a flow rate of 5 ml/min;

p) eluting the sample with the following solvent profile, 10% solvent B for minutes 0 to 20, 10–100% solvent B gradient for minutes 20 to 30, and 100–10% solvent B gradient for minutes 30–31; and q) seperating and collecting at least one fraction selected from the following fractions: fraction G (~13–14 minutes), fraction F (~15–16 minutes), fraction H (~17–20 minutes), fraction I (~21 minutes), fraction J (~22–23 minutes), fraction K1 (~24 minutes), fraction K2 (~25 minutes), fraction L (~26–27 minutes), fraction M (~27–28 minutes), and fraction N (~28–29 minutes).

2. A method for isolating amyloid inhibitory components from *Uncaria tomentosa*, the method comprising the steps:

a) dissolving a quantity of *Uncaria tomentosa* in one or more volumes of methanol;

b) seperating and combining the supernatant from each volume, and reducing it in volume through evaporation;

c) taking the reduced volume, washing it with petroleum ether and discarding any ether layer, and evaporating any remaining methanol to dryness to form a solid material;

d) extracting the solid material with a plurality of volumes of distilled water and combining the supernatant volumes, and then lyophilizing using a freeze-dryer;

e) dissolving the resulting lyophilized extract into about 500 ml of distilled water, and applying 50–100 ml portions of the dissolved extract to a 400 ml LH-20 column equilibrated with distilled water;

f) eluting the LH-20 column with ~3 column volumes of distilled water and discarding the amber/yellow eluate;

g) eluting the LH-20 column with ~3 column volumes of methanol, collecting the eluate and evaporating it to dryness;

h) dissolving the product of step g in water to a concentration of ~80 mg/ml and applying 5 ml at a time to 10 gm disposable C18 SPE column equilibrated in solvent A, where solvent A is 95% water/5% acetonitrile/0.1% TFA;

i) washing the C18 SPE column with 3 volumes of solvent A and discarding the eluate;

j) eluting the column with 3 volumes of solvent A containing 12.5% solvent B, where solvent B is 95% acentronitrile/5% water/0.1% TFA, and lyophilizing the eluate;

k) injecting 50 mg portions of the lyophilized eluate of step j into a Hewlett-Packard 1100 Series HPLC instrument, fitted with a Vydac 218TP1022 C18 reverse-phase column or the like, and maintained at about 25° C. and at a flow rate of 5 ml/min;

l) eluting the sample with the following solvent profile, 10% solvent B for minutes 0 to 20, 10–100% solvent B gradient for minutes 20 to 30, and 100–10% solvent B gradient for minutes 30–31; and m) seperating and collecting at least one fraction selected from the following fractions: fraction G (~13–14 minutes), fraction F (~15–16 minutes), fraction H (~17–20 minutes), fraction I (~21 minutes), fraction J (~22–23 minutes), fraction K1 (~24 minutes), fraction K2 (~25 minutes), fraction L (~26–27 minutes), fraction M (~27–28 minutes), and fraction N (~28~29 minutes).

* * * * *

UNITED STATES PATENT AND TRADEMARK OFFICE
CERTIFICATE OF CORRECTION

| | | |
|---|---|---|
| PATENT NO. | : 6,929,808 B2 | Page 1 of 1 |
| APPLICATION NO. | : 10/053625 | |
| DATED | : August 16, 2005 | |
| INVENTOR(S) | : Gerardo Castillo et al. | |

It is certified that error appears in the above-identified patent and that said Letters Patent is hereby corrected as shown below:

In column 43, line 6 of the Patent (Claim 1, i) "column equilibrated" is corrected to read --column equilibrated with distilled water--.
On the Title Page Item -75-, on the Title Page Item (57) Abstract Inventors of the Patent, "Elizabeth Nguyen" is corrected to read --Beth Nguyen--.
In the Abstract, line 4 of the Patent, "Uncaria tomentos" is corrected to read --Uncaria tomentosa--.
In column 1, line 20 before "BACKGROUND OF THE INVENTION", a paragraph is added to read "This invention was made with government support under AG16551 awarded by the National Institute on Aging. The government has certain rights in the invention."

Signed and Sealed this

First Day of January, 2008

JON W. DUDAS
*Director of the United States Patent and Trademark Office*